(12) United States Patent
Strathmann

(10) Patent No.: US 7,272,507 B2
(45) Date of Patent: Sep. 18, 2007

(54) APPLICATIONS OF PARALLEL GENOMIC ANALYSIS

(76) Inventor: Michael Paul Strathmann, 5300 Harbour Pointe Blvd. #302-B, Mukilteo, WA (US) 98275

( * ) Notice: Subject to any disclaimer, the term of this patent is extended or adjusted under 35 U.S.C. 154(b) by 256 days.

(21) Appl. No.: 10/209,676

(22) Filed: Jul. 30, 2002

(65) Prior Publication Data

US 2003/0148313 A1     Aug. 7, 2003

Related U.S. Application Data

(63) Continuation-in-part of application No. 09/427,834, filed on Oct. 26, 1999, now Pat. No. 6,480,791.

(51) Int. Cl.
*G01N 33/53*     (2006.01)
*G06F 19/00*    (2006.01)
*C12Q 1/68*     (2006.01)
*C12P 19/34*    (2006.01)

(52) U.S. Cl. .............................. 702/20; 435/6; 435/91.2
(58) Field of Classification Search .................. 702/20; 435/6

See application file for complete search history.

(56) References Cited

U.S. PATENT DOCUMENTS 5,935,793 A * 8/1999 Wong ............................ 435/6

* cited by examiner

*Primary Examiner*—Marjorie A. Moran

(57) ABSTRACT

The present invention provides parallel methods for determining nucleotide sequences of polynucleotides associated with sample tags. Applications of sequence information acquired by these methods are also provided.

2 Claims, 8 Drawing Sheets

SEQUENCE LISTING

<160> NUMBER OF SEQ ID NOS: 49

<210> SEQ ID NO 1
<211> LENGTH: 33
<212> TYPE: DNA
<213> ORGANISM: Artificial Sequence
<220> FEATURE:
<223> OTHER INFORMATION: Tag

<400> SEQUENCE: 1
cagcaccagg aaggtggcca ggttggcagt gta                33

<210> SEQ ID NO 2
<211> LENGTH: 33
<212> TYPE: DNA
<213> ORGANISM: Artificial Sequence
<220> FEATURE:
<223> OTHER INFORMATION: Tag

<400> SEQUENCE: 2
cctagctctc ttgaagtcat cggccagggt gga                33

<210> SEQ ID NO 3
<211> LENGTH: 26
<212> TYPE: DNA
<213> ORGANISM: Artificial Sequence
<220> FEATURE:
<223> OTHER INFORMATION: Tag

<400> SEQUENCE: 3
atcaagctta tggatcccgt cgacct                       26

<210> SEQ ID NO 4
<211> LENGTH: 33
<212> TYPE: DNA
<213> ORGANISM: Artificial Sequence
<220> FEATURE:
<223> OTHER INFORMATION: Tag

<400> SEQUENCE: 4
ggtgctcgtg tctttatcgt ccctacgtct ctt                33

<210> SEQ ID NO 5
<211> LENGTH: 28
<212> TYPE: DNA
<213> ORGANISM: Artificial Sequence
<220> FEATURE:
<223> OTHER INFORMATION: Tag

<400> SEQUENCE: 5
aattttgaag ttagctttga ttccattc                     28

<210> SEQ ID NO 6
<211> LENGTH: 30
<212> TYPE: DNA
<213> ORGANISM: Artificial Sequence
<220> FEATURE:
<223> OTHER INFORMATION: Tag

<400> SEQUENCE: 6
ggcgtcctgc tgcagtctgg cattggggaa                   30

<210> SEQ ID NO 7
<211> LENGTH: 27

```
<212> TYPE: DNA
<213> ORGANISM: Artificial Sequence
<220> FEATURE:
<223> OTHER INFORMATION: Tag

<400> SEQUENCE: 7
attgaagatg gaggcgttca actagca                                              27

<210> SEQ ID NO 8
<211> LENGTH: 33
<212> TYPE: DNA
<213> ORGANISM: Artificial Sequence
<220> FEATURE:
<223> OTHER INFORMATION: Tag

<400> SEQUENCE: 8
gatgaactat acaagcttat gtccagactt cca                                       33

<210> SEQ ID NO 9
<211> LENGTH: 27
<212> TYPE: DNA
<213> ORGANISM: Artificial Sequence
<220> FEATURE:
<223> OTHER INFORMATION: Tag

<400> SEQUENCE: 9
aagggcagat tggtaggaca ggtaatg                                              27

<210> SEQ ID NO 10
<211> LENGTH: 23
<212> TYPE: DNA
<213> ORGANISM: Artificial Sequence
<220> FEATURE:
<223> OTHER INFORMATION: Tag

<400> SEQUENCE: 10
ccgtcgggca tccgcgcctt gag                                                  23

<210> SEQ ID NO 11
<211> LENGTH: 33
<212> TYPE: DNA
<213> ORGANISM: Artificial Sequence
<220> FEATURE:
<223> OTHER INFORMATION: Tag

<400> SEQUENCE: 11
tacattgtgt gagttgaagt tgtattccaa ttt                                       33

<210> SEQ ID NO 12
<211> LENGTH: 95
<212> TYPE: DNA
<213> ORGANISM: Artificial Sequence
<220> FEATURE:
<223> OTHER INFORMATION: Sample tag

<400> SEQUENCE: 12
atttaggtga cactatagaa ctcgaccagt acattgtgtg agttgaagtt gtattccaat          60
ttctgaagct tgcatgcctg caggtcgact ctaga                                     95

<210> SEQ ID NO 13
<211> LENGTH: 13
<212> TYPE: DNA
<213> ORGANISM: Artificial Sequence
<220> FEATURE:
<223> OTHER INFORMATION: Vector polylinker
```

```
<400> SEQUENCE: 13
gatctgccgg tct                                                           13

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ggtgacacta tagaactcga gcag                                               24

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
caggcatgca agcttcag                                                      18

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cactatcgac tacgcgatca                                                    20

<210> SEQ ID NO 17
<211> LENGTH: 113
<212> TYPE: DNA
<213> ORGANISM: Artificial Sequence
<220> FEATURE:
<223> OTHER INFORMATION: Vector polylinker

<400> SEQUENCE: 17
gaattccatg ttgttggggc gcgcctccat caacgtggat ccatcgagac ggtccagagc        60
tcagtggcgc atgcaatgct ccaactgcag gttagccatg gttgcccaag ctt              113

<210> SEQ ID NO 18
<211> LENGTH: 12
<212> TYPE: DNA
<213> ORGANISM: Artificial Sequence
<220> FEATURE:
<223> OTHER INFORMATION: Adapter

<400> SEQUENCE: 18
tgagtcacca ac                                                            12

<210> SEQ ID NO 19
<211> LENGTH: 25
<212> TYPE: DNA
<213> ORGANISM: Artificial Sequence
<220> FEATURE:
<223> OTHER INFORMATION: Tag

<400> SEQUENCE: 19
tcaatcgact acactcgtaa caaga                                              25
```

```
<210> SEQ ID NO 20
<211> LENGTH: 25
<212> TYPE: DNA
<213> ORGANISM: Artificial Sequence
<220> FEATURE:
<223> OTHER INFORMATION: Tag

<400> SEQUENCE: 20
gatcaattcg ctaatcgatc gtata                                          25

<210> SEQ ID NO 21
<211> LENGTH: 25
<212> TYPE: DNA
<213> ORGANISM: Artificial Sequence
<220> FEATURE:
<223> OTHER INFORMATION: Tag

<400> SEQUENCE: 21
aaatagatcg cataagcagt acgtg                                          25

<210> SEQ ID NO 22
<211> LENGTH: 25
<212> TYPE: DNA
<213> ORGANISM: Artificial Sequence
<220> FEATURE:
<223> OTHER INFORMATION: Tag

<400> SEQUENCE: 22
tcataggctg acagtcctag ctagt                                          25

<210> SEQ ID NO 23
<211> LENGTH: 25
<212> TYPE: DNA
<213> ORGANISM: Artificial Sequence
<220> FEATURE:
<223> OTHER INFORMATION: Tag

<400> SEQUENCE: 23
tcgtagacag tacatgtcga tgaat                                          25

<210> SEQ ID NO 24
<211> LENGTH: 25
<212> TYPE: DNA
<213> ORGANISM: Artificial Sequence
<220> FEATURE:
<223> OTHER INFORMATION: Tag

<400> SEQUENCE: 24
taaccgatct agtcgatcta cgact                                          25

<210> SEQ ID NO 25
<211> LENGTH: 25
<212> TYPE: DNA
<213> ORGANISM: Artificial Sequence
<220> FEATURE:
<223> OTHER INFORMATION: Tag

<400> SEQUENCE: 25
gtttcgagct agctaagaga ctcgt                                          25

<210> SEQ ID NO 26
<211> LENGTH: 25
<212> TYPE: DNA
<213> ORGANISM: Artificial Sequence
<220> FEATURE:
<223> OTHER INFORMATION: Tag
```

-continued

```
<400> SEQUENCE: 26
cgtatttcga ctgactagcc tctag                                          25

<210> SEQ ID NO 27
<211> LENGTH: 25
<212> TYPE: DNA
<213> ORGANISM: Artificial Sequence
<220> FEATURE:
<223> OTHER INFORMATION: Tag

<400> SEQUENCE: 27
agttcgatca gctaactctg agtca                                          25

<210> SEQ ID NO 28
<211> LENGTH: 25
<212> TYPE: DNA
<213> ORGANISM: Artificial Sequence
<220> FEATURE:
<223> OTHER INFORMATION: Tag

<400> SEQUENCE: 28
gctatatcga tcgtccatta acgta                                          25

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
gggcaaccat ggctaacc                                                  18

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
ctgaatctta ccaacgctaa c                                              21

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
atccatcgag acggtcca                                                  18

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
caacgtggat ccatcgaga                                                 19

<210> SEQ ID NO 33
<211> LENGTH: 20
```

```
<212> TYPE: DNA
<213> ORGANISM: Artificial Sequence
<220> FEATURE:
<223> OTHER INFORMATION: Adapter

<400> SEQUENCE: 33
gctcattgcg gtagcatacc                                              20

<210> SEQ ID NO 34
<211> LENGTH: 10
<212> TYPE: DNA
<213> ORGANISM: Artificial Sequence
<220> FEATURE:
<223> OTHER INFORMATION: Adapter

<400> SEQUENCE: 34
ggtatgctac                                                         10

<210> SEQ ID NO 35
<211> LENGTH: 20
<212> TYPE: DNA
<213> ORGANISM: Artificial Sequence
<220> FEATURE:
<223> OTHER INFORMATION: Adapter

<400> SEQUENCE: 35
gcgtggccta ctacgattgt                                              20

<210> SEQ ID NO 36
<211> LENGTH: 10
<212> TYPE: DNA
<213> ORGANISM: Artificial Sequence
<220> FEATURE:
<223> OTHER INFORMATION: Adapter

<400> SEQUENCE: 36
tcaatcgtag                                                         10

<210> SEQ ID NO 37
<211> LENGTH: 20
<212> TYPE: DNA
<213> ORGANISM: Artificial Sequence
<220> FEATURE:
<223> OTHER INFORMATION: Adapter

<400> SEQUENCE: 37
gacgtagcga actagggcag                                              20

<210> SEQ ID NO 38
<211> LENGTH: 10
<212> TYPE: DNA
<213> ORGANISM: Artificial Sequence
<220> FEATURE:
<223> OTHER INFORMATION: Adapter

<400> SEQUENCE: 38
ctgccctagt                                                         10

<210> SEQ ID NO 39
<211> LENGTH: 20
<212> TYPE: DNA
<213> ORGANISM: Artificial Sequence
<220> FEATURE:
<223> OTHER INFORMATION: Adapter

<400> SEQUENCE: 39
```

-continued gcaagcagcc tacgcattat                                          20

<210> SEQ ID NO 40
<211> LENGTH: 10
<212> TYPE: DNA
<213> ORGANISM: Artificial Sequence
<220> FEATURE:
<223> OTHER INFORMATION: Polylinker

<400> SEQUENCE: 40
ataatgcgta                                                     10

<210> SEQ ID NO 41
<211> LENGTH: 41
<212> TYPE: DNA
<213> ORGANISM: Artificial Sequence
<220> FEATURE:
<223> OTHER INFORMATION: Polylinker

<400> SEQUENCE: 41
ggatccgcgg ccgcacgtga ctagcatggc ccgggcgatc c                  41

<210> SEQ ID NO 42
<211> LENGTH: 30
<212> TYPE: DNA
<213> ORGANISM: Artificial Sequence
<220> FEATURE:
<223> OTHER INFORMATION: Primer

<400> SEQUENCE: 42
gtcagcggcc gcatccatcg agacggtcca                               30

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
aattggaatc aataaagccc tgcg                                     24

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
acgactgtgc tggtcattaa ac                                       22

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
tgatgaatgt tccgttgcg                                           19

<210> SEQ ID NO 46
<211> LENGTH: 19
<212> TYPE: DNA
<213> ORGANISM: Artificial Sequence

```
<220> FEATURE:
<223> OTHER INFORMATION: Primer

<400> SEQUENCE: 46
cgtattcagg ctgaccctg                                              19

<210> SEQ ID NO 47
<211> LENGTH: 16
<212> TYPE: DNA
<213> ORGANISM: Artificial Sequence
<220> FEATURE:
<223> OTHER INFORMATION: Primer

<400> SEQUENCE: 47
cgctgcccgg attaca                                                 16

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
tgtaaaacga cggccagtg                                              19

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
caggaaacag ctatgaccat ga                                          22
```

APPLICATIONS OF PARALLEL GENOMIC ANALYSIS

1. RELATED APPLICATION DATA

The present application is a continuation-in-part of U.S. application Ser. No. 09/427,834 filed Oct. 26, 1999, now U.S. Pat. No. 6,480,791 which application is entirely incorporated herein by reference.

2. FIELD OF THE INVENTION

The present invention is related to the field of molecular biology, and provides parallel methods for nucleic acid sequencing, physical mapping and mapping insertion elements.

3. BACKGROUND

There are two methods in common use to sequence DNA: the chemical degradation method, e.g., Maxam et al., (1977) and the chain-termination method, e.g., Sanger et al., (1977). Efforts to improve DNA sequencing efficiency have resulted in numerous improvements in the chain-termination method. Automation of many steps in the process has produced significant improvements in sequencing throughput. Nevertheless, each template still is sequenced one at a time.

Attempts have been made to introduce some parallel processing steps into the sequencing method. For example Church (1990) and Church et al. (1992) teach a strategy in which multiple templates are fragmented in a single tube by either the chain-termination or chemical-degradation sequencing methods. The fragments are separated on a gel and transferred to a solid membrane. Each template carries a unique tag and the fragments are visualized by hybridization with a unique oligonucleotide probe specific to each tag. The pattern of the fragments that hybridize to one specific oligonucleotide probe represent the sequence information from one template. Removal of the first oligonucleotide probe followed by hybridization of a second oligonucleotide probe reveals the sequence pattern from a different template. This method is limited by the requirement to maintain the pattern of fragments in order to extract the sequence information. Therefore, only one sequence can be read at a time; that is, this step in the method is sequential rather than parallel. There are inherent time constraints produced by this sequential step. In addition, the number of times any membrane can be "stripped" and reprobed is limited. For these reasons, the application of the method is limited in practice to collections of fewer than 50 templates.

Other methods are described in the art which attempt to introduce parallelism into different stages of the sequencing protocol. Van Ness et al. (1997) describe the use of mass tags that can be detected by mass spectrometry. Different tags are attached to the 5'-end of a sequencing primer. Each tagged primer is used to sequence a different template by the chain-termination method. The different reactions are pooled and fractionated by size (i.e. sequencing products are collected from the end of a capillary electrophoresis device). The tags present in each fraction are assayed by mass spectrometry. This information is deconvoluted to reproduce the "sequence ladders" of the different templates. The method is limited by the number of different tags that can be synthesized. More importantly, the method is not parallel until the sequencing reactions are pooled.

A variation of the Van Ness method is described by Wong (1999). He replaces the chemical tags attached to the 5'-end of a primer with nucleic acid tags. Again, individual sequencing reactions are pooled and fractionated by size. Instead of detection by mass spectrometry, the tags in each fraction are designed to be amplified and labeled in vitro (i.e. PCR) followed by hybridization to an array of oligonucleotides. Individual locations in the array will hybridize to different tags. A positive hybridization signal indicates the tag is present in the fraction. This information is deconvoluted to reveal the sequence ladders of the different templates. The possible number of different tags attached to the sequencing primer is far greater with Wong's method than the Van Ness method. However, Wong still describes a method that is not parallel until the sequencing reactions are pooled. Consequently, much of the labor associated with traditional sequencing protocols still is present in Wong's method. DNA must be prepared from individual clones, and separate sequencing reactions must be performed on each template. In a second embodiment, Wong attempts to introduce some parallelism into these steps. He attaches the tags to several different sequencing primers. The different primers hybridize to different vectors. Instead of sequencing one clone at a time, he makes separate libraries in each vector, pools one clone from each library and sequences them with the pooled primers. The sequencing products from different pools are then combined and fractionated by size. Each clone still requires its own uniquely tagged primer, but fewer sequencing reactions are needed. In theory, this same strategy can be applied to the Van Ness mass-tag method, as described by Schmidt et al. (1999). Presumably, the strategy will work for very small pools of primers, but as the collection of primers and vectors increases, mispriming events and failed sequences will predominate. In addition, single clones still are handled one at a time so considerable resources must be dedicated simply to producing, cataloging and storing the sequencing templates.

Rabani (1996 and 1997) describes a sequencing method that employs the same tagged sequencing vectors used by Church (1990). A pool of templates with substantially different tags is sequenced with one primer as described in the Church patent. A label is incorporated into either the primer or the chain-terminator. The sequencing products are fractionated by size and immediately hybridized to an array of oligonucleotides (analogous to the array in Wong's method). Detection of the label at a particular location in the array indicates the presence of that tag in the fraction. The sequence ladders are deconvoluted as above. Though parallel at each step, in practice only a small number of samples can be pooled. A small amount of labeled material is available in each fraction for hybridization to the array. This material will determine the rate of hybridization and limits of detection. A very sensitive oligonucleotide array can detect about 0.1 femtomoles of a complementary polynucleotide, see Lockhart et al. (1996). Assuming each tag is present in about 1000 bands of a sequencing ladder, then at least 0.1 picomoles of any tagged clone must be present in the pool before sequencing. A typical sequencing reaction uses about 0.5 picomoles DNA. This calculation suggests a starting pool of about five clones may be sequenced according to Rabani's method.

Thus, there is a need in the art for a highly parallel sequencing method that is not limited by any sequential "bottlenecks" described above. The sequencing method would result in significant improvements in sequencing throughput and substantial reductions in the cost of sequencing.

To sequence very large genomes, the DNA first must be broken down into smaller, more manageable clones. The determination of the overlap relationships of these smaller clones is needed to simplify the reconstruction of the entire sequence. The method most frequently used is "Sequence Tagged Site" (STS) content mapping. This method involves finding many small regions of single copy DNA (i.e., STS's) and determining which clones contain the same STS's. Two clones that contain the same STS must overlap. Detection of the STS is achieved by amplifying pools of clones with the polymerase chain reaction. This mapping process is very expensive and time consuming.

Ultimately, the physical mapping and sequencing of organisms is designed to hasten the discovery of gene function. A general step in this process is to observe the phenotype of the null mutant. Through "reverse genetics" it is possible to "knockout" the function of a cloned gene to produce the null phenotype. Usually, gene knockouts are produced one at a time at great expense by introducing foreign DNA into the gene. Even efforts to apply reverse genetics to many cloned genes simply scale up the serial one-by-one approach.

For these reasons, there is a need in the art for a method that introduces massive parallelism into the processes of sequencing, physical mapping and the production of gene knockouts. The present invention provides these and other advantages, as described in greater detail below.

4. BRIEF DESCRIPTION OF THE FIGURES

5. SUMMARY

Figure 1A:
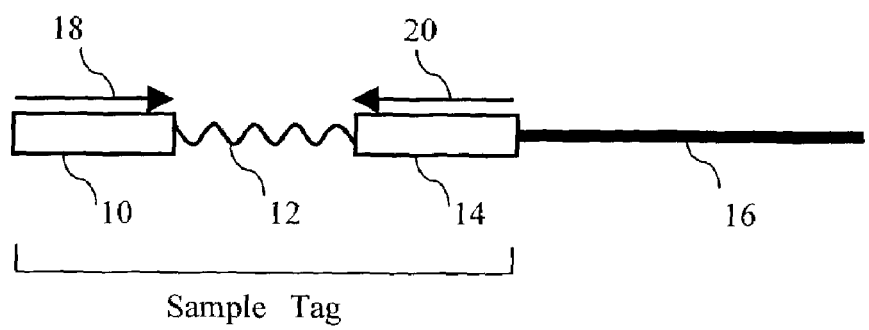
FIG. 1a is a drawing of a preferred embodiment of a sample tag joined to a sample polynucleotide.

It is an object of the invention to provide massively parallel methods for generating nucleic acid sequence information from a collection of polynucleotides. More specifically, the method employs Sanger or Maxam and Gilbert nucleic acid sequencing reactions carried out on a collection of sample polynucleotides cloned into sample-tagged vectors so that a sample tag preferably is joined to one sample polynucleotide. The sample tags are used to deconvolute the sequence information derived from the different sample polynucleotides. Deconvolution is achieved through hybridization of size-separated products from the sequencing reaction to an array of tag complements.

It is another object of the invention to provide a kit for carrying out the disclosed massively parallel sequencing methods. The kit preferably contains a library of sample-tagged cloning vectors in which the target nucleic acid whose sequence is sought may be cloned, enzymes for cloning the target into the cloning vectors, reagents for carrying out the sequencing reactions, reagents for amplifying the sample tags, an array of tag complements, and instructions for carrying out the method.

It is a further object of the invention to provide methods and kits for carrying out the disclosed methods of physical mapping and generating gene knockouts. These methods and kits are based upon the reagents and principles analogous to those used for the massively parallel sequencing methods, as described below.

6. DETAILED DESCRIPTION OF PREFERRED EMBODIMENTS

6.1 Definitions

A "sequence element" or "element" as used herein in reference to a polynucleotide is a number of contiguous bases or base pairs in the polynucleotide, up to and including the complete polynucleotide. When referring to a sequence element with a particular property, the sequence element consists of the bases or base pairs that contribute to the property or are defined by the property.

The term "sample" as used herein refers to a polynucleotide or that element of a polynucleotide which will be analyzed for some property according to the method of this invention. For example, a sample polynucleotide may be joined to other sequence elements to form a larger polynucleotide in order to practice the invention. The element of the larger polynucleotide that is homologous to the sample polynucleotide is the "sample element" or "sample sequence element".

A "sample tag" refers to a sequence element used to identify or distinguish different sample polynucleotides, sequence elements or clones present as members of a collection. In general, an individual sample tag is joined to an individual polynucleotide resulting in a collection of "sample-tagged" polynucleotides comprising distinct sample tags. A sample-tagged polynucleotide may comprise one or more distinct sample tags, which are used to distinguish different segments of the polynucleotide. For example, sample tags may be present at the 5' and 3' ends of the polynucleotide, or different tags may be distributed at multiple sites in the polynucleotide. The same sample polynucleotide may be associated with more than one sample tag, but to be informative, one sample tag must be associated with only one sample polynucleotide in a collection. It is these informative associations that constitute sample-tagged clones. Methods for designing sample tags are well known in the art as exemplified by, e.g., Brenner (1997b). In some embodiments of the invention, the sample tags may comprise individual synthetic oligonucleotides each of which has been ligated into a vector, to provide a library or collection of vectors with distinct sample tags or the oligonucleotides are ligated directly to the polynucleotides to be analyzed. In other embodiments, the sample tag may comprise part of the sample sequence element.

"Tagged" as used herein in reference to a polynucleotide means the polynucleotide is derived in one or more steps from a sample-tagged polynucleotide by for example enzymatic, chemical or mechanical means, and the polynucleotide comprises a tag. The "tag" is a sequence element that corresponds to a sample tag and can be used to identify or distinguish the sample tag. Note a sequence element is itself a tag if it is derived from a tag and can be used to identify or distinguish the tag. In many embodiments, the tag and the sample tag are identical. In certain embodiments, the tag comprises the sample tag but contains additional sequence elements. The additional sequence elements may be necessary for example to permit increased hybridization temperatures or to impose structural constraints on the tag. In other embodiments, the sample tag comprises the tag but contains additional sequence elements. For example, two different sample tags that share the same tag may be distinguished by preferential PCR amplification of the tag with primers that are specific to only one tag. Subsequent removal of the priming sequences produces identical tags that can be used to distinguish the different sample tags. During amplification or another step in the invention, the tag could lose all sequence identity with the sample tag. Nevertheless, as long as there exists an identifiable correspondence between the two, information associated with the tag can be related to the sample tag which in turn can be related to the sample polynucleotide. The number of distinct tags required to characterize a collection of sample-tagged polynucleotides will vary. In some embodiments, a one-to-one relationship exists between the tag and the sample tag. In other embodiments, the tags will identify information in addition to the sample identity, for example the terminating nucleotide, the restriction site, etc. Consequently, more distinct tags than distinct sample tags may be used. Finally as outlined above, the same tag may be used to identify more than one sample tag.

A "tag complement" as used herein refers to a molecule that will substantially hybridize to only one tag, or a set of distinguishable tags, among a collection of tags under the appropriate conditions. Different tags that hybridize to the same tag complement may be distinguished for example by different fluorophores, by their ability to hybridize to a second oligonucleotide, etc. Some degree of cross-hybridization by otherwise distinguishable tags can be tolerated, provided the signal arising from hybridization between a tag A and its tag complement A' is discernable from the cross-hybridization signal arising from hybridization between a different tag B and the tag complement A'. In embodiments where the tag complement is a polynucleotide or sequence element, preferably the tag is perfectly matched to the tag complement. In embodiments where specific hybridization results in a triplex, the tag may be selected to be either double stranded or single stranded. Thus, where triplexes are formed, the term "complement" is meant to encompass either a double stranded complement of a single stranded tag or a single stranded complement of a double stranded tag. Tag complements need not be polynucleotides. For example, RNA and single-stranded DNA are known to adopt sequence dependent conformations and will specifically bind to polypeptides and other molecules (Gold et al., 1993 & 1995).

The terms "oligonucleotide" or "polynucleotide" as used herein include linear oligomers of natural or modified monomers or linkages, including deoxyribonucleosides, ribonucleosides, 1-anomeric forms thereof, peptide nucleic acids (PNAs), and the like, capable of specifically binding under the appropriate conditions to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form "oligonucleotides" ranging in size from a few monomeric units, e.g., 3-4, to several tens of monomeric units, and "polynucleotides" are larger. However the usage of the terms "oligonucleotides" and "polynucleotides" in the art overlaps and varies. The terms are used interchangeably herein. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. It is clear to those skilled in the art when polynucleotides having natural or non-natural nucleotides may be employed. Polynucleotides or oligonucleotides can be single-stranded or double-stranded.

As used herein, the term "polypeptide" is intended to include compounds composed of amino acid residues linked by amide bonds. Although "protein" is often used in reference to relatively large polypeptides, and "peptide" is often used in reference to small polypeptides, usage of these terms in the art overlaps and varies. The term "polypeptide" as used herein thus refers interchangeably to peptides, polypeptides and proteins, unless otherwise noted or clear from the context. The term "polypeptide" is further intended to encompass polypeptide analogues, polypeptide derivatives and peptidomimetics that mimic the chemical structure of a polypeptide composed of naturally-occurring amino acids. Thus a "polypeptide" encoded in a polynucleotide is meant to include the polypeptide determined by the genetic code and these synthetic mimics. Examples of polypeptide analogues include polypeptides comprising one or more non-natural amino acids. Examples of polypeptide derivatives include polypeptides in which an amino acid side chain, the polypeptide backbone, or the amino- or carboxy-terminus has been derivatized (e.g., peptidic compounds with methylated amide linkages). Examples of peptidomimetics include peptidic compounds in which the polypeptide backbone is substituted with one or more benzodiazepine molecules (see e.g., James, et al., 1993), "inverso" polypeptides in which all L-amino acids are substituted with the corresponding D-amino acids, "retro-inverso" polypeptides (see, Sisto et al., 1985) in which the sequence of amino acids is reversed ("retro") and all L-amino acids are replaced with D-amino acids ("inverso") and other isosteres, such as polypeptide back-bone (i.e., amide bond) mimetics, including modifications of the amide nitrogen, the α-carbon, amide carbonyl, complete replacement of the amide bond, extensions, deletions or backbone crosslinks. Several peptide backbone modifications are known, including $\psi[CH_2S]\psi$, $\psi[CH_2NH]$, $\psi[CSNH_2]$, $\psi[NHCO]$, $\psi[COCH_2]$, and $\psi[(E)$ or $(Z)$ $CH=CH]$. In the nomenclature used above, $\psi$ indicates the absence of an amide bond. The structure that replaces the amide group is specified within the brackets. Other possible modifications include an N-alkyl (or aryl) substitution ($\psi[CONR]$), backbone crosslinking to construct lactams and other cyclic structures, and other derivatives including C-terminal hydroxymethyl derivatives, O-modified derivatives and N-terminally modified derivatives including substituted amides such as alkylamides and hydrazides.

"Perfectly matched" or "perfectly complementary" in reference to a duplex means that the poly- or oligonucleotide strands making up the duplex form a double stranded structure with one another such that every nucleotide in each strand undergoes Watson-Crick base pairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a base pair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" and "nucleotide" include the natural nucleosides and nucleotides, including 2'-deoxy and 2'-hydroxyl forms, e.g., as described in Kornberg et al. (1992). "Natural nucleotide" as used herein refers to the four common natural deoxynucleotides A, C, G, and T. "Analogs" in reference to nucleosides includes synthetic nucleosides having modified base moieties and/or modified sugar moieties, e.g., described by Scheit (1980); Uhlman et al. (1990), or the like, with the only proviso that they are capable of specific hybridization. Such analogs include synthetic nucleosides designed to enhance binding properties, reduce complexity of probes, increase specificity, and the like.

As used herein, "nucleic acid sequencing reaction" refers to a reaction that carried out on a polynucleotide clone will produce a collection of polynucleotides of differing chain length from which the sequence of the original nucleic acid can be determined. The term encompasses, e.g., methods commonly referred to as "Sanger Sequencing," which uses dideoxy chain terminators to produce the collection of polynucleotides of differing length and variants such as "Thermal Cycle Sequencing", "Solid Phase Sequencing," exonuclease methods, and methods that use chemical cleavage to produce the collection of polynucleotides of differing length, such as Maxam-Gilbert and phosphothioate sequencing. These methods are well known in the art and are described in, e.g., Ausubel, et al. (1997); Gish et al. (1988); Sorge et al. (1989); Li et al (1993); Porter et al. (1997). The term also includes methods based on termination of RNA polymerase (e.g., Axelrod et al., 1978).

A "sequencing method" is a broad term that encompasses any reaction carried out on a polynucleotide to determine some sequence from the polynucleotide. The term encompasses nucleic acid sequencing reactions, sequencing by hybridization (Southern, 1997; Drmanac et al., 1993; Khrapko et al., 1996; Fodor et al., 1999), step-wise sequencing (e.g. Cheeseman, 1994; Rosenthal, 1993; Brenner, 1998a), etc.

A "sequence ladder" refers to a pattern of fragments from one clone resulting from the size separation and visualization of reaction products produced by a "nucleic acid sequencing reaction." Typically, size separation is accomplished by denaturing gel electrophoresis. The nucleic acid sequence is ascertained by interpreting the "sequence ladder" to determine the identity of the 3' terminal nucleotides of reaction products that differ in length by one nucleotide. Generating and interpreting "sequence ladders" is well within the skill in the art, and is described in, e.g. Ausubel et al. (1997). A "band" in a sequence ladder refers to the clonal population of reaction products that terminate at the same base and so migrate together through the separation medium. A band will have width due to dispersion and diffusion, so it is possible to speak of a part or portion of a band, which means a collection of the clonal population that has migrated more closely together than some other collection.

A "primer" is a molecule that binds to a polynucleotide and enables a polymerase to begin synthesis of the daughter strand. For example, a primer can be a short oligonucleotide, a tRNA (e.g. Panet et al., 1975) or a polypeptide (e.g. Guggenheimer et al., 1984). A "primer binding site" is the sequence element to which the primer binds.

A "sequencing primer" is an oligonucleotide that is hybridized to a polynucleotide clone to prime a nucleic acid sequencing reaction. The sequencing primer is prepared separately, usually on a DNA synthesizer and then combined with the polynucleotide. A "sequencing primer binding site" is the sequence element to which the sequencing primer hybridizes. The sequencing primer binding sites in two different polynucleotides are considered to be the same when the same sequencing primer will efficiently prime the nucleic acid sequencing reaction for both polynucleotides. Of course, mispriming frequently occurs during sequencing reactions, but these artifactual priming sites are minor components of the sequencing reaction products. One skilled in the art will readily understand the difference between mispriming and efficient priming at the sequencing primer binding site.

"Deconvoluting" means separating data derived from a plurality of different polynucleotides into component parts, wherein each component represents data derived from one of the polynucleotides comprising the plurality.

An "array" refers to a solid support that provides a plurality of spatially addressable locations, referred to herein as features, at which molecules may be bound. The number of different kinds of molecules bound at one feature is small relative to the total number of different kinds of molecules in the array. In many embodiments, only one kind of molecule (e.g. oligonucleotide) is bound at each feature. Similarly, "to array" a collection of molecules means to form an array of the molecules.

"Spatially addressable" means that the location of a molecule bound to the array can be recorded and tracked throughout any of the procedures carried out according to the method of the invention.

A "particulate array" is an array wherein the solid support comprises particles. A particle may comprise one or more features. The particles may be fixed relative to one another or their relative positions may vary with time (e.g. particles in solution). A particle may possess a detectable property (e.g., a transponder) in which case the spatial address of a molecule bound to the array may be determined for example by passing the particle through a detector that identifies both the particle and the molecule (see for example Mandecki (1997) and Mandecki (2002)).

A "contig" means a group of clones that represent overlapping regions of a genome.

A "contig map" means a map depicting the relative order of a linked library of small overlapping clones representing a complete chromosomal segment.

A "library" refers to a collection of polynucleotides. A particular library might include, for example, clones of all of the DNA sequences expressed in a certain kind of cell, or in a certain organ of the body, or a collection of man-made polynucleotides, or a collection of polynucleotides comprising combinations of naturally-occurring and man-made sequences. Polynucleotides in the library may be spatially separated, for example one clone per well of a microtiter plate, or the library may comprise a pool of polynucleotides or clones. When a reaction is performed on a spatially separated library, the same reaction by definition must be performed separately on every member of the library. When a reaction is performed on a pooled library, the reaction need only be performed once.

"Physical mapping" broadly refers to determining the locations of two or more landmarks in a polynucleotide segment. The term is meant to distinguish genetic mapping methods, which rely on a determination of recombination frequencies to estimate distance between two or more landmarks, from the methods of the present invention, which determine the actual linear distance between landmarks. Similarly, a "physical map" is the product of physical mapping.

"Landmark" broadly refers to any distinguishable feature in a polynucleotide other than an unmodified nucleotide. Landmarks include, by way of example, restriction sites, single nucleotide polymorphisms, short sequence elements recognized by nucleic acid binding molecules, DNase hypersensitive sites, methylation sites, transposon, etc. This definition is meant to distinguish physical mapping from "sequencing", which refers to determining the linear order of nucleotides in a polynucleotide.

"Fingerprinting" refers to the use of physical mapping data to determine which nucleic acid fragments have a specific sequence (fingerprint) in common and therefore overlap.

"Cloning" as used herein in reference to a polynucleotide refers to any method used to replicate a polynucleotide segment. The term encompasses cloning in vivo, which makes use of a cloning vector to carry inserts of the polynucleotide segment of interest, and what I refer to as cloning in vitro in which one or both strands of a polynucleotide segment of interest is replicated without the use of a vector. Cloning in vitro encompasses, for example, replication of a polynucleotide segment using PCR, linear amplification using a primer that recognizes a portion of the polynucleotide segment in conjunction with an enzyme capable of replicating the polynucleotide, in-vitro transcription, rolling circle replication, etc. Similarly, a "clone" in reference to a polynucleotide means a polynucleotide that has been replicated to produce a population of polynucleotides or sequence elements that share identical or substantially identical sequence. Substantial identity encompasses variations in the sequence of a polynucleotide that sometimes are introduced during PCR or other replication methods. This notion of substantial identity is well understood by those skilled in the art and it applies whenever the identity of polynucleotides is at issue.

"Hybridization" as used herein refers to a sequence dependent binding interaction between at least one strand of a polynucleotide and another molecule. From the context, it is obvious to one skilled in the art whether a double-stranded polynucleotide must be denatured before the binding event. For example, the term includes Watson-Crick type base pairing, Hoogsteen and reverse Hoogsteen bonding, binding of an aptamer to its cognate molecule, etc. "Cross-hybridization" occurs when two distinct polynucleotides can bind to the same molecule or two distinct molecules can bind to the same polynucleotide. In general, cross-hybridization depends on the collection of polynucleotides (or molecules) since two polynucleotides (or molecules) cannot cross-hybridize if they are not in the same collection. Hybridization and cross-hybridization also may be used in reference to sequence elements. For example, two distinct polynucleotides may contain identical sample tags. The polynucleotides cross-hybridize to the tag complement whereas the tags, being identical, do not cross hybridize.

A "common sequence" or "common sequence element" refers to a sequence or sequence element that is or is intended to be present in every member of a collection of polynucleotides.

The term "distinct" as used herein in reference to polynucleotides or sequence elements means that the sequences of the polynucleotides or sequence elements are not identical, A "pool" is a group of different molecules or objects that is combined together so that they are not isolated from one another and any operation performed on one member of the pool is by necessity performed on many members of the pool. For example, a pool of polynucleotides in solution is simply a plurality of different polynucleotides or clones mixed together in one solution; or each clone may be attached to a solid support, for example an array or a bead, in which case the pool consists of the clones combined together in one solution (e.g., the same fluid container). Similarly, "to pool" means to form a pool.

An "aliquot" is a subdivision of a sample such that the composition of the aliquot is essentially identical to the composition of the sample.

The term "to derive" as used herein in reference to polynucleotides means to generate one polynucleotide from another by any process, for example enzymatic, chemical or mechanical. The generated polynucleotide is "derived" from the other polynucleotide.

The term "amplify" in reference to a polynucleotide means to use any method to produce multiple copies of a polynucleotide segment, called the "amplicon", by replicating a sequence element from the polynucleotide or by deriving a second polynucleotide from the first polynucleotide and replicating a sequence element from the second polynucleotide. The copies of the amplicon may exist as separate polynucleotides or one polynucleotide may comprise several copies of the amplicon. A polynucleotide may be amplified by, for example a polymerase chain reaction, in vitro transcription, rolling-circle replication, in vivo replication, etc. Frequently, the term "amplify" is used in reference to a sequence element in the amplicon. For example, one may refer to amplifying the tag in a polynucleotide by which is meant amplifying the polynucleotide to produce an amplicon comprising the tag sequence element. The precise usage of amplify is clear from the context to one skilled in the art.

The term "cleave" as used herein in reference to a polynucleotide means to perform a process that produces a smaller fragment of the polynucleotide. If the polynucleotide is double-stranded, only one of the strands may contribute to the smaller fragment. For example, physical shearing, endonucleases, exonucleases, polymerases, recombinases, topoisomerases, etc. will cleave a polynucleotide under the appropriate conditions. A "cleavage reaction" is the process by which a polynucleotide is cleaved.

A "mapping reaction" as used herein refers to any reaction that can be carried out on a polynucleotide clone to generate a physical map or a nucleotide sequence of the clone. Similarly, a "map" is a physical map or a nucleotide sequence.

The term "associating" as used herein in reference to a tagged polynucleotide with a property and a tag complement means determining that the polynucleotide hybridizes to the tag complement. In many embodiments, associating simply means hybridizing a polynucleotide with a known property to a tag complement and detecting the hybridization. In other embodiments, associating means detecting a property of a polynucleotide that is already hybridized to a tag complement. In both cases, the result is information that the polynucleotide has a certain property and in addition hybridizes to the tag complement. The properties of a polynucleotide can include for example the length, terminal base, terminal landmark or other properties according to this invention.

A "junction" as used herein in reference to insertion elements is the DNA that flanks one side of the insertion element.

A "clonal population" as used herein in reference to cells is a collection of cells that are substantially identical and originated from a single, isolated cell.

An "array sequencing reaction" is any method that is used to determine sequences from a plurality of polynucleotides in an array, for example methods described by Brenner (1997c and 1998a), Brenner et al. (1998a), Cheeseman (1994), Drmanac et al. (1993), Pastinen et al. (1997), Dubiley et al. (1997), Graber et al. (1999), etc.

A "bioactive" compound is any compound, either manmade or natural, that has an observable effect on a cell or organism. The observable effect is the "biological activity" of the compound.

A "daughter cell" as used herein in reference to a first cell is any descendent cell resulting from replication of the DNA of the first cell. The DNA of the daughter cell may not be identical to the first cell. For example, the daughter cell may result from mating two different cells (or organisms); additional DNA (for example transgenic DNA) or deletions may be present in the daughter cell; or the genome of the daughter cell may result from targeted homologous recombination, etc.

6.2 Massively-Parallel Sequencing Methods

A collection of sample-tagged clones is prepared by joining a set of sample polynucleotides with a set of sample tags so that many of the sample tags (i.e., preferably, at least approximately 35% of the total) are associated with unique sample polynucleotides. A preferred sample tag, as shown in FIG. 1a, comprises a distinct sequence element 12 flanked on both sides by common regions 10 & 14 shared by the other clones. The sample sequence element 16 comprises the sample polynucleotide that is joined to the sample tag. A nucleic acid sequencing reaction is performed on the pooled collection of sample-tagged clones (i.e., Sanger chain-termination method, Maxam & Gilbert chemical cleavage method, etc.) Typically, four separate reactions are performed, which correspond to the four (A, T, G, C) nucleotides. The Sanger method employs the sequencing primer 18, which hybridizes to the sequencing primer binding site in common region 10. In this example, only one sequencing primer binding site is needed for the sequencing reaction to be performed on the pool of sample-tagged clones. Of course, different collections of clones with different common regions comprising different sequencing primer binding sites may be pooled and more than one primer may be utilized, but preferably there will be many more sample-tagged clones than sequencing primer binding sites utilized in the sequencing reaction. One or a limited number of primer binding sites means only a small number of sequencing primers are required for the sequencing reaction, which produces efficient priming and limits spurious priming artifacts.

The products of the sequencing reactions are separated by size and four sets of fractions are collected. Any method of separation may be used that sufficiently resolves the sequencing fragments (i.e. single nucleotide resolution) and permits collection of the fragments in a state compatible with subsequent analysis (i.e. amplification and/or hybridization, see below). Representative methods include polyacrylamide gel electrophoresis, capillary electrophoresis, chromatography, etc. These methods are well known in the art and are described in, e.g. Ausubel et al. (1997), Landers (1996), and Thayer et al. (1996). Fractions may be collected, for example, by running the sequencing reactions off the bottom of a gel or column, or each lane of a gel may be sectioned in the direction normal to the direction of electrophoresis (i.e., transversely) and nucleic acid eluted from the sections. Ideally, each fraction corresponds to chain lengths that differ by one nucleotide and any one band is completely contained in only one fraction. Different clones however will display slight variations in band migrations, so fractions may contain only part of a band. Each fraction of terminated DNA fragments is made double-stranded using primer 20 in FIG. 1a, which hybridizes to common region 14. The fractions are amplified to produce tagged amplicons comprising distinct sequence element 12. A preferred method of amplification is PCR with primer 18 and primer 20. Other methods of amplification are applicable as described below. The four sets of amplicons can be marked with four different labels (e.g., four different fluorophores), where each label corresponds to one of the terminating nucleotides.

The amplicons are separately hybridized to an array of tag complements wherein for example each feature consists of oligonucleotides complementary to only one distinct sequence element 12. Alternatively, groups of four fractions that are marked with different labels and correspond to the same size (i.e. the same distance or time of migration), are pooled and hybridized to the array. For each tag, the hybridization patterns and fraction numbers will identify the sequence of nucleotides in the polynucleotide joined to that tag. That is, the sequencing ladder for the sample-tagged polynucleotide can be reconstructed from the hybridization data and fraction numbers for the associated tag. The resolution of the sequencing ladders will improve with more fractions per band (i.e. smaller fraction size), but the tradeoff is that more hybridizations are needed to reconstruct the ladders Obviously, hybridization conditions and tag sequences must be chosen to minimize cross-hybridization between different tags. Methods for designing sample tags are well known, see for example, Brenner (1997b). In this way, an array of oligos can be used to deconvolute sequences of the sample-tagged polynucleotides.

Figure 1B:
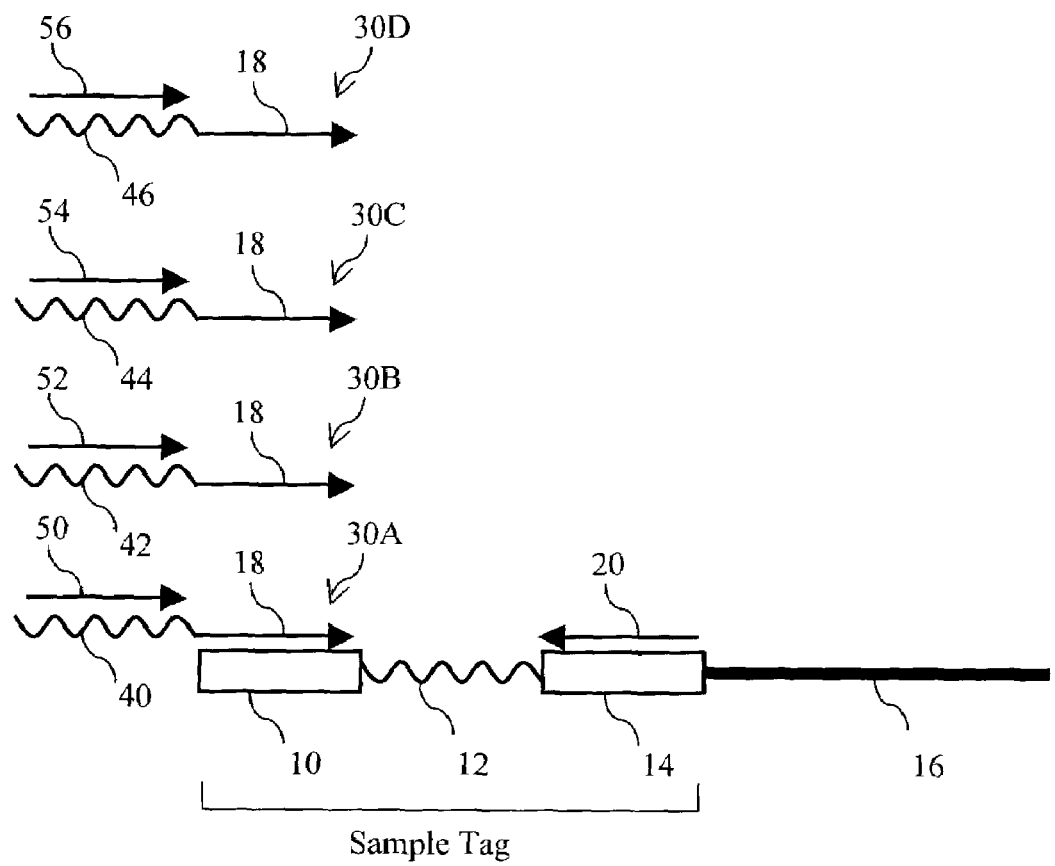
FIG. 1b is a drawing of a preferred embodiment of sequencing primers and amplification primers for preparing and analyzing sequencing reaction products that are pooled prior to fractionation.

A slight variation of the above technique will permit the four sequencing reactions to be run together in one lane. Thus, problems associated with lane-to-lane variation during gel electrophoresis are eliminated. The sequencing primer 18 can tolerate additional sequences at its 5'-end without influencing priming. Consider four different sequences of identical length (40, 42, 44 and 46) added to the 5'-end of primer 18 to make sequencing primers 30A, 30B, 30C and 30D as shown in FIG. 1b. The additional sequences are long enough so that their complements can act as primer binding sites for primers 50, 52, 54 and 56. Preferably the melting temperatures of these four primers are similar. Now, the four chain-terminating reactions are performed with the four different sequencing primers (i.e., ddATP reaction is primed by 30A, ddGTP is primed by 30B, etc.) The four reactions are pooled, separated by size and fractionated. Each fraction can be PCR amplified using five primers: 20, 50, 52, 54, and 56. Primers 50, 52, 54 and 56 are attached to different labels (i.e., different fluorophores). In this way, the tag is labeled according to the dideoxy terminator. Alternatively, each fraction can be amplified in four separate reactions with four primer pairs: 20+50, 20+52, 20+54, and 20+56, in which case the label need not be attached to the oligo. If RNA polymerase is used to amplify the tags, then sequences 40, 42, 44 and 46 may encode four separate RNA polymerase promoters (e.g., T3, T7, SP6 & *E. coli* RNA polymerase). Alternatively, the four sequencing primers (30A, 30B, 30C and 30D) may comprise a single promoter located 5-prime to regions 40, 42, 44 and 46. In the latter case, the tags may be visualized after hybridization to the array in a subsequent hybridization with labeled oligonucleotides 50, 52, 54 and 56, wherein the oligonucleotides preferably comprise different labels. If PCR is used to amplify the tags, it is advantageous to attach a biotin (or analogous) group to primer 20 (or the primers opposite primer 20) so the complementary (and in some cases unlabeled) strand can be easily removed before hybridization to the array. Other methods that preferentially degrade one strand can also be employed (e.g., 5'-phosphate plus lambda exonuclease, see Ausubel, 1997). Not all sequences of equal length will work equally well for the sequence elements 40, 42, 44 and 46. Preferably, the sequencing primers 30A, 30B, 30C and 30D have minimal secondary structure so their contribution to the mobility of the reaction products during separation is based essentially entirely on length, that is the different primers contribute equally to mobility.

An analogous strategy can be employed to permit pooling of nucleic acid sequencing products generated by the Maxam-Gilbert method (and other chemical cleavage methods). In this case, sequence elements that correspond to 40, 42, 44 and 46 are ligated as adapters to the sample-tagged polynucleotides before or after the reactions, but prior to pooling and separation. That is, the adapter comprising sequence 40 is ligated to polynucleotides subjected to the "A+G" reaction, the adapter comprising sequence 42 is ligated to polynucleotides subjected to the "G" reaction, etc.

Clearly, many different nucleic acid sequencing reactions can be used to practice this invention. The Sanger and Maxam-Gilbert methods are outlined above, but several variations are well known in the art.

By including polynucleotides of known sequence attached to known sample tags as internal controls in the pool of sample-tagged polynucleotides, it is possible to determine the fraction number of any fraction based on the known sequence information of the controls. That is, the control sequence patterns and signal intensities can be used to calibrate the hybridization patterns from the array to facilitate reconstruction of the unknown sequencing ladders. Any variation in signal intensities from one hybridization to the next can be calculated and corrected by referring to the control sequence patterns. If 10 known fragments are included in the pool, then each fraction will show only one of $4^{10}$≈one million possible hybridization patterns at the corresponding 10 locations on the array. In practice, this number is much greater because the hybridization signals will not have simple binary contributions from each base, but will display variable intensity depending on the amount of each band in the fraction.

Denaturing polyacrylamide gels separate DNA principally by size. There are well known exceptions to this rule (e.g., compressions) that can affect DNA migration. In addition, there is a very slight dependence of mobility on the terminal 3'-base. Therefore, sequencing bands corresponding to equivalent sizes need not be perfectly superimposed. The problem of reconstructing the DNA ladder from the band intensities in each fraction becomes a problem of reconstructing a wave from sampled intervals along that wave (picture the readout from an ABI sequencer and this problem becomes clear). Obviously, the more fractions that one collects, the more information one has to reconstruct the parent wave. This is simply a problem in information theory, well known in the art, see for example Stockham et al. (1993), Allison et al. (1998), Fujiwara et al (1982), Johnson et al. (1994), and Press et al. (1988). By calibrating the fractionation apparatus and/or using internal standards, the appropriate sampling frequency is determined. The hybridization data provides information about the "amplitude" of each peak. By optimizing the gel conditions and stressing uniform band intensities and uniform spacing, it may be possible to obtain unambiguous sequence data with fewer fractions than bases. Very few template preparations and sequencing reactions are needed to obtain enormous amounts of sequence information so even elaborate protocols (e.g., cesium banding, formamide gels, etc.) and a variety of nucleotide analogs (e.g. 7-deaza-dGTP and dITP) can be used to produce optimally fractionated sequencing products.

An important aspect of the method, is the ability to construct the clone libraries in a pool of sample tagged vectors (alternatively, the sample tags can be added as adapters and the clones ligated into the same vector, see Sagner et al., 1998). This approach greatly reduces the effort involved in library construction, but comes at a cost of lost information per pool. For example, consider a library that consists of 500,000 different sample tags. The effort would be enormous to make 500,000 separate libraries and then to pick a single clone from each library. Instead, one library is constructed and about 500,000 transformants are pooled (a very trivial operation). Similarly, the library may be constructed entirely in vitro, and 500,000 clones may be selected by amplifying in vitro a proper dilution of the library so that the amplicons comprise about 500,000 clones. However assuming a normal distribution, only a fraction (1/e=0.37) of the sample tags is expected to be present only once in the library (i.e. attached to only one sample polynucleotide). 37% of the sample tags are expected to be absent from the collection and the remainder will be present two or more times (that is, two or more different polynucleotide clones will contain the same sample tag). Therefore, 63% of the original sample tags will provide no or garbled information. Those original sample tags providing garbled information are readily recognized because more than a single base is identified at each position during the deconvolution step. This loss is well worth the savings in effort. Certain strategies can be used to increase the information content, such as using 5 million original sample tags and selecting only 500,000 clones, but if the maximum size of the array is 500,000 (close to the current Affymetrix array size), then either 10 arrays must be used per hybridization to extract about 90% of the information, or the subset of tags must be determined first and a new array synthesized that contains the 450,000 unique sample tags. It may be possible to enrich for unique clones by sequentially hybridizing to the array plasmid DNA from smaller subsets of transformants (say 50,000). In this way, a tag complement in the array becomes saturated and cannot hybridize to other plasmids that are present in subsequent pools. Plasmid DNA can be eluted from the array, transformed back into *E. coli* (or amplified in some other way) and sequenced. Of course, if smaller numbers of clones are to be sequenced, it is feasible to construct separate libraries for each tag and pool one member from each library before performing the sequencing reaction, or even separately perform the sequencing reaction on one member from each library and then pool the reaction products.

Another important aspect of the invention is the ability to amplify the DNA in the fractions. The current limit of detection on an Affymetrix chip is 0.5 pM probe (see Lockhart et al., 1996). Assuming a 200 μl hybridization volume, this equals $(0.5 \times 10^{-12} M) \times (200 \times 10^{-6} L) \times (6 \times 10^{23}$ molecules/mole$) = 6 \times 10^7$ molecules. Assuming 1 μg of 3 kb plasmid pool is sequenced, then $(10^{-6} g/(3000 \times 625 M.W.)) \times (6 \times 10^{23}$ molecules/mole$) = 3.2 \times 10^{11}$ molecules are divided among 500,000 different plasmids and 1000 different bands. Therefore $(3.2 \times 10^{11})/(500,000 \times 1000) = 640$ molecules of any one tag are expected to be present in any one band. In this case, an amplification factor of $6 \times 10^7/640 \sim 100,000$ is required. There are multiple strategies for converting the terminated sequencing fragments into a form compatible with in vitro amplification. A number of well-known methods exist for converting single-stranded DNA into a double-stranded form. For example, random priming can be performed with a mixture of oligonucleotides that are identical except for several random bases near the 3'-ends. This method is well known in the art; see, e.g., Telenius et al. (1992) and Cheung et al. (1996). PCR then can be performed with primer 18 and a second oligonucleotide primer that is identical to the region shared by the random primers. Other forms of in vitro amplification are possible, such as linear amplification with RNA polymerase (assuming the double-stranded fragment contains a promoter), etc. Variations on this strategy include the ligation of short double-stranded molecules (adapters) to randomly primed sequencing fragments. The second primer is designed to anneal to the adapter sequence (see section 6.7).

Other strategies for amplifying the tag sequences may require removal of any unusual bases at the 3'-ends of the sequencing fragments (e.g., dideoxynucleotides). This step can be performed by limited digestion of the fragments with a 3'-exonuclease (e.g., Exonuclease I, T4 DNA Polymerase, etc.). Now, the linear fragments can be tailed with terminal transferase or even joined to another single-stranded fragment of known sequence through the action of T4 RNA ligase. In both cases, the known sequence (i.e., polyA or the second fragment) can serve as a second priming site for PCR or other form of amplification. Alternatively, the digested sequencing fragments can be circularized with T4 RNA ligase. Inverse PCR can be performed on this circular substrate (Innis et al., 1990). The circles can also be amplified by a rolling-circle type amplification with a strand-displacing polymerase as disclosed in Lizardi et al. (1998) and Zhang et al. (1998).

It is possible in some embodiments to perform the nucleic acid amplification step after the sequencing fragments are hybridized to the oligonucleotide array. Adams et al. (1997) describe a method in which both PCR primers are attached to a solid substrate. Amplification occurs in a fashion similar to traditional PCR only the replicated molecules remain attached to the substrate. In this case, each feature (spot) in the array will contain one oligonucleotide that hybridizes to a particular tag and one common primer (e.g., primer 18, FIG. 1*a*). Note, the sequencing fragments are not complementary to the common primer until the complementary strand is synthesized.

A more preferred method of "in-situ" amplification is the rolling-circle type process mentioned above. In this case, the sequencing fragments can be converted to a circular form before hybridization to the array. The oligonucleotides in the array complementary to the tags will prime the rolling-circle replication. A second common primer can be provided in solution. Other variations of rolling circle amplification may be used. For example, consider a tag complement-sequencing fragment duplex. The sequence upstream of the tag, including the sequencing primer, will be present as a 5'-single-stranded extension of the duplex. A second oligonucleotide can hybridize to the overhang. T4 DNA ligase can join the tag complement to this second oligonucleotide. The second oligonucleotide can then serve as a primer for rolling circle amplification. In this case, the circular substrate is a common molecule that is amplified wherever in the array hybridization of the sequencing fragments has occurred. For a discussion of rolling circle amplification see Lizardi et al. (1998) and Zhang et al. (1998).

The preferred sample tag shown in FIG. 1*a* is joined to the sample polynucleotide in vitro (i.e. it is an "adapter tag"). In certain instances, the sample tag may be a "genomic tag" that comprises a sequence element from the sample polynucleotide. For example, consider an array made by separately PCR-amplifying individual clones from a library (for example, cDNA clones) and spotting the clones on a glass slide (see for example Brown et al., 1998). All the clones are amplified with the same two vector primers. The PCR amplicons may be pooled and sequenced as follows. In this example, the pool of cDNA clones is sequenced with one of the PCR primers by the "Sanger" method. The reaction products are separated and fractionated as described above. Now, the fractionated products are amplified in vitro to generate amplicons comprising sequences from the cDNA (see section 6.7.1.2). These amplicons are hybridized to the spotted array to reconstruct the sequence ladders from individual clones as described above. Note, the cDNA clones comprise the tag complement sequences. Arrays of the cDNA clones constructed by other methods also are suitable (see section 6.8 below). Of course, the common sequences shared by all the clones should be removed from the amplicons prior to hybridization (or removed from the cDNA clones prior to spotting) to minimize cross-hybridization. This step is trivial if a restriction site separates the sample sequence elements from the common elements (i.e., the cDNA clones were ligated into a cloning vector at a restriction site). This method of sequencing with genomic tags is preferred when a library cannot be easily remade or "retrofit" with the adapter tags shown in FIG. 1*a*.

6.3 Massively-Parallel Physical Mapping Methods

The sequencing method described above is a parallel method for fragmenting a polynucleotide at its bases, determining the size of each fragment and thereby determining the linear order of the bases. However, a polynucleotide can be fragmented at features other than single bases. These features, or landmarks, include for example restriction sites, DNA hypersensitive sites, recognition sites for DNA binding proteins, methylation sites or indeed any region of DNA that can be preferentially nicked or cut or otherwise used to define the length of a polynucleotide fragment. For example, the lac repressor binding site can be used as a landmark for directly cutting the DNA with a lac repressor coupled to EDTA-Fe (Shin et al., 1991). This site can be used in an Achilles-heal type cleavage reaction (e.g. Koob et al., 1990), or the lac repressor can be used to prevent an exonuclease from degrading the polynucleotide beyond the site (see Johnson et al., 1990).

In a manner analogous to the parallel sequencing method, it is possible to determine the locations of landmarks in a polynucleotide. In essence, a nucleic acid sequencing reaction is a partial "cleavage" reaction of a polynucleotide clone at its nucleotides. The construction of a physical map involves the partial "cleavage" of a polynucleotide clone at its landmarks. The use of sample tags, fractionation and array hybridization to reconstruct the pattern or "ladder" of landmarks from many different polynucleotides is identical in many respects to the sequencing method.

A preferred landmark is the restriction site. Indeed, the classic notion of physical mapping is restriction mapping. Larger "contigs" are constructed from polynucleotides by comparing their distribution of restriction sites to look for overlaps (e.g. Kohara et al., 1987). The physical map of an entire genome may be constructed by determining the restriction maps of subclones in a massively parallel manner according to the method of this invention. The use of restriction sites is representative and may be substituted by other landmarks.

To construct the physical (restriction) map of a genome, genomic DNA is fragmented and subcloned to form a library. Of course, the method is applicable to any portion of a genome from which nucleic acid can be prepared, such as, e.g., a chromosome or a portion thereof. It is within the skill of the art to isolate a portion of a genome by, e.g., flow cytometry and to prepare a library of genomic DNA from it. In fact, genomic DNA libraries derived from single human chromosomes have been constructed by, e.g., the United States governments National Laboratories, and such libraries are readily available. See, e.g., Birren et al. (1996) and Kim et al. (1994).

The library is constructed de novo in sample-tagged vectors or an existing library can be "retrofit" with sample tags (e.g. Frengen et al., 1999) so that many of the sample tags (i.e., preferably at least 35% of the total) have a unique correspondence to only one sample polynucleotide. That is, a sample tag is joined to only one sample polynucleotide (though one sample polynucleotide can be joined to more than one sample tag). The clones are pooled and cut to completion with a restriction enzyme that cuts in the vector. Typically, this enzyme will be a "rare cutter," that is, it cuts infrequently (e.g., recognizes an 8 base-pair (or longer) sequence). A partial digestion is performed on the pooled clones with another restriction enzyme. The digestion products are separated by size (e.g., by gel electrophoresis, chromatography, etc.), and fractions are collected. Each fraction includes a narrow size distribution of fragments. The fractions can be hybridized directly to an array of tag complements, or preferably tagged amplicons may be amplified from the fractionated DNA before hybridization (e.g., using PCR, RNA polymerase, etc. as described supra). In a preferred embodiment, the sample tags are flanked by sequences common to all the clones as in FIG. 1a. The tags can be labeled (e.g., using fluorescent dyes or other methods known in the art) before or after electrophoresis or during amplification using standard techniques (see above and Kohara et al., 1987). As described above, certain in-situ amplification protocols may be appropriate.

The restriction digest pattern can be reconstructed for any clone by observing the fractions that contain the tag or tagged amplicon that corresponds to the clone. This process can be repeated with several different restriction enzymes. The resulting partial digest patterns provide a "fingerprint" of every clone in the pool. Identical fingerprint patterns in a region indicate two clones overlap as disclosed in Kohara et al. (1987). Note any polynucleotide cleaved with a restriction enzyme will produce at least two fragments, but only the tagged fragment will be visualized.

In this way, a physical map can be constructed from a pooled sample-tagged genomic library without the need to isolate individual clones. However for many uses, individual clones need to be isolated. If only a few clones are needed, these clones can be isolated from the original pool using traditional colony hybridization techniques (e.g. Ausubel et al., 1997). Since a unique sample tag is associated with the clone, the probe would consist of a labeled oligonucleotide that is complementary to the sample tag of interest, assuming the sequence of the sample tag is known. If the sample tag sequence is not known, one could obtain some genomic sequence from every clone using the same array and the sequencing method described above Every clone can be isolated by spatially separating individual clones in the original pool. These clones are then repooled in a systematic way. For example, one million clones can be grouped in three dimensions yielding 300 subpools (100×100×100). The work to pick and pool one million clones is not trivial. As described above, it may be cost effective to optimize the number of informative sample tags; i.e. each tag is associated with only one genomic fragment (of course, it also is possible to construct a different library in each sample-tagged vector and pool one clone from each library). Since the informative sample tags are present only once in the original pool, each of these sample tags should be present in only three of the subpools (representing the x, y & z dimensions of the 3-dimensional grouping). The population of tags in any one subpool can be determined by amplifying the sample tags in the subpool (e.g. by PCR) followed by hybridization to the array of tag complements. Consequently, each sample tag is given a spatial address which corresponds to the clone that contains the sample tag. This approach to pooling is described in, e.g., Yoshida et al. (1993).

Genomic clones can be spatially arrayed using flow cytometry. A reporter gene (e.g., Green Fluorescent Protein as disclosed by Chalfie et al., 1996) can be included in the cloning vector so that transformed (or transfected) cells can be distinguished and separated from "empty" cells. Cells are given sufficient time for phenotypic expression after transformation, and then they are subjected to "cell sorting" (see Galbraith et al., 1999).

It is possible to combine pools after the partial digest, and before size separation. This technique is similar to the sequencing method above in which four sequencing primers with different 5' sequences are used to identify the four terminating nucleotides. In the above physical mapping method, the overhang produced by the "rare-cutter" is ligated to an adapter that differs in sequence for each enzyme used to perform the partial digests. These sequences will serve as priming sites for amplification of the tags after fractionation. The primers can be attached to different labels (e.g., fluorophores) so that more information can be recovered per hybridization. As with the sequencing methods described supra, the inclusion of known fragments attached to known sample tags (i.e., sample-tagged size markers) will uniquely identify each fraction and allow precise molecular weight determination and calibration of signal intensities from one array to another.

6.4 Massively-Parallel Methods for Locating Insertion Elements

The methods described above exploit sample-tags to determine either sequence or physical map information from sample polynucleotides. Particularly with respect to adapter tags, the relationship between a specific sample tag and the sample polynucleotide is not important, i.e., a different sample tag joined to the sample polynucleotide would still suffice to practice the inventions. Nevertheless, a "byproduct" of the methods is the determination of which sample tag is joined to which sample polynucleotide. For example, consider a collection of sample tags and a collection of sequenced sample polynucleotide clones. The two collections are randomly joined to produce sample-tagged clones as described above. The goal is to determine the identity of the sample-tag joined to any particular sample polynucleotide. One need only sequence the sample-tagged polynucleotides as described above to obtain the desired information. Of course, this example is meant to be illustrative. A more practical use is to randomly join a collection of sample tags to chromosomal DNA and determine which tag is coupled to which chromosomal region. When the act of joining is performed in vivo, the sequencing and physical mapping methods can be used to determine the locations of sample-tagged insertion elements.

Figure 2:
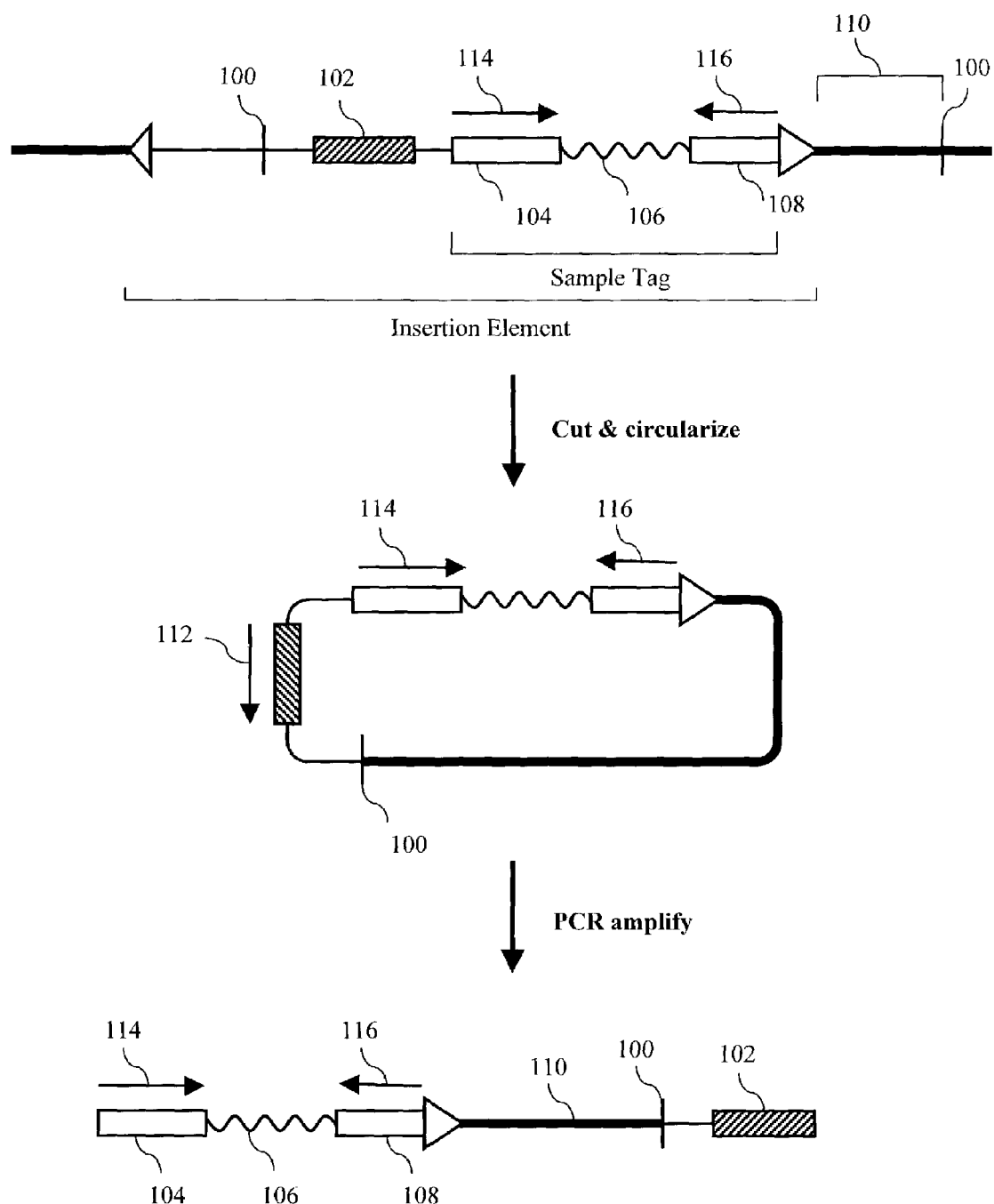
FIG. 2 is a drawing of a preferred embodiment of an insertion element comprising a sample tag and a preferred embodiment of a method to rescue junctions.

In a preferred embodiment, a collection of sample-tagged insertion elements is prepared as shown in FIG. 2, wherein the sample tag comprises a distinct sequence element 106 flanked on both sides by common elements 104 and 108. The insertion elements are easily constructed, for example by ligating a pool of sample tags into the insertion element "backbone". This backbone may reside in a vector that is lost after integration of the insertion element into the genome (e.g. a suicide vector). The insertion element is capable of random integration (or near-random integration) into the genome (for example, retroviral vectors for mammalian cells, Tn10 vectors for *E. coli*, P element vectors for *Drosophila*, transfected DNA of any kind in mammalian cells, etc., see Kleckner et al., 1991; Dellaporta, 1999; Hamilton et al., 1994; Sands, 1998). The method may be practiced using any type of cell or cell line capable of integrating foreign DNA into the genome, such as *Saccharomyces cerevisiae, Escherichia coli, Bacillus subtilis*, mammalian cell lines, plant cell lines, *Drosophila*embryos, zebra fish cell lines, etc. Several transposons have been shown to function in distantly related organisms (Sherman et al., 1998; Rubin et al., 1999), suggesting this mode of integration may be generalized to virtually any cell. In a preferred embodiment, the method may be practiced with cells from which a multicellular organism can be regenerated such as embryonic stem cells (Stewart, 1993), fetal stem cells (Campbell, 1996), plant cells (Azpiroz-Leehan, 1997), etc.

A collection of cell clones is generated by randomly inserting the sample-tagged insertion elements into the genome so that usually any one cell (or organism) preferably will have undergone only one integration event (note: the analysis is identical for multiple integration events) and preferably about 36% or more of the sample-tagged insertion elements have inserted at only one location in the genome (about 36% is easily obtained by choosing about the same number of cell clones as unique sample tags). These cells can be spatially separated. For example, mammalian cells can be infected with a collection of sample-tagged retroviral vectors. Each vector may contain a reporter gene (e.g., GFP). The transfected cells (that is, the cells that express the reporter gene) can be spatially separated from each other and from uninfected cells by flow cytometry and cell sorting (see Galbraith et al., 1999), or by other means. Though this example is directed towards random integration events, the method is equally applicable to "targeted" integration events. For example, insertion elements have been described that target the integration events to genes by providing selectable markers that lack promoters, or must be properly spliced to function, etc (e.g. Sedivy et al., 1989; Friedrich et al., 1991; Skarnes et al., 1995; Ruley et al., 1997;

Sands et al. 1998).

The relationship between the sample tag and the cell clone that contains the sample tag can be easily determined. The cell clones in the collection can be pooled according to some standard scheme such as a 3-dimensional grouping (e.g., one million clones can be ordered into 100+100+100=300 subpools where each tag is present in 3 subpools. These subpools represent the x, y & z coordinates of the 3-dimensional group, see above) The sample tags present in any subpool are determined, for example by PCR amplifying genomic DNA from the subpool with primers 114 and 116 in FIG. 2 to generate tagged amplicons comprising the distinct element 106 (or using any other amplification method known in the art), labeling the amplicons and hybridizing to an array of tag complements wherein for example each feature consists of oligonucleotides complementary to only one distinct sequence element 106. A sample tag that is present only once in the collection (that is, it resides in only one cell clone) will be present in only three subpools (in this example). The three subpools will uniquely define the address of the cell clone that contains the sample tag.

Working with a large collection of cell clones can be very laborious. One can increase the number of informative insertion elements among the collection of cell clones by choosing fewer cell clones than sample tags. For example, a collection of ten million sample-tagged insertion elements may be randomly integrated into cells as above, but only one million cell clones are isolated for subsequent analysis. About 90% of the sample tags will be present in only one cell clone. The sample tags absent from the collection of cell clones are easily determined by amplifying the sample tags from a pool of the cells and hybridizing the amplicons to an array (or arrays) comprising all ten million tag complements. If necessary, new arrays can be synthesized with only the informative tag complements for any subsequent analysis.

6.4.1 Locating Insertion Elements by Sequencing

The position in the genome of any sample-tagged insertion element can be determined "en masse." DNA is prepared from the pooled collection of cell clones. Inverse PCR (see Ochman et al, 1988; Silver et al., 1991) is performed on the DNA as shown in FIG. 2. The DNA is treated with a restriction enzyme that cuts at site 100. The restriction products are circularized with DNA ligase and PCR amplified with the primers 112 and 114, which hybridize to common elements 102 and 104 in the insertion element. In this example, the amplicons comprise the sample tag and one insertion element junction 110. The resulting pool of PCR products is simply a pool of sample-tagged polynucleotide clones that can be sequenced using the massively-parallel sequencing method described above, for example using primer 114 as a sequencing primer and amplifying the fractionated sequencing products with primers 114 and 116.

The method of Inverse PCR described above involves cutting the genomic DNA with a restriction enzyme prior to circularization. Consequently, the amplicon derived from any particular cell clone will be a polynucleotide clone (i.e. all the polynucleotides will be the same length and essentially identical). This polynucleotide clone is correctly termed sample-tagged. However, Inverse PCR could equally be performed with randomly sheared DNA. In this case, the amplicon will not be a polynucleotide clone, but will consist of polynucleotides of various sizes comprising the same sample tag. These tagged polynucleotides will all contain the insertion element junction, so it is more appropriate to refer to a sample-tagged junction than a sample-tagged amplicon. In both cases, the junction sequence generated by the parallel sequencing method will be the same.

The sequence of the insertion element junctions can be used to locate the sites of integration within the genome. Very little sequence information is needed assuming the organism has been completely sequenced. Algorithms for comparing nucleotide sequences are well known in the art (see, e.g., Pearson, 1990; Altschul et al., 1990; Subai, 1997).

It will be obvious to those skilled in the art that methods other than Inverse PCR can be utilized to amplify the sample-tagged junctions. For example, one could use Panhandle PCR (Dieffenbach et al., 1995), Vectorette PCR (Arnold et al., 1991), etc. or even more traditional plasmid rescue protocols (see below) provided the insertion element contains the proper functional elements (e.g. selectable marker and origin of replication).

It is also obvious that other parallel sequencing methods can be used to sequence the sample-tagged junctions. For example, Brenner describes methods for attaching tagged polynucleotides to a solid support by hybridization to arrays or beads comprising tag complements (see Brenner 1997a, Brenner et al., 1998b). The molecules can then be subjected to step-wise sequencing reactions (see for example Brenner et al, 1998a; Brenner, 1998a; Albrecht et al., 1997; Cheeseman, 1994, etc.) in which each "step" generates reaction products from the arrayed polynucleotides. The reaction products are labeled according to a single base (or small number of bases). By visualizing the reaction product at each address in the array, a single or small number of bases can be determined. Repetition of the process produces more sequence information from each tagged polynucleotide in the array. Drmanac et al. (1993) describe a method for sequencing by hybridization with short oligonucleotide probes. In this case, a hybridization reaction can be performed with the tagged polynucleotides attached to the array. The reaction products are short labeled oligonucleotides hybridized to those tagged polynucleotides containing complementary sequence. By repeating the hybridization reaction with different oligonucleotides and noting the addresses of the labeled reaction products, a sequence "profile" can be constructed for the tagged polynucleotides. Usually this profile will consist of several sequence contigs for each tagged polynucleotide (corresponding to the oligonucleotide sequences). Enough contigs will provide the locations of the insertion elements (at least to within several hundred base pairs or so).

6.4.2 Locating Insertion Elements by Restriction Mapping

The location of insertion elements can also be determined by partial restriction enzyme analysis. In this case, the sample-tagged junctions are isolated from the DNA of pooled cell clones by a method that recovers genomic DNA fragments larger than about 1 kb and more preferably larger than about 5 kb. In vitro amplification methods such as those described above can be used with the proper modifications for amplifying large fragments, such as Inverse PCR with "long-range PCR" conditions (Ohler et al., 1992; Barnes, 1994). A preferred method of amplifying the junctions is plasmid rescue in vivo (see for example Hamilton et al., 1994). Plasmid rescue entails cutting the genomic DNA with a restriction enzyme (or randomly shearing the DNA), circularizing the products and transforming the DNA into a host such as *E. coli*. The insertion elements must be designed to carry a selectable marker and a plasmid origin of replication (or some other element to ensure propagation in the host). Clearly, any method capable of recovering large junction fragments is applicable. For example, the insertion element may include a bacteriophage packaging signal (a pac site) for efficient in-vitro packaging of the genomic DNA (or the site, for example the lambda cos sequence, can be ligated as an adapter to the genomic DNA) followed by "infection" of the host. The insertion element may comprise for example a YAC vector (Burke et al, 1987) and telomeres can be ligated to the genomic DNA followed by transformation into *S. cerevisiae*. The genomic fragments comprising the sample-tagged junctions can be enriched in vitro prior to amplification. Taidi-Laskowski et al. (1988) and Rigas et al. (1986) describe methods for enriching for particular polynucleotides in a library by recA-mediated DNA capture. Gossen et al. (1997) describe a method for selecting DNA fragments that bind the lac repressor prior to plasmid rescue (note: this method requires the insertion elements contain the lac operator). Indeed, the Gossen method is easily generalized to any molecule that recognizes and binds to a particular DNA sequence element. Clearly, any appropriate method of enrichment and/or amplification can be used, regardless of the complexity because it need only be performed once or a small number of times to rescue the sample-tagged junctions from the entire collection of cell clones.

The sample-tagged junctions are analyzed by the method described above for physical mapping. In a preferred embodiment, the landmarks are restriction sites. The resulting restriction maps are compared to the restriction map of the genomic DNA from the organism to determine overlaps between the junctions and the genomic DNA. (Note: this analysis can be performed without knowledge of the complete genomic sequence; only the sequence of the relevant restriction enzyme sites throughout the genome is required. This information can be determined by the physical mapping procedure described above). It also is worth noting that this strategy and the physical mapping method can be performed with much larger tags than is practical with the sequencing strategy.

The tag complements used above for positioning insertion elements by sequencing or physical mapping are preferably synthesized as short oligonucleotides as described below for example by the method of Fodor et al. (1995) or Montgomery (1998). In this case, the sequence of the sample tags must be known. The arrays may also be constructed by amplifying sample-tags directly from the cell clones and "spotting" the amplicons on a slide or synthesizing the arrays by in-situ amplification of randomly distributed sample tags as described below in section 6.8. In the latter two examples, the sequence of the sample tags need not be known. Note if spotting is used to construct the arrays, then each tag complement (derived from an amplified sample tag) can have an address in the array that corresponds to the address of the cell clone (see for example Hensel et al., 1995). As a result, the sequence or physical map associated with each sample tag is already associated with a cell clone (by virtue of the address of the tag complement), so the analysis with subpools described above is not necessary. Of course, this latter spotting method is only informative when a cell clone contains only one sample-tagged insertion element.

In some cases, the application of both strategies outlined above (sequencing and physical mapping) may be used to determine precisely the position of insertion elements. For example, a genome with many repetitive elements may be refractory to analysis by sequencing alone. Integration events that occur in repetitive elements will not always yield single copy sequence (that is, sequence that occurs only once in the haploid genome). However, restriction mapping can provide positional information that covers many thousands of base pairs. This information will usually place the insertion element at a single location in the genome. The sequence information then can be used to locate the exact position of the insertion element to single base resolution.

By application of the methods described above, the location in the genome of sample-tagged insertion elements can be determined as well as the spatial locations of the cell clones (or organisms) that contain the sample tags. The insertion elements that integrate within coding regions will often disrupt proper gene function. These integration events are gene knockouts. By application of the methods to totipotent cell lines (such as embryonic stem cells), multicellular organisms carrying the knockouts can be constructed. If a particular gene is not "hit" by an insertion element, it is possible to use insertion elements in surrounding regions to delete the gene. For instance, FRT sites can be incorporated into the insertion element to facilitated site-specific recombination (via FLP recombinase) between two insertion elements. If the two insertion elements do not already exist in the same cell, they can be crossed together by mating (assuming the cells or organisms are capable of mating). One product of the recombination event is a deletion of the DNA between the two vectors (see Golic, 1991 & 1994; Golic et al., 1996; Xu et al., 1993; Kilby et al., 1993). In this way, other types of chromosomal deletions can be generated.

6.4.3 Locating Insertion Elements with "Genomic" Tags

Alternative methods are available for determining the genomic position of the insertion element. These alternatives do not require a sample tag to be present in the insertion element. The sample tag is provided by the genomic DNA. These methods can be particularly useful when it is prohibitively difficult to incorporate exogenous DNA into the genome. For example in *Drosophila melanogaster*, an appropriate mating protocol can be used to generate many offspring that have undergone independent germ-line transposition events of an endogenous P element (see Hamilton et al., 1994). However, the introduction of an in-vitro modified P element into the genome can be very time consuming and costly. Consequently, an alternative to the use of sample-tagged P elements is beneficial.

In one embodiment, a collection of cells (or organisms) with insertion elements is prepared. The collection is grouped into subpools according to a standard scheme, for example 3-dimensional pooling as described above. From each subpool, insertion element junctions are rescued by Inverse PCR or by another standard method (as described above). The amplified junctions are labeled and hybridized to an array of tag complements. In this case, the tag complements are prepared from the genomic sequence. For example, short single-copy sequences that are randomly distributed throughout the genome may be synthesized in arrays according to the methods of Fodor et al. (1995) or Montgomery (1998), or the sequences may be derived from ESTs (expressed sequence tags, see Adams et al., 1991) or the junction sequences themselves (see below in section 6.4.3.1). Hybridization to the array reveals the spatial address of the cell clone (or clones) that contains an insertion element in the genome near the genomic tag (that is, which cell contains a junction comprising the genomic tag). Depending on the number of polynucleotide clones in the collection and the length of rescued DNA, multiple clones may hybridize to the same tag complement (i.e., the insertion elements integrated near the same genomic tag). In this case, the spatial address is ambiguous. It is possible to minimize these ambiguities by analyzing the collection pooled according to a second scheme different from the first as described in Barillot et al. (1991). A preferred pooling scheme will provide unambiguous spatial addresses for the clones without the need for further analysis of subpools. Other pooling schemes employ two or more separate steps to determine addresses (see for example, Hamilton et al., 1991), where subsequent steps require analysis of fewer subpools. While these other schemes require analysis of fewer subpools to determine the address of a single cell clone, the work cannot be performed efficiently in parallel. These step wise pooling strategies are more appropriate for positioning one or a small number of insertion elements at a time.

Clearly, the above analysis provides more information than simply the spatial addresses of the "genomic-tagged" cell clones. For example, if the genomic sequence is known, then the locations of the genomic tags are known. Consequently, the approximate positions of the genomic-tagged junctions are known. If the absolute positions of the genomic tags in the genome are not known (for example, the tag complements could be derived from unmapped cDNA sequences), one still knows the approximate "relative" locations of the insertion elements.

6.4.3.1 Refining the Locations of Genomic-Tagged Insertion Elements by Parallel Sequencing One method to obtain more precise positional information (absolute or relative) is simply to sequence the junctions in parallel. A subset of the original collection of cell clones is pooled and the insertion element junctions are amplified as described above. This subset is chosen so that many of the genomic tags (preferably more than about half) are present in only one cell clone. These amplicons are joined to sample tags and sequenced according to the method of this invention (or any other tag-based parallel sequencing method as described above). Preferably, the entire genome has already been sequenced so any sequence from a junction will immediately position it and reveal the associated genomic tag (regardless of whether or not the genomic tag is actually sequenced along with the junction).

Preferably, the order of events is reversed; the junctions are sequenced first and then the genomic tags are chosen, the array of tag complements is synthesized, and the spatial addresses are determined. If desired, junctions from the entire collection of cell clones can be prepared as one pool, joined to sequence tags and sequenced. Different subpools of the sequence-tagged junctions can be sequenced until nearly all of the junctions are analyzed. For example, consider a collection of 100,000 cell clones. The 100,000 junctions are cloned into a pool of about 300,000 different sequence-tagged vectors. About 300,000 clones are pooled and sequenced in parallel with an array of 300,000 tag complements. Approximately 100,000 clones in the pool are sequence-tagged and so yield sequence data (that is, about 36% (1/e) of the sequence tags are associated with only one junction). Those 100,000 clones will yield sequence information from about 64,000 different junctions. Repeating the process on a different pool of 300,000 clones will yield the sequence from about 64% of the remaining junctions (approaching 90,000 sequenced junctions). Tag complements are designed from the sequence information and a new array is synthesized. Now the collection of cell clones is repooled in a 3-dimensional array with 47 sub-pools per dimension. The junctions are amplified from each subpool and separately hybridized to the array to determine cell clone addresses. This order of events permits one to locate the insertion elements with genomic tags without first having any genomic sequence information. Of course, the locations are relative but can later be placed in their absolute chromosomal locations for example by completely sequencing the genome.

Restriction maps for genomic DNA flanking the insertion elements can be quickly constructed by rescuing large fragments comprising the junctions in sample-tagged vectors using an appropriate protocol such as plasmid rescue as described above. The analysis of these sample-tagged junctions is identical to the methods described in Section 6.3. The resulting restriction maps can be easily aligned with the genomic tags described in the previous paragraph if the genomic sequence is known. Alternatively, the sequence of the junctions can be obtained directly from these large sequence-tagged clones (or smaller subclones comprising the junctions and sample tags can be generated and sequenced), so the same sample tag is used for both sequencing and physical mapping. In this way, any rearrangements in genomic DNA flanking the insertion elements can be quickly ascertained.

6.4.3.2 Refining the Locations of Genomic-Tagged Insertion Elements by Physical Mapping An alternative method to more precisely locate the "genomic-tagged" junctions is to employ a fractionation approach similar to the physical mapping method described in section 6.3. Inverse PCR, plasmid rescue and other methods can rely on cleavage of genomic DNA at well defined locations. Restriction enzymes are usually employed though other methods exist for cutting DNA at defined sites. See Szybalski (1997) for a review of some other methods. The distance between the cleavage site and the integration event determines the length of the rescued DNA fragment. Consequently, if the distance between the genomic tag and the cleavage site is known, then knowledge of the size of the rescued DNA will more precisely position the site of the insertion element. Preferably, the genome is sequenced before performing this analysis to simplify the choice of genomic tags near cleavage sites.

The size of the rescued DNA is readily determined. Genomic-tagged junctions are prepared from the cell clones and separated by size (for example by gel electrophoresis or chromatography). Fractions are collected and the junctions in each fraction are amplified and labeled with the same (or nearby) primers that first were used to amplify the DNA. The genomic-tagged amplicons in each fraction are separately hybridized to an array of tag complements. The hybridization patterns can be deconvoluted as described above for the physical mapping method to determine the fragment size. Note that the genomic tags will be present in only a small subset of fractions since only one fragment size per genomic tag is present in the collection. Of course, inclusion of the appropriate size standards before fractionation will increase accuracy.

In the embodiment described above, the entire length of DNA between the cleavage site and the insertion element is hybridized to the array. This requirement limits the range of detectable integration events from a particular cleavage site. If the genomic tag is located within several hundred base pairs, more preferably within one to twenty base pairs of the cleavage site, then it is possible to determine the location of integration events many thousands of base pairs from the cleavage site. Similar to the methods above, the collection of integration events is pooled in a standard fashion such as a 3-dimensional scheme. Genomic DNA in the neighborhood of the insertion element is rescued from the subpools by a method appropriate to larger DNA fragments (e.g., plasmid rescue, see above section 6.3). The genomic DNA can be rescued so that the cleavage site is juxtaposed to a known sequence, such as one end of the insertion element or an adapter. Alternatively, DNA can be rescued from the subpools, then cut at the cleavage site and joined to a known sequence. In either case, a defined sequence is joined to the cleavage site therefore a defined sequence is close to the genomic tag. Now the genomic tag sequences can be amplified by any standard method for amplifying DNA at vector-insert junctions. Representative approaches are disclosed by Swensen (1996); Huang (1997); Ogilvie et al. (1996); Wu et al. (1996). The amplified genomic tags are hybridized to an array of tag complements and the spatial addresses are determined as above.

More precise positional information can be obtained by determining the length of the DNA fragment that separates the cleavage site from the insertion element. Large fragments comprising the junctions are rescued from the pooled collection of cell clones using the same method that was previously applied to the subpools (alternatively, the rescued DNA from all the subpools can be combined into one pool. A defined sequence is joined to the cleavage site (near the genomic tag as described above) and the rescued DNA is linearized, preferably at a restriction site very near the junction for example a site engineered into the insertion element. The end result is a collection of linear molecules. Each molecule has a defined sequence near the genomic tag at one end and some insertion element sequence at the opposite end. Of course, other DNA fragments may be generated during this process, but they are not joined to genomic tags. Now this collection of linear molecules can be fractionated by size. The genomic tags in each fraction are amplified and labeled as above. Finally the genomic tags are hybridized to an array of tag complements and the size of each linear molecule is deconvoluted from this data.

Further resolution of the positions of vector integration may be achieved by performing a partial restriction digest on the collection of linear molecules. The analysis is identical to that described in section 6.3 with the exception that tagged amplicons are generated using a vector-insert junction amplification protocol. Restriction mapping has the advantage that the distance between the integration site and other, closer cleavage sites will be known. In addition, comparison of the restriction map to the genomic restriction map will uncover any DNA rearrangements that may have occurred during any step of the procedure.

6.5 Sample Tags

Sample tags used in the analysis of sample polynucleotides fall into two main classes: adapter tags and genomic tags. In general, adapter tags are joined to the sample polynucleotides to practice the invention. Genomic tags comprise sequence elements that are contained in the sample polynucleotides in their natural state prior to practicing the invention (e.g., the sample tag comprises cDNA or genomic DNA). Of course, one skilled in the art will recognize sample tags can be a combination of adapter and genomic tags, indeed many genomic tags will comprise additional sequences joined to the sample polynucleotide to practice the invention (for example, to facilitate amplification of the genomic tags). Genomic tags are particularly useful to position certain insertion elements, as described above. Genomic tags may also substitute for adapter tags in the sequencing and physical mapping embodiments.

6.5.1 Designing Tags

A preferred form of adapter tag is shown in FIG. 1a. A variable, or distinct sequence element 12 is flanked on both sides by common sequence elements 10 and 14. The distinct element is used to identify the sample polynucleotide. The common elements, which are shared by many sample tagged polynucleotides, are used as priming sites to amplify the sample tag. Methods for designing the distinct sequence elements are well known in the art. For example, Brenner (1997b) teaches how to use a simple algorithm to choose suitable tags.

In vitro selections can be employed to create a pool of sample tags. Montgomery (1998) and Fodor et al. (1995) teach methods for making arrays with oligonucleotides of any sequence. Consider an array of 1000 or more oligonucleotides wherein each oligonucleotide comprises a distinct element flanked on both sides by common elements. In addition, the common elements contain the recognition sequence for a restriction enzyme that cuts at or near the two junctions of the distinct and common sequence elements. Now, the distinct elements can be PCR amplified from the array by priming at the common elements (DNA polymerases are known to function on arrays, see Bulyk et al., 1999). A label (e.g., fluorescein) can be incorporated into the amplicon. The common elements are separated from the distinct elements by cleaving the amplicons with the restriction enzyme. An affinity moiety (e.g., biotin) can be included in the PCR primers to facilitate affinity separation of the common elements (and uncleaved amplicons) from the distinct elements. These distinct elements are hybridized to the array. Alternatively, the common elements do not have to be removed from the amplicons if the hybridization is to a second array of oligonucleotides comprising only the distinct sequence elements and not the common elements. Only those sequences that produce strong hybridization signals in this assay are chosen as sample tags. For example, a second array with only the chosen sequences can be synthesized as above. The tags are amplified from the array and joined directly to sample polynucleotides or the tags are cloned into vectors for subsequent manipulations.

A variation of the above in vitro selection is possible. In this example, the distinct sequence elements are randomly synthesized on a DNA synthesizer (e.g., ABI Model 394). For instance, all possible 20 base oligonucleotides can be synthesized at one time by programming the synthesizer to incorporate all four bases at each position. The mixture of random oligonucleotides is cloned into a vector, and a random subset of 1000 or more clones is chosen for further analysis. Now the distinct sequence elements can be amplified by priming in the vector sequences on either side of the distinct element. It is possible to select for optimal adapter tags by denaturing the amplicons and selecting for rapidly renaturing distinct sequence elements. For example, the renatured amplicons can be treated with a single-strand specific endonuclease (e.g., Mung Bean Nuclease or S1 nuclease) to destroy mismatched duplexes and single-strand DNA. Surviving DNA can be reamplified and cloned or subjected to another round of selection. Other selections are possible. For example, the amplicons can be designed as above where the PCR primers contain an affinity moiety (e.g., biotin) and the common sequence elements contain restriction enzyme recognition sites near the junctions of the common and distinct sequence elements. The affinity moiety is used to bind the tags to a solid support. The restriction sites are used to ligate the distinct sequence elements to a different vector or adapter thereby replacing the first set of common sequences with a second set. The distinct sequence elements are PCR amplified with a second pair of primers specific to the second set of common sequence elements. The resulting amplicon is hybridized to the first amplicon bound to the solid support. Unhybridized strands are washed away and hybridized strands are denatured and reamplified with the second pair of primers.

The random tag selections described above yield populations of sample tags with distinct sequence elements of unknown sequence. These sample tags may be used to make arrays by spotting (see Brown, 1998) or as outlined below, to make arrays wherein the tag is a "place holder". Therefore the sequence of the sample tags need not be determined. However, to utilize arrays made according to the methods of Fodor et al. (1995) or Montgomery (1998), the sequence of the tags must be determined. Of course, each tag could be individually cloned and sequenced. A more preferred method is simply to join the first set of tags of unknown sequence to a second set of tags and sequence the first set in parallel according to the method of this invention. That is, the first tags are the sample sequence elements with respect to the second tags. By repeating the process, one set of tags can be used to construct a larger set of tags.

In some embodiments, sample tags may be larger than the synthetic oligonucleotides described above. For example, restriction mapping may be performed on sample polynucleotides that are hundreds of kilobases in size. Consequently, large sample tags even greater than one kilobase can be tolerated. A simple way to construct a collection of sample-tagged vectors for cloning sample-tagged polynucleotides is to clone into a vector a random collection of fragments from genomic DNA (or normalized mRNA). Each random fragment (and in some cases flanking vector DNA) serves as a sample tag. Sample polynucleotides are cloned into the collection of sample-tagged vectors. Arrays may be constructed by separately PCR amplifying and spotting the random fragments in the vector. Also commercially available arrays may be used. For example, Affymetrix sells arrays of oligonucleotides that hybridize to yeast (*S. cerevisiae*) DNA and mRNA. In this case, one tag made from yeast sequences may hybridize to multiple different oligonucleotides in the array.

6.5.2 Multiple Sample Tags Per Sample Polynucleotide

In some embodiments, it is useful to join more than one sample tag to a polynucleotide. For example, sequence information or a restriction map may be obtained from both ends of a sample polynucleotide. Consider a "dual tag" vector that comprises two different tags on either side of a cloning site into which the sample polynucleotide is inserted. Of course, a collection of these vectors could be constructed one at a time, but this method is too time-consuming to construct large sets of dual-tag vectors. Individual sample tags, selected as described above, can be synthesized as pairs in an array, for example by the method of Fodor et al. (1995) or Montgomery, so that a cloning site separates each pair and common sequence elements flank both sides of a pair. The pairs of sample tags can be amplified by the common regions and cloned into a vector to form sample-tagged vectors. Sample polynucleotides are cloned between the pairs of sample tags at the cloning site.

One can construct a collection of vectors with one tag as outlined above and then randomly insert a second collection of tags into this collection of sample-tagged vectors. However, information about the relationship between the two tags is useful (i.e., which tags are in the same vector). In this way, information derived from opposite ends of the same sample polynucleotide can be related. A simple way to relate the two set of tags is to use one set to sequence the other set according to the method of this invention. Naturally, the random distribution of the second set of tags means a one-to-one relationship between tags in the two sets will not always exist. This problem is minimized by working with two large collections of tags and choosing a smaller collection of dual-tag vectors. For example, the two collections of tags may each contain 10 million distinct tags. After randomly joining the two collections, a million dual-tag vector clones can be chosen randomly, in which case more than 80% of the dual-tag vectors will comprise two tags that can uniquely identify each other.

Figure 3:
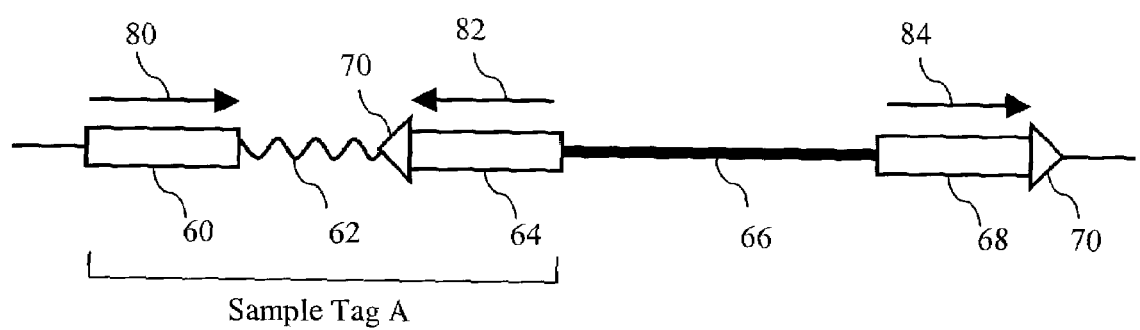
FIG. 3 is a preferred embodiment of a vector for sequencing or constructing physical maps from both ends of a sample polynucleotide.
Figure 4:
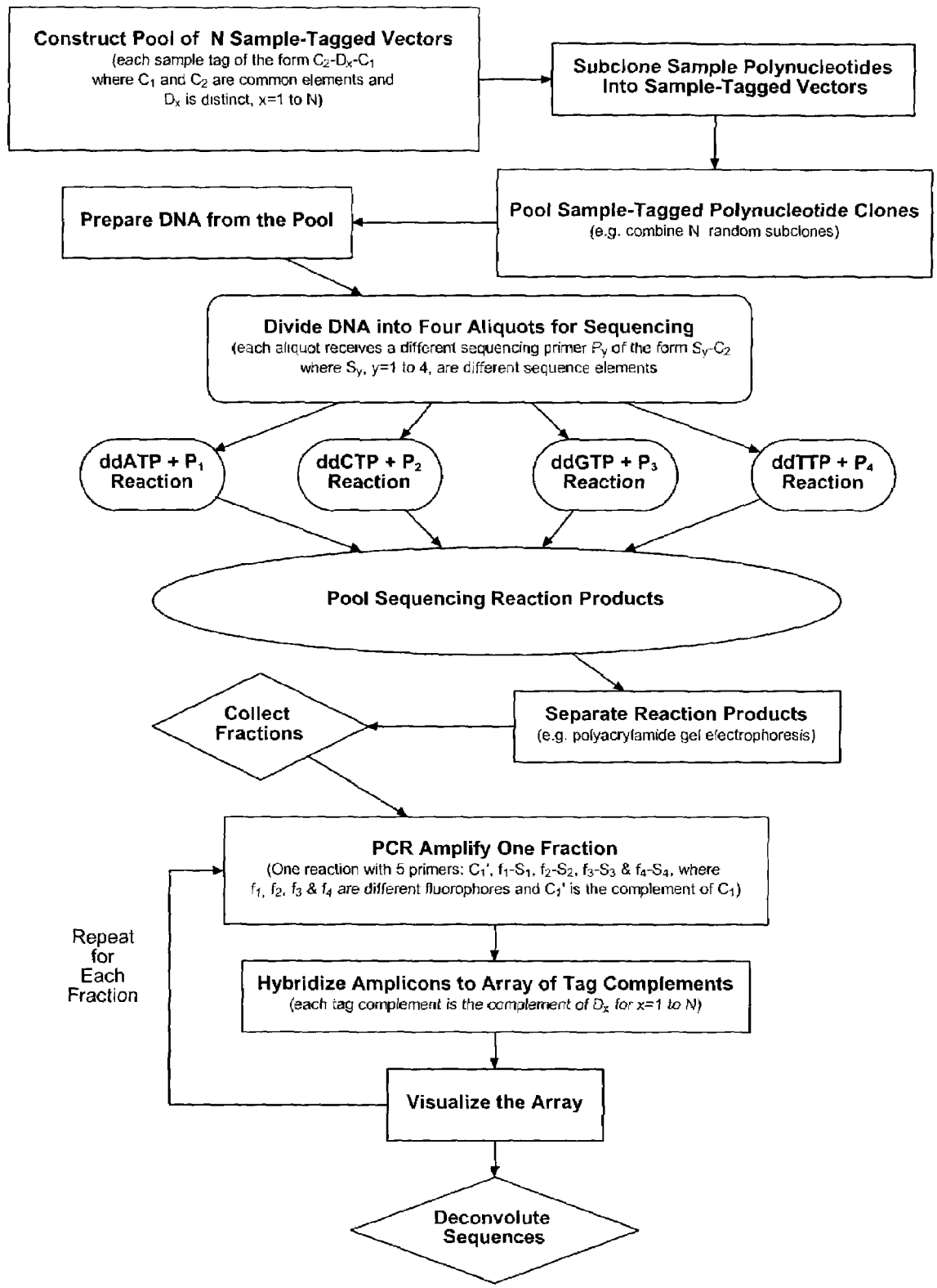
FIG. 4 is a flow chart of a preferred method for sequencing.
Figure 5:
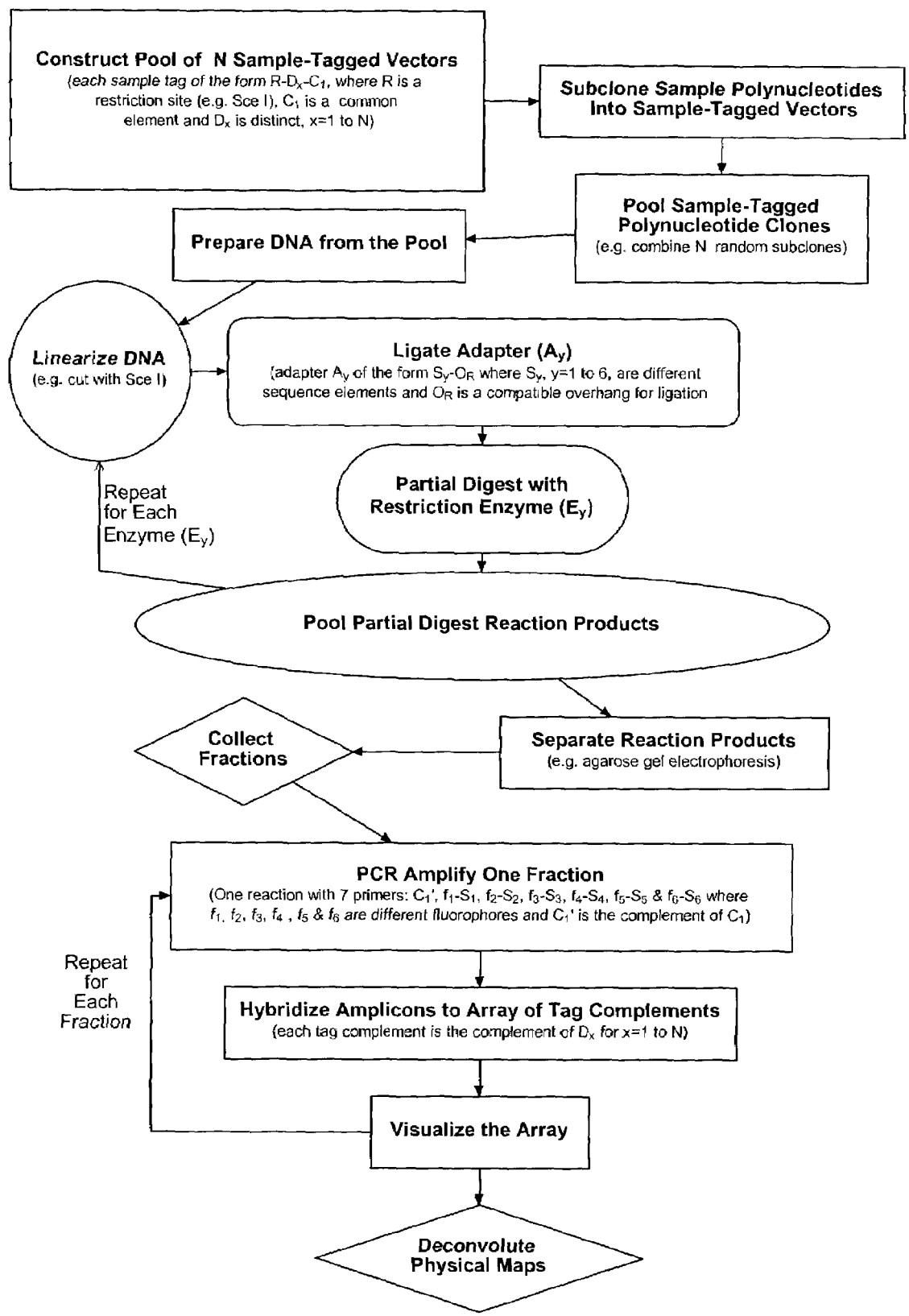
FIG. 5 is a flow chart of a preferred method for constructing physical maps.
Figure 6:
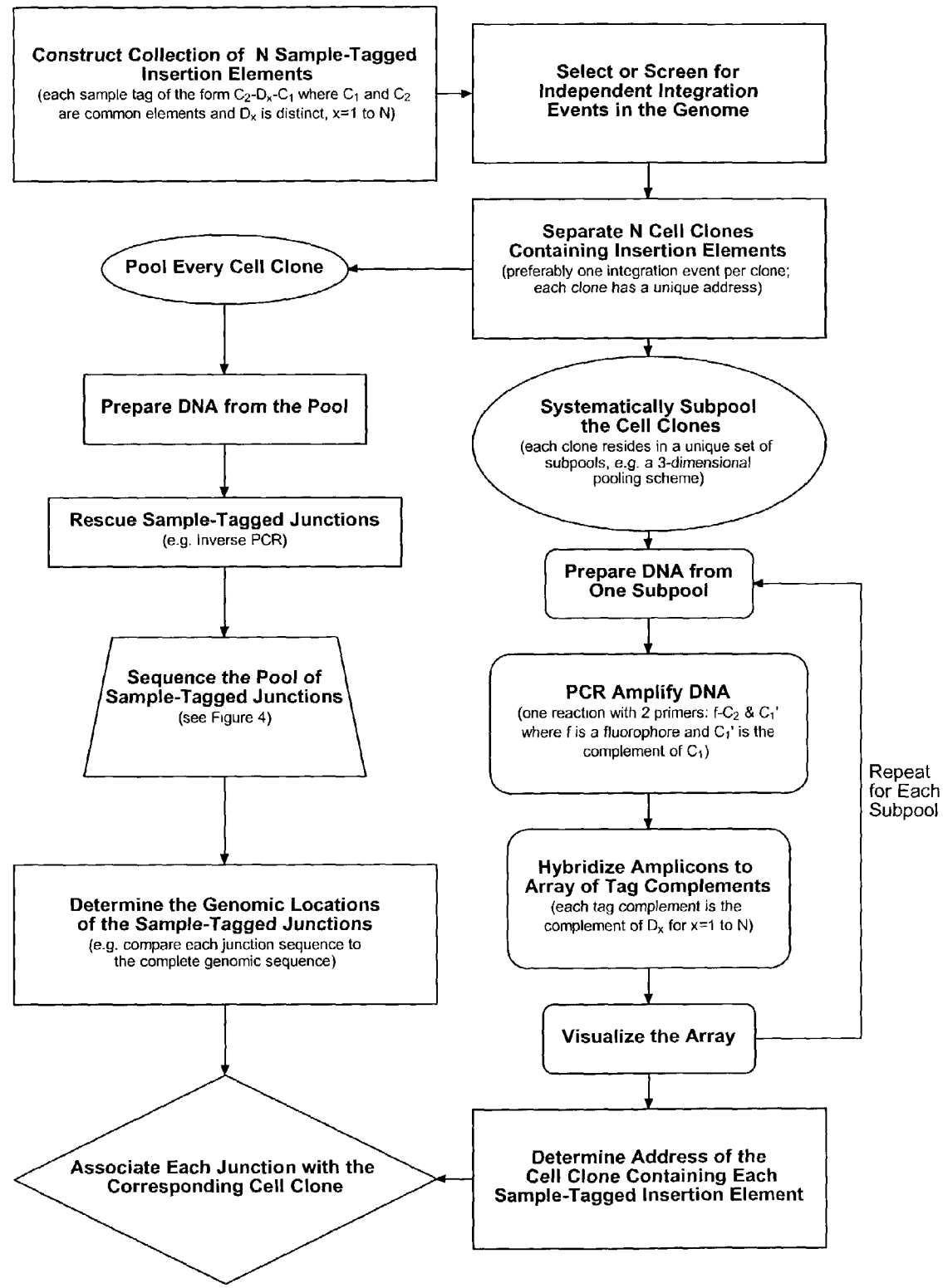
FIG. 6 is a flow chart of a preferred method for producing cells containing located insertion elements.

Another method to obtain data from both ends of a sample polynucleotide employs the vector design in FIG. 3. Site 70 represents the recombination site for a site-specific recombinase (for example, a lox site where cre recombinase acts or a FRT site where FLP recombinase acts), and the orientation of the site is represented by the direction of the arrow. The common elements 60, 64 and 68 are present in all the sample-tagged clones, whereas the distinct element 62 uniquely corresponds to the sample sequence element 66. Sample tag A for analyzing one end of sample 66 comprises the following sequence elements: 60, 62, 70 and 64. Sample tag A can be PCR amplified with primers 80 and 82. Sample tag B for analyzing the opposite end of sample 66 comprises 60, 62, 70 and 68. Sample tag B can be PCR amplified with primers 80 and 84. The tags are identified by hybridizing the amplicons to tag complements comprising at least part of the distinct element 62. Notice sample tag B does not exist until the sample-tagged clones are exposed to the site specific recombinase. After exposure to the recombinase, the population of sample-tagged clones can contain approximately equal amounts of the sample tag A and B forms. The invention is practiced on this mixture, for example, the clones can be sequenced with primer 80. Only one set of tags (either sample tag A set or sample tag B set) is amplified at a time. In this way, the same distinct sequence element 62 is used to obtain data from both ends of the sample 66. The collection of sample-tagged vectors can be constructed as outlined above for "single-tag" vectors.

Three or more sample tags can be used to analyze a sample polynucleotide. For example, sample-tagged transposons can be used to randomly insert multiple sample tags in vitro or in vivo (see Strathmann et al., 1991; Craig, 1996; Smith et al., 1995).

6.6 Separating and Fractionating Tagged Reaction Products

Numerous methods exist for separating nucleic acids by size, for example, chromatography (e.g., Bloch, 1999; Gjerde, 1999; Thayer et al., 1996; Hearn, 1991), electrophoresis and "Time of Flight" separations based on charge to mass ratios (e.g., MALDI-TOF). Different methods resolve DNA fragments in different size ranges and will be appropriate to different embodiments of the invention. It is clear to one skilled in the art that any method of separation can be used which resolves fragments in the appropriate size range and permits collecting the fragments in a form compatible with subsequent amplification and/or hybridization to an array.

A preferred method of separation is gel electrophoresis. Agarose is a preferred gel matrix for separating nucleic acid fragments that differ in size by tens to thousands of bases. Polyacrylamide is a preferred gel matrix when single-base resolution is required such as sequencing embodiments. Electrophoresis may be performed in, for example, slab gels and capillaries.

Fractionation simply entails collecting the DNA fragments in one size range away from the DNA fragments in other size ranges. For example, a gel containing electrophoresed DNA fragments can be physically sliced into sections perpendicular to the direction of electrophoresis, and the DNA fragments can be removed from each slice by several means (e.g., β-agarase digestion, electroelution, etc. see Ausubel et al., 1997). Andersen (1998) describes an apparatus for electroeluting and collecting separated molecules from a gel en masse, without slicing the gel. Alternatively, the DNA fragments can be collected as they electrophorese through the end of the gel. The fragments may be collected onto ionized paper or simply collected in separate containers (see for example Beck, 1993; Richterich et al., 1993; Xu et al., 1997;

Wong, 1999; Mills, 1993; Karger, 1996; Kambara, 1996; Israel, 1976).

Chromatography (e.g., HPLC) can be performed with computer-controlled instruments such that eluting DNA fragments are automatically collected in separate containers for further analysis (Weston, 1997; Bloch, 1999).

6.7 Amplifying Tags

A critical element of the invention is the ability to amplify tags before and/or after hybridization to the array.

6.7.1 Amplification Prior to Hybridization

Amplification of tagged reaction products can generate tagged amplicons with much lower sequence complexity. Consequently, there is more material to perfectly hybridize to the tag complements and there is much less material to cross-hybridize to the tag complements. Both factors contribute to improving the signal to noise ratio (i.e., sensitivity) of hybridization to the array of tag complements. More copies of each tag will drive the hybridization kinetics, which allows more tags to be analyzed in each hybridization reaction. The lower complexity of material not meant to hybridize to the array will minimize the presence of false signals or background due to cross-hybridization.

6.7.1.1 Adapter Tags

The adapter tags shown in FIG. 1a are easily amplified by the preferred method of the polymerase chain reaction with primer 18 and primer 20. Other methods of in vitro amplification will also work, for example 3SR and related methods (e.g. Gingeras et al., 1988; Kwoh et al., 1989; Gebinoga et al., 1996), Strand Displacement Amplification (Walker et al, 1992 & 1993) and rolling circle amplification (Lizardi et al., 1998; Zhang et al., 1998). Linear amplification methods can be used. For example, one of the common regions may encode a promoter for an RNA polymerase (e.g., T7, T3 and SP6), and in vitro transcription will amplify the tag. A "one-sided" PCR reaction in which one primer is in excess over the other primer ultimately will produce a linear amplification of the tag. One could even amplify the tags with more traditional recombinant DNA methods involving cloning the tags into a vector and passaging the clones through a host such as *E. coli.*

The in vitro methods of amplification can produce double-stranded amplicons. To maximize hybridization to tag complements, one strand of the amplicon may be removed prior to hybridization to the array. For example an affinity moiety, such as biotin, may be incorporated in one of the primers. The amplicon can be denatured and the biotin-containing strand removed with streptavidin coated beads (e.g. Mitchell et al., 1989). Enzymatic methods also may be used to remove one of the strands. For example lambda exonuclease preferentially degrades DNA with a 5'-phosphate group. By incorporating a 5'-phosphate in only one of the primers, only one strand of the amplicon will be degraded (see Ausubel et al., 1997; Takagi et al., 1993).

Other modifications to the amplicon may facilitate hybridization. The common sequence elements 10 and 14 depicted in FIG. 1a, can be removed from the amplicons prior to hybridization by incorporating restriction enzyme recognition sequences in the common sequence elements. By choosing enzymes that cleave outside their recognition sequences (e.g., BsrDI, BsmBI, etc.), it is possible to completely separate the common sequence elements from the distinct element 12 by cutting the amplicons with the enzymes.

6.7.1.2 Genomic Tags

Genomic Tags are not as easily amplified as adapter tags because in some embodiments, common sequence elements cannot be so readily designed to flank both sides of the distinct genomic sequence element in the sample-tagged polynucleotide. Consider a genomic tag consisting of a common sequence element shared by other sample-tagged polynucleotides and an adjacent sequence element from the sample polynucleotide. Amplifying the genomic tag is analogous to amplifying the DNA at a vector-insert junction. Representative approaches are disclosed by Riley et al. (1990), Lagerstrom et al. (1991), Kere et al. (1992) and Liu et al. (1995). Inverse PCR (Silver et al., 1991) is a simple method to provide a second common sequence element for amplification of the genomic tag by PCR. Double-stranded tagged reaction products are cut with a restriction enzyme and ligated under conditions that promote circularization. Now the first common sequence flanks both sides of the distinct sequence element provided by the sample polynucleotide. Of course, not all embodiments of this invention yield double-stranded reaction productions (for example, some sequencing embodiments) so the reaction products first must be converted to the duplex form. Synthesis of the complementary strand can be achieved in vitro with small random primers and a DNA polymerase (e.g., T4 DNA polymerase, the Klenow fragment, etc.). Alternatively, T4 RNA ligase can circularize single stranded DNA and RNA.

Another method to provide a second common sequence element entails engineering a restriction enzyme site in the first common sequence element. Certain restriction enzymes cleave well away from their recognition sequence (e.g., Bpm I, Bsg I, Mme I, etc.). These enzymes can cut up to 20 base pairs into the sample sequence elements. The second common sequence element can be ligated as an adapter to the cleaved reaction products. Prior to amplification, the genomic tags can be purified from other ligation products by, for example, denaturation, followed by hybridization to a solid support-bound oligonucleotide that is complementary to the first common sequence.

Vector-insert junctions are routinely amplified by providing the second common sequence element during a random priming event. A first oligonucleotide of known sequence (the primer oligo), sometimes coupled to random bases at the 3'-end, is used to prime DNA synthesis after denaturation of double-stranded DNA. If the primer oligo initiates DNA synthesis near the vector junction (i.e., near the first common sequence element), then the junctions (i.e., genomic tags) can be amplified by PCR with the primer oligo and an oligonucleotide complementary to the vector. A variation of this strategy for amplifying short genomic tags entails tethering the primer oligo to the first common sequence element. The local concentration of the primer oligo becomes very high near the genomic tag, which means the random priming event is likely to occur very close to the tag. The tethering event can be accomplished by first tethering the primer oligo to a second oligonucleotide that is complementary to the first common sequence element. The two oligonucleotides may contain a biotin moiety and they are coupled by a streptavidin "bridge." Hybridization of the second oligonucleotide to the first common sequence element serves to tether the primer oligo to this region. Of course, other functionally equivalent methods to tether two oligonucleotides can be used to practice this embodiment.

6.7.2 In situ Amplification

Tagged reaction products may be amplified after hybridization to the array. The amplicons must remain tightly associated with the hybridized products from which they are derived. This association may be maintained by a physical coupling of the reaction products and amplicons (e.g., rolling circle amplification) or diffusion of the amplicons can be restricted.

Several methods have been described for in situ amplification. Lizardi (1998) and Zhang et al. (1998) disclose methods employing rolling circle replication and strand displacement. For example, consider a linear tagged reaction product with a tag comprising a common sequence element at the 5'-end of the reaction product flanked by a distinct sequence element. The tag complement, to which the reaction product is hybridized, consists of an oligonucleotide complementary to the distinct element. Another oligonucleotide, complementary to the common element with an additional sequence element at the 3'-end, may be hybridized to the common element, then ligated to the tag complement. The additional 3'-overhanging sequence element can prime rolling circle replication from a closed circular DNA molecule provided in solution. The amplicons are covalently coupled to the tag complement.

Obvious variations are possible, for example, the tagged reaction product may possess the common element at the 3'-end, in which case rolling circle replication may be primed directly from this sequence element. In addition, Lizardi et al. (1998) describe the use of oligonucleotides with reversed backbones capable of hybridizing to the common sequence element while providing an overhanging 3'-end that can prime rolling circle replication. The reverse-backbone oligonucleotide may be hybridized to the common element, then ligated as above to the tag complement, allowing the rolling circle replication products to be covalently coupled to the tag complement. The tagged reaction product itself may be circularized prior to hybridization to the array. In this case, the tag complement may prime rolling circle replication directly from this circular substrate.

Adams et al. (1997) describe a method for in situ amplification in which two primers for PCR are attached to a solid support. Consider the tagged reaction product described above, in which the tag consists of a common element at the 5'-end followed by a distinct element. The array comprises oligonucleotide tag complements, coupled to a solid support at their 5'-end in addressable locations and a common oligonucleotide identical in sequence to the common region, distributed throughout the array. Assuming only the non-complementary strand of the common sequence element is present in the hybridization reaction, the reaction product can only hybridize at the tag complement. A subsequent polymerization reaction will extend the tag complement into the common sequence element. The resulting extension product can be amplified in situ by PCR according to the method of Adams et al. (1997).

Chetverin et al. (1997) and Church (1999) describe methods for amplifying nucleic acids in an immobilized medium to generate discrete "colonies" of amplicons. This method can be applied to the present invention by adding the immobilization media to the array, for example after hybridization of the tagged reaction products. Church describes a method to attach the nucleic acids to the immobilization media with a polymerization reaction that is primed by a complementary oligonucleotide already attached to the media (see Khrapko et al. (1996) and Kenney et al. (1998) for other methods of attaching oligonucleotides to agarose and polyacrylamide membranes). Amplification is performed using 3SR (Gingeras, 1988) in which the oligonucleotides encode the promoter for an RNA polymerase (e.g., T7). Amplification occurs exponentially in a reaction that couples transcription, reverse transcription and second-strand synthesis. In a preferred embodiment, the oligonucleotide bound to the immobilization media does not encode the promoter. A second oligonucleotide that encodes the promoter is free to diffuse throughout the media. In this way, a "one-sided" 3SR reaction is performed on the immobilized nucleic acid. The bound oligonucleotide hybridizes to the newly synthesized transcripts, which limits diffusion and primes reverse transcription, thereby producing exponential amplification.

6.8 The Array

Preferably, detection of hybridization information takes place at spatially discrete locations where tags hybridize to their complements. It is important that the detection of signals from different fractions or pools be associated with tag complement locations that can be identified throughout the procedure. Otherwise, the sequence of signals will not be a faithful representation of the mobility and/or spatial address of the polynucleotide fragments corresponding to the tag and tag complement. This requirement is met by providing a spatially addressable array of tag complements. For some embodiments, knowledge of the identity of a tag complement is not crucial; it is only important that its location be identifiable from one hybridization to another. Preferably, the regions containing tag complements are discrete, i.e., non-overlapping with regions containing different tag complements, so that signal detection is more convenient. Generally, spatially addressable arrays are constructed by attaching or synthesizing tag complements on solid phase supports. Solid phase supports for use with the invention may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Preferably, either a population of discrete particles is employed such that each particle has a uniform coating, or population, of complementary sequences of the same tag (and no other), or a single or a few supports are employed with spatially discrete regions each containing a uniform coating, or population, of complementary sequences to the same tag (and no other). In the latter embodiment, the area of the regions may vary according to particular applications;

usually, the regions range in area from several $\mu m^2$, e.g., 3-5, to several hundred $\mu m^2$, e.g., 100-500.

Tag complements are preferably polynucleotides, and they may be used with the solid phase support that they are synthesized on, or they may be separately prepared and attached to a solid phase support for use, e.g., as disclosed by Lund et al. (1988); Albretsen et al. (1990); Wolf et al. (1987); Ghosh et al. (1987); or Brown et al. (1998). Preferably, tag complements are synthesized on and used with the same solid phase support, which may comprise a variety of forms and include a variety of linking moieties. Such supports may comprise microparticles or arrays, or matrices, of regions where uniform populations of tag complements are synthesized. A wide variety of solid supports may be used with the invention, including supports made of controlled pore glass (CPG), highly cross-linked polystyrene, acrylic copolymers, cellulose, nylon, dextran, latex, polyacrolein, and the like, disclosed in the following exemplary references: Mosbach (1976); Rembaum et al. (1977); Rembaum (1983 & 1987); and Pon (1993). Solid supports further include commercially available nucleoside-derivatized CPG and polystyrene beads (e.g., available from Applied Biosystems, Foster City, Calif.); derivatized magnetic beads; polystyrene grafted with polyethylene glycol (e.g., TentaGelÔ, Rapp Polymere, Tubingen Germany); and the like. Selection of the support characteristics, such as material, porosity, size, shape, and the like, and the type of linking moiety employed depends on the conditions under which the tags are used. Exemplary linking moieties are disclosed in Pon et al. (1988); Webb (1987); Barany et al. (1993); Damha et al. (1990); Beattie et al., (1993);

Maskos et al. (1992); and the like. When tag complements are attached or synthesized on microparticles, populations of microparticles are fixed to a solid phase support to form a spatially addressable array as disclosed in Brenner (1997a, 1998b)

As mentioned above, tag complements also may be synthesized on a single (or a few) solid phase support[s] to form an array of features uniformly coated with tag complements. That is, within each feature in such an array the same tag complement is synthesized. Techniques for synthesizing such arrays are disclosed in Fodor et al. (1995); Pease et al. (1994); Southern (1997); Maskos et al. (1992); Southern et al. (1992); Maskos et al. (1993); Weiler et al. (1997); Montgomery (1998); and Singh-Gasson et al. (1999).

The invention may be implemented with microparticles or beads uniformly coated with complements of the same tag sequence. Microparticle supports and methods of covalently or noncovalently linking oligonucleotides to their surfaces are well known, as exemplified by the following references: Beaucage et al. (11992); Gait (1984); and the references cited above. Generally, the size and shape of a microparticle is not critical; however, microparticles in the size range of a few, e.g., 1-2, to several hundred, e.g., 200-1000 µm diameter are preferable, as they facilitate the construction and manipulation of large repertoires of oligonucleotide tags with minimal reagent and sample usage.

Church (1999) discloses a method for preparing a randomly-patterned array of polynucleotides, using in situ amplification methods. In a preferred embodiment, the polynucleotides are amplified in situ using the "one-sided" 3SR in situ reaction described above.

Arrays of fixed microparticles and arrays prepared by other means may be replicated according to the methods of Cantor et al. (1998) or Church (1999). In this way, even an array comprising randomly patterned tag complements of unknown sequence may be effectively utilized in some embodiments of this invention. Of course, a single array may be utilized many times, but there is always a limit. The ability to replicate a randomly patterned array relieves the experimental constraints of this limit, permitting for example hundreds of bases to be sequenced (requiring hundreds of hybridizations to the array of tag complements) according to the method of this invention.

Molecules other than polynucleotides may serve as tag complements. Gold et al. (1993 & 1995) teach methods for selecting short polynucleotides that bind to polypeptides and small molecules in a sequence-dependent manner. These short polynucleotides can be utilized as tags and the molecules to which they bind may serve as tag complements. Methods for constructing arrays of polypeptides and small molecules are disclosed by, for example Pirrung et al. (1995), Matson et al. (1995) and Montgomery (1998). In addition, the spotting methods taught by Brown et al. (1998) are readily adapted to other molecules. Methods in combinatorial chemistry (see for example Wilson et al. 1997; Gordon et al. 1998; Kirk et al. 1998; Still et al. 1996; Horlbeck, 1999) can be used to construct large collections of these molecules such that only one molecular species is attached to any one, separate solid support (e.g., a bead). These species may be arrayed as described above for polynucleotides. Tags that hybridize optimally to these tag complements may be selected en masse as described above for polynucleotide tag complements.

6.9 Detecting Hybridization to the Array

Methods for hybridizing polynucleotides to arrays of complementary polynucleotides are well known in the art. See for example (Lockhart et al., 1996; Wang et al., 1988; Eisen et al., 1999; Duggan et al., 1999; Saiki et al., 1989).

Polynucleotides hybridized to the array may be visualized in several different ways. To facilitate detection, various methods for labeling DNA and constructing labeled oligonucleotides are known in the art. Representative methods include Mathews et al. (1988), Haugland (1996), Keller et al. (1993), Eckstein (1991), Jablonski et al. (1986), Agrawal et al. (1992), Menchen et al. (1993), Cruickshank (1992), Urdea (1992) and Lee et al. (1999). Labels include for example radioactive isotopes, fluorescent compounds such as fluorescein and rhodamine, chemiluminescent compounds, quantum dots (e.g. see Bruchez et al., 1998; and Chan et al., 1998) and mass tags (e.g. Xu et al., 1997; Schmidt, 1999). The polynucleotides may be coupled to various enzymes (e.g., β-galactosidase, horseradish peroxidase and alkaline phosphatase) and the enzymatic activity is detected with the proper substrate (e.g., X-gal, DAB and BCIP, see Ausubel et al., 1997). The label can be incorporated directly into polynucleotides, e.g. tagged amplicons, prior to hybridization to the array. The label may also be incorporated during an extension reaction of polynucleotides after hybridization to the array in which either the tag complements or the hybridized polynucleotides act as primers for polymerase (see, for example, Pastinen et al., 1997)

Another method to visualize a tagged polynucleotide hybridized to its tag complement is to hybridize a third labeled polynucleotide to the tagged polynucleotide. This third polynucleotide may be ligated to the tag complement to increase hybridization specificity in a reaction analogous to the "oligonucleotide ligation reaction (OLA)", see Landegren et al. (1988). Alternatively, "oligonucleotide stacking" effects of the third oligonucleotide can be used to increase duplex stability, see e. Lane et al. (1997).

Any imaging system can be utilized that is capable of detecting the label or labels, with a resolution appropriate to the size of the array features. Numerous examples of imaging apparatus are known in the art. For example, Trulson et al. (1998), Pirrung et al. (1992), and Dorsel et al. (1999) describe imaging systems for fluorescent labels. Commercial apparatus are available, eg. ScanArray 4000 (General Scanning), Biochip Imager (Hewlett Packard), GMS 418 Array Scanner (Genetic Microsystems), GeneTAC 1000 (Genomic Solutions), Chip Reader (Virtek). Phosphorimager systems are available for detecting radiolabels, e.g. Cyclone (Packard Instrument company) and BAS-5000 (Fujifilm).

6.10 Applications and Uses of Parallel Methods for Genomic Analysis

A sequenced polynucleotide can be utilized in a variety of ways to manipulate and discover information about biological systems, for example expression profiling, drug discovery, gene therapy, disease diagnosis, disease treatment, characterization of biological circuitry and so on. For some examples and methodologies see, Hawkins et al. (1996), Hastings et al. (1996), Guegler et al. (1997), Wachsman et al. (1997), Popoff et al. (1997), Carraway et al. (1997), Li et al. (1997), Au-Young et al. (1998), Hillman et al. (1998), Wei et al. (1998), Levinson et al. (1998); Gimeno et al. (1999), Sutcliffe et al. (1999), Wei et al. (1999), Goodearl (1999), Kleyn et al. (1999), Lee et al. (1999), and Oin (1999) which are hereby incorporated by reference in their entirety.

One method according to the invention includes the insertion of a nucleic acid, the sequence of which has been determined according to methods of the invention described above, into a vector. The double-stranded form of the nucleic acid generally is inserted into the vector by any of a variety of standard molecular cloning techniques (see, e.g., Sambrook et al., 1989). The nucleic acid can be inserted into the vector in either of the two possible orientations: transcription of this sequence yield either a "sense" transcript (i.e., an mRNA sequence actually produced in cells expressing the corresponding gene) or an "antisense" transcript (the complement of an mRNA sequence actually produced). Conveniently, the vector is cleaved with a restriction endonuclease, and the separated nucleic acid or fragment is ligated into the vector at the corresponding restriction endonuclease recognition site. In one embodiment, the nucleic acid sequence obtained according to the invention contains all coding sequences that encode a protein or is inserted into the vector as part of a larger nucleic acid sequence that contains all such coding sequences.

A wide variety of suitable vectors is available, including vectors derived from bacterial and yeast plasmids as well as from viruses, e.g., cosmids, plasmids, phage derivatives, and phagemids. Examples of bacterially derived vectors include: pBS, phagescript, PsiX174, pBluescript SK, pBs KS, pNH8a, pNH16a, pNH18a, and pNH46a, which are commercially available from Stratagene, and pTrc99A, pKK223-3, pKK233-3, pDR540, and pRIT5, which are commercially available from Pharmacia. Examples of eukaryotic vectors include: pWLneo, pSV2cat, pOG44, PXTI, which are commercially available from Stratagene, and pSVK3, pBPV, pMSG, and pSVL, which are commercially available from Pharmacia. However any vector capable of replicating in a host cell can be employed. A vector generally has a selectable marker to ensure that the vector will be maintained in host cells. Suitable markers include, for example, those conferring resistance to tetracycline or ampicillin (useful in prokaryotic cells) and neomycin (useful in eukaryotic cells).

The vector can be used simply to propagate the nucleic acid or can be specially adapted for particular functions. Examples of the latter include probe generation vectors and expression vectors. An expression vector allows the expression of an amino acid sequence encoded in a nucleic acid or fragment. Typically the latter is operatively linked to an expression control sequence (e.g., a promoter). The term "operatively linked" is used herein to denote a relationship in which the expression control sequence directs the synthesis of mRNA encoding the amino acid sequence to be expressed. This term does not imply that the expression control sequence is necessarily linked directly to the nucleic acid or fragment. Any promoter known or determined to direct transcription of prokaryotic, eukaryotic, or viral genes can be employed. Exemplary promoters include the *E. coli* lac or trp promoters, the early and late SV40 promoters, the CMV immediate early promoter, the HSV thymidine kinase promoter, and the lambda phage $P_R$ and $P_L$ promoters.

Expression vectors also may contain an enhancer sequence, i.e., a "cis-acting" DNA element that acts on a promoter to increase transcription. Exemplary enhancers include those derived from SV40, CMV, polyoma, and adenovirus. Generally, enhancers are located upstream of and within about 100-300 bp of the promoter. Expression vectors can also contain splice donor and acceptor sites, polyadenylation sites, and translation initiation and termination sequences in appropriate phase with the coding sequence to be expressed. A signal sequence is conveniently included if it is not already present in the coding sequence and secretion of the encoded polypeptide (into the culture medium or periplasmic space) is desired. In one embodiment, an expression vector contains a nucleotide sequence that promotes amplification of the vector in a host cell under appropriate culture conditions (e.g., culturing in the presence of methotrexate for vectors including the dihydrofolate reductase gene).

In one method, a vector of the invention is introduced into a host cell. The host cell can, for example, be a prokaryote, a lower eukaryote (e.g., a fungal cell), or a higher eukaryote (e.g., a mammalian cell). Exemplary prokaryotic host cells include *E. coli, Bacillus subtilis, Salmonella typhimurium*, and various species within the genera *Pseudomonas, Streptomyces*, and *Staphylococcus*, although a wide variety of others can be employed. Exemplary eukaryotic cells include yeast cells and higher eukaryotic cells such as CHO, COS, or Bowes melanoma cells. The host cell employed varies depending on the vector, and the selection of a suitable host cell-vector system is within the level of skill in the art. When the vector is an expression vector, the host cell is typically a mammalian cell, an insect cell, a plant cell, a fungal cell (e.g., a yeast), or a bacterial cell.

A variety of host-expression vector systems may be utilized to express the gene coding sequences of the invention. Such host-expression systems represent vehicles by which the coding sequences of interest may be produced and subsequently purified, but also represent cells which may, when transformed or transfected with the appropriate nucleotide coding sequences, exhibit the gene product of the invention in situ. These include but are not limited to microorganisms such as bacteria (e.g., *E. coli, B. subtilis*) transformed with recombinant bacteriophage DNA, plasmid DNA or cosmid DNA expression vectors containing the gene product coding sequences; yeast (e.g., *Saccharomyces, Pichia*) transformed with recombinant yeast expression vectors containing the gene product coding sequences; insect cell systems infected with recombinant virus expression vectors (e.g., baculovirus) containing the gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions of the protein or for raising antibodies to the protein, vectors which direct the expression of high levels of fusion protein products that are readily purified may be desirable. Such vectors include, but are not limited, to the *E. coli* expression vector pUR278 (Ruther et al., 1983), in which the gene product coding sequence may be ligated individually into the vector in frame with the lac Z coding region so that a fusion protein is produced; pIN vectors (Inouye et al., 1985; Van Heeke et al., 1989); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The gene coding sequence may be cloned individually into non-essential regions (for example the polyhedrin gene) of the virus and placed under control of an AcNPV promoter (for example the polyhedrin promoter). Successful insertion of the gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983; Smith et al., U.S. Pat. No. 4,745,051).

In mammalian host cells, a number of viral-based expression systems may be utilized. In cases where an adenovirus is used as an expression vector, the gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts. (e.g., see Logan et al., 1984). Specific initiation signals may also be required for efficient translation of the inserted gene product coding sequences. These signals include the ATG initiation codon and adjacent sequences. In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, and in particular, T cell lines such as, for example, Jurkat, CTLL, HT2, Dorris, D1.1, AE7, D10.G4 and CDC25.

The vector can be introduced into the host cell by any effective technique, such as transformation, transfection, infection, or transduction. Convenient transfection techniques include calcium phosphate transfection, DEAE-dextran-mediated transfection, and electroporation. The host cell containing the vector then can be cultured in a conventional nutrient medium, modified as appropriate for selecting vector-containing cells, inducing or derepressing a promoter, and/or amplifying a vector DNA sequence. Otherwise, the culture conditions employed, such as pH and temperature, are those suitable for the particular host cell. Suitable culture conditions are known to, or can be readily determined, by those skilled in the art. If desired, vector DNA can be prepared from a host cell culture using any of a number of standard techniques.

A host cell containing an expression vector can be cultured under conditions that allow expression of the encoded polypeptide. Typically, host cells are allowed to grow to an appropriate density, and then a promoter linked to the nucleic acid to be expressed is induced or derepressed (e.g., by temperature shift or chemical induction) and/or a linked enhancer is activated. The host cells are cultured for an additional period and then harvested, typically by centrifugation. If the expressed polypeptide was secreted into the culture medium, the polypeptide is recovered from the culture medium. Alternatively, if the expressed polypeptide was retained in the host cells, the cells are disrupted by physical or chemical means, and the polypeptide is recovered from the resulting crude extract.

The polypeptide can be purified from the culture medium or crude extract using standard protein purification techniques. Suitable methods include ammonium sulfate or ethanol precipitation, acid extraction, anion or cation exchange chromatography, phosphocellulose chromatography, hydrophobic interaction chomatography, affinity chomatography, hydroxylapatite chromatography, and lectin chromatography, etc., and combinations thereof. The purification strategy also may include a protein refolding step to provide a polypeptide having the proper structure. High performance liquid chromatography can be employed, typically as one of the final purification steps. Depending on the method of production, the polypeptide can have methionine as the initial amino acid residue and can be glycosylated or non-glycosylated.

In an alternative embodiment, a polypeptide is expressed by translating an mRNA corresponding to a nucleic acid whose sequence has been determined according to the methods of the invention in a cell-free translation system.

The amino acid sequence of a polypeptide encoded by a nucleic acid whose sequence has been determined according to the methods of the invention can be compared to that of previously characterized polypeptides to identify one or more biological functions of the polypeptide. A comparison of the nucleotide sequence of a selected amino acid with the nucleotide sequence of previously characterized genes can also indicate a biological function. Biological functions of particular interest include the ability to bind to a ligand or a receptor, the ability to form an ion channel, the ability to couple with a GTP-binding protein, the ability to phosphorylate or be phosphorylated by another polypeptide, and to otherwise modulate the activity of another molecule that plays a role in a signal transduction pathway.

The polypeptide or a fragment thereof can be employed in a screening assay to identify compounds and/or molecules that stimulate (agonists) or inhibit (antagonists) the biological function of the polypeptide. In addition, if the identified biological function includes a binding activity, the polypeptide can be employed in an assay to detect the presence of the binding partner in cells or tissues.

Moreover, the polypeptide can be used to generate antibodies that stimulate or inhibit the activity of the polypeptide or that bind the polypeptide without affecting activity. As used herein, the term "antibody" refers to a molecule including any binding-competent portion of an antibody, such as, for example, a single chain antibody or a Fab fragment. The term encompasses molecules in which such binding competent portions are covalently attached to other polypeptide sequences, as in dual-specificity antibodies. An antibody specific for the polypeptide can be polyclonal or monoclonal. Polyclonal antibodies are produced by immunizing an animal, preferably a mammal, with the polypeptide or an immunogenic fragment thereof and collecting the antiserum. The antiserum can be screened for the desired binding activity, and antibodies with undesirable cross-reactivities can be removed by contacting the antiserum with the corresponding agent(s) and recovering the non-bound component of the antiserum. Monoclonal antibodies can be produced by any convenient technique, including the hybridoma technique (Kohler et al., 1975), the trioma technique, the human B-cell hybridoma technique (Kozbor et al., 1983), and the EBV-hybridoma technique, which produces human monoclonal antibodies (Cole et al., 1985). Humanized antibodies can be produced using a transgenic animal, and single chain antibodies can be produced as described by Ladner et al. (1990). Antibodies that specifically bind a polypeptide encoded by a nucleic acid whose sequence has been determined according to the methods of the invention are useful in affinity purification of the polypeptide and for detecting the presence of and/or quantitating the amount of a polypeptide in a sample. For instance, antibodies can be employed in immunohistochemistry studies to determine the localization of the polypeptide in cells of a tissue sample. In such studies, the polypeptide-specific antibody is labeled with a detectable label, such as, for example, an enzyme label. The label can be attached to the polypeptide-specific antibody directly or indirectly (e.g., attachment to a secondary antibody specific for the polypeptide-specific antibody). Antibody binding generally is detected by adding a substrate for the enzyme and detecting conversion of the substrate to a product, usually via a color change.

In yet another embodiment of the invention, sequences determined according to the method of the invention may be used to design probes useful for detecting the presence of a nucleic acid sequence complementary to the probe sequence. The detection of such sequences can provide the basis of diagnostic tests, or alternatively, may be useful for basic research purposes. Such probe sequences may be synthesized using a commercially available nucleic acid synthesizer, such as the ABI Model 394 or may be generated from restriction fragments of the cloned library element from which the sequence was determined, and sub-cloning the restriction fragment into a probe vector such as, e.g., pBluescript SK (Stratagene), pSP72 (Promega), M13 mp18 (New England Biolabs) and the like. The cloned library element from which the sequence was determined may be recovered by a variety of methods, including probing the library with the tag sequence corresponding to the desired sequence, or immobilizing the tag sequence (or its complement) on a solid support, and hybridizing the library with the solid support to specifically recover the desired library element. Such methods are well known in the art, see e.g. Ausubel (1997) and Brenner (1997a). In addition, multiple probes may be arrayed (e.g. Brown, 1998) or may be synthesized as oligonucleotides in an array (e.g. Fodor et al., 1995) as described above in section 6.8.

Sequences determined according to the method of the invention also may be used to design primers for amplification of nucleic acid molecules via methods such as, e.g., PCR. Designing PCR primers from known sequences is well within the art. Relevant considerations are discussed in, e.g., Dieffenbach et al. (1995) and Innis et al. (1990). PCR, using primers designed from sequences determined according to the method of the invention, may be used as the basis of a diagnostic test to determine the presence of a nucleic acid sequence in a sample, or, alternatively, simply to provide large quantities of nucleic acid for other uses.

6.10.1 Polynucleotide Homologs

Another method according to the invention involves identifying polynucleotides that are homologous at the nucleotide or encoded amino acid level to a parent polynucleotide or parent gene sequenced by the methods described above. Homologs may be isolated from the same species as the parent polynucleotide or from a different species. Homologs may not occur naturally, but instead they may be constructed from the parent polynucleotide by random or site-directed mutagenesis as described below. By definition the parent polynucleotide is a homolog of itself.

A highly homologous, polynucleotide preferably exhibits at least about 80% overall similarity at the nucleotide level to the parent polynucleotide, more preferably exhibits at least about 85-90% overall similarity, and most preferably exhibits at least about 95% overall similarity to the parent polynucleotide. However, because of the degeneracy of the genetic code, two polynucleotides that encode highly homologous polypeptides may not necessarily exhibit extensive similarity at the nucleotide level. In particular, site directed mutagenesis can be used to produce two polynucleotides that encode the same polypeptide, but share less than 67% similarity at the nucleotide level.

Homologous polynucleotides, exhibiting extensive homology to one or more domains of the parent polynucleotide can be identified and readily isolated, without undue experimentation, by molecular biological techniques well known in the art. Further, there can exist homologous genes at other genetic loci within the genome that encode proteins which have extensive homology to one or more domains encoded by a parent gene. These genes can also be identified via similar techniques. Still further, there can exist alternatively spliced variants of the parent gene.

As an example, in order to clone a human gene homolog or variants using a sequenced murine polynucleotide, the murine polynucleotide or sequence element is labeled and used to screen a cDNA library constructed from mRNA obtained from appropriate cells or tissues derived from the organism (in this case, human) of interest. The hybridization and wash conditions used should be of a low stringency when the cDNA library is derived from a different type of organism than the one from which the labeled sequence was derived. Low stringency conditions are well known to those of skill in the art, and will vary predictably depending on the specific organisms from which the library and the labeled sequences are derived. For guidance regarding such conditions see, for example, Sambrook et al. (1989) and Ausubel et al (1989).

With respect to the cloning of a human homolog, using a murine polynucleotide, for example, various stringency conditions which promote DNA hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M $NaHPO_4$ (pH 7.2)/1 mM EDTA/7% SDS, or hybridization in 50% formamide/0.25M $NaHPO_4$ (pH 7.2)/0.25 M NaCl/1 mM EDTA/7% SDS; followed by washing in 40 mM $NaHPO_4$ (pH 7.2)/1 mM EDTA/5% SDS at 50° C. or in 40 mM $NaHPO_4$ (pH 7.2) 1 mM EDTA/1% SDS at 50° C. Both temperature and salt may be varied, or alternatively, one or the other variable may remain constant while the other is changed.

Alternatively, the labeled fragment may be used to screen a genomic library derived from the organism of interest, again, using appropriately stringent conditions well known to those of skill in the art.

Further, a homologous polynucleotide may be isolated from nucleic acid of the organism of interest by performing PCR using two degenerate oligonucleotide primer pools designed on the basis of amino acid sequences within the parent polynucleotide as described by e.g. Innis et al. (1990) and Wilkie et al. (1994). The template for the reaction may be genomic DNA or cDNA obtained by reverse transcription of mRNA prepared from, for example, human or non-human cell lines or tissue known or suspected to express the polynucleotide.

The PCR product may be subcloned and sequenced to ensure that the amplified sequences represent homologous polynucleotides. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

Homologous polynucleotides of the invention further include isolated polynucleotides which hybridize under highly stringent or moderate stringent conditions to at least about 6, preferably about 12, more preferably about 18, consecutive nucleotides of the parent polynucleotide. The invention also includes polynucleotides, preferably DNA molecules, that hybridize to, and are therefore the complements of, the parent polynucleotide. Such hybridization conditions may be highly stringent or moderately stringent, as described above. In instances wherein the nucleic acid molecules are short oligonucleotides highly stringent conditions may refer, e.g., to washing in 6×SSC/50 mM sodium pyrophosphate at 37° C. (for 14-base oligos), 48° C. (for 17-base oligos), 55° C. (for 20-base oligos), and 60° C. (for 23-base oligos). These nucleic acid molecules may encode or act as antisense molecules useful, for example, in gene regulation. Further, such sequences may be used as part of ribozyme and/or triple helix sequences, also useful for gene regulation. Still further, such molecules may be used as components of diagnostic methods whereby, for example, the presence of a particular allele or alternatively spliced transcript responsible for a mutant phenotype may be detected.

PCR technology may be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al. (1989) and Ausubel et al. (1997).

6.10.2 Expression Analysis

Quantitative and qualitative aspects of gene expression of polynucleotides sequenced according to this invention can also be assayed. For example, RNA from a cell type or tissue known, or suspected, to express a gene may be isolated and tested utilizing hybridization or PCR techniques. The isolated cells can be derived from cell culture or from a patient. The analysis of cells taken from culture may be a necessary step in the assessment of cells to be used as part of a cell-based gene therapy technique or, alternatively, to test the effect of compounds on the expression of the gene. Such analyses may reveal both quantitative and qualitative aspects of the expression pattern of the gene, including activation or inactivation of gene expression and presence of alternatively spliced transcripts.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Such RT-PCR techniques can be utilized to detect differences in transcript size which may be due to normal or abnormal alternative splicing. Additionally, such techniques can be performed using standard techniques to detect quantitative differences between levels of full length and/or alternatively spliced transcripts detected in normal individuals relative to those individuals exhibiting a phenotype of interest.

In the case where detection of specific alternatively spliced species is desired, appropriate primers and/or hybridization probes can be used, such that, in the absence of such sequence, no amplification would occur. Primers are chosen which will yield fragments of differing size depending on whether a particular exon is present or absent from the transcript being utilized.

As an alternative to amplification techniques, standard Northern analyses can be performed if a sufficient quantity of the appropriate cells can be obtained. Utilizing such techniques, quantitative as well as size related differences between transcripts can also be detected.

Additionally, it is possible to perform such gene expression assays "in situ", i.e., directly upon tissue sections (fixed and/or frozen) of patient tissue obtained from biopsies or resections, such that no nucleic acid purification is necessary. Nucleic acid reagents such as those described in Section 6.1 may be used as probes and/or primers for such in situ procedures (see, for example, Nuovo, 1992).

Gene expression may also be assayed "en masse" utilizing polynucleotide arrays (see for example Lockhardt, 1996; Schena et al., 1995; etc.). Sequence from polynucleotides can be used to design arrays for synthesis or to determine the identity of the polynucleotides at any particular address in the array.

Another method to assay gene expression en masse is simply to sequence cDNA from a cell population by the massively parallel method described above. This technique can be coupled with a second parallel method such as SAGE (serial analysis of gene expression, Velculescu et al., 1995) to permit analysis of even the rarest transcripts with a single sequencing reaction. cDNA from different sources (for example diseased vs. normal tissue, cells with and without drug, tissue from different developmental states, etc.) can be compared to determine the differentially expressed genes (see e.g. Kozian et al., 1999).

6.10.3 Screening Assays for Compounds that Modulate the Activity of a Gene Product Screening assays may be designed to identify compounds capable of interacting with, e.g., binding to, a polypeptide or gene product that is sequenced and characterized as described above. Methods are well known in the art, see for example Wolff (1995), Foye et al. (1995), and Hansch et al. (1990). The following assays are designed to identify: (i) compounds that bind to gene products; (ii) compounds that bind to other intracellular proteins that interact with a gene product; (iii) compounds that interfere with the interaction of a gene product with other intracellular proteins; and (iv) compounds that modulate the activity of a gene (i.e., modulate the level of gene expression and/or modulate the level of a gene product activity). Compounds may include, but are not limited to, peptides such as, for example, soluble peptides, and small organic or inorganic molecules. Methods for synthesizing compounds are well known in the art. Combinatorial synthesis and other high throughput synthesis methods as well as high throughput screening assays have been described, see for example, Wolff (1995), Burnbaum et al. (1999), Parce et al. (1999), Chelsky et al. (1999); Horlbeck (1999); Devlin (1997); Venton et al. (1998); Kirk et al. (1998); and Still et al. (1996).

Assays additionally may be utilized which identify compounds that bind to gene regulatory sequences (e.g., promoter sequences), see e.g., Platt (1994), which may modulate the level of gene expression. Methods for the identification of such intracellular proteins are described below.

Compounds identified via assays such as those described herein may be useful, for example, in elaborating the biological function of a gene product, and for ameliorating symptoms of disease. It is to be noted that the invention includes methods to identify such pharmaceutical compositions pertaining to polynucleotides characterized according to the invention. Such pharmaceutical compositions can be formulated, for example, as discussed below.

6.10.4 In vitro Screening Assays for Compounds that Bind to a Gene Product

In vitro systems may be designed to identify compounds capable of interacting with, e.g., binding to, a polypeptide that is sequenced and characterized according to this invention. Compounds identified may be useful, for example, in modulating the activity of wild type and/or mutant gene products, may be useful in elaborating the biological function of the a gene product, may be utilized in screens for identifying compounds that disrupt normal gene product interactions, or may in themselves disrupt such interactions.

The principle of the assays used to identify compounds that interact with a gene product involves preparing a reaction mixture of the gene product and the test compound under conditions and for a time sufficient to allow the two components to interact with, e.g., bind to, thus forming a complex, which can represent a transient complex, which can be removed and/or detected in the reaction mixture. These assays can be conducted in a variety of ways. For example, one method to conduct such an assay would involve anchoring a gene product or the test substance onto a solid phase and detecting the gene product/test compound complexes anchored on the solid phase at the end of the reaction. In one embodiment of such a method, the gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the gene product or the test compound to anchor any complexes formed in solution, and a labeled antibody specific for the other component of the possible complex to detect anchored complexes.

6.10.5 Rational Design of Compounds that Interact with a Gene Product

The 3-dimensional structure of a gene product can be determined empirically using techniques such as crystallography (see for example, McRee, 1999; Drenth, 1999) and NMR (see for example, Cavanagh et al., 1996; Krishna et al., 1999). In some cases, the structure can be predicted from the primary amino acid sequence by homology comparisons to known structures.

Knowledge of the 3-dimensional structure permits rational design of compounds that may interact with and influence the activity of the gene product, see for example Veerapandian (1995); Martin (1989); Keseru et al. (1999); Weiner, D. B. et al., (1994), and Weiner, D. B. et al. (1995).

6.10.6 Assays for Intracellular Proteins that Interact with a Gene Product

Any method suitable for detecting protein-protein interactions may be employed to identify intracellular proteins that interact with a gene product characterized according to the method of this invention. Among the traditional methods which may be employed are co-immunoprecipitation, crosslinking and co-purification through gradients or chromatographic columns. Utilizing procedures such as these allows for the isolation of intracellular proteins which interact with gene products. Once isolated, such an intracellular protein can be identified and can, in turn, be used, in conjunction with standard techniques, to identify additional proteins with which it interacts.

Additionally, methods may be employed which result in the simultaneous identification of genes which encode the intracellular protein interacting with the gene product. These methods include, for example, probing expression libraries with the labeled gene product, using the labeled protein in a manner similar to the well known technique of antibody probing of λgt11 libraries.

One method which detects protein interactions in vivo, the two-hybrid system, is described in detail for illustration only and not by way of limitation. One version of this system has been described (Chien et al., 1991) and is commercially available from Clontech (Palo Alto, Calif.).

Briefly, utilizing such a system, plasmids are constructed that encode two hybrid proteins: one consists of the DNA-binding domain of a transcription activator protein fused to the characterized gene product and the other consists of the transcription activator protein's activation domain fused to an unknown protein that is encoded by a cDNA which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. Total genomic or cDNA sequences are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. Positive colonies are purified and the library plasmids responsible for reporter gene expression are isolated. DNA sequencing then is used to identify the proteins encoded by the library plasmids.

For example, the bait gene product can be cloned into a vector such that it is translationally fused to the DNA encoding the DNA-binding domain of the GAL4 protein. A cDNA library of the cell line from which proteins that interact with the bait gene product are to be detected can be made using methods routinely practiced in the art. The cDNA fragments can be inserted into a vector such that they are translationally fused to the transcriptional activation domain of GAL4. This library can be co-transformed along with the bait gene-GAL4 fusion plasmid into a yeast strain which contains a lacZ gene driven by a promoter which contains GAL4 activation sequence. A cDNA encoded protein, fused to GAL4 transcriptional activation domain, that interacts with the bait gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait gene-interacting protein using techniques routinely practiced in the art.

6.10.7 Assays for Compounds that Interfere with the Interaction Between a Gene Product and an Intracellular Macromolecule A characterized gene product of the invention may, in vivo, interact with one or more intracellular macromolecules, such as proteins. Such macromolecules may include, but are not limited to, nucleic acid molecules and those proteins identified via methods such as those described above. For purposes of this discussion, such intracellular macromolecules are referred to herein as "interacting partners." Compounds that disrupt interactions in this way may be useful in regulating the activity of the gene product, including mutant gene products. Such compounds may include, but are not limited to molecules such as peptides, and the like, as described above, which would be capable of gaining access to the intracellular gene product.

The basic principle of the assay systems used to identify compounds that interfere with the interaction between the gene product and its intracellular interacting partner or partners involves preparing a reaction mixture containing the gene product, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the gene product and its intracellular interacting partner. Control reaction mixtures are incubated without the test compound or with a placebo. The formation of any complexes between the gene product and the intracellular interacting partner is then detected. The formation of a complex in the control reaction, but not in the reaction mixture containing the test compound, indicates that the compound interferes with the interaction of the gene protein and the interacting partner. Additionally, complex formation within reaction mixtures containing the test compound and normal gene product may also be compared to complex formation within reaction mixtures containing the test compound and a mutant gene product. This comparison may be important in those cases wherein it is desirable to identify compounds that disrupt interactions of mutant but not normal gene products.

The assay for compounds that interfere with the interaction of the gene product and interacting partners can be conducted in a heterogeneous or homogeneous format. Heterogeneous assays involve anchoring either the gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the gene product and the interacting partners, e.g., by competition, can be identified by conducting the reaction in the presence of the test substance; i.e., by adding the test substance to the reaction mixture prior to or simultaneously with the gene product and intracellular interacting partner. Alternatively, test compounds that disrupt pre-formed complexes, e.g. compounds with higher binding constants that displace one of the components from the complex, can be tested by adding the test compound to the reaction mixture after complexes have been formed. The various formats are described briefly below.

In a heterogeneous assay system, either the gene product or the interacting partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the gene product or interacting partner and drying. Alternatively, an immobilized antibody specific for the species to be anchored may be used to anchor the species to the solid surface. The surfaces may be prepared in advance and stored.

To conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the interacting components to anchor any complexes formed in solution, and a labeled antibody specific for the other partner to detect anchored complexes. Again, depending upon the order of addition of reactants to the liquid phase, test compounds which inhibit complex or which disrupt pre-formed complexes can be identified.

In an alternate embodiment of the invention, a homogeneous assay can be used. In this approach, a pre-formed complex of the gene protein and the interacting partner is prepared in which either the gene product or its interacting partner is labeled, but the signal generated by the label is quenched due to complex formation (see, e.g., Rubenstein et al. (1980) which utilizes this approach for immunoassays). The addition of a test substance that competes with and displaces one of the species from the pre-formed complex will result in the generation of a signal above background. In this way, test substances which disrupt the gene product/intracellular interacting partner interaction can be identified.

In a particular embodiment, the gene product can be prepared for immobilization using recombinant DNA techniques described above. For example, the gene product coding region can be fused to a glutathione-S-transferase (GST) gene using a fusion vector, such as pGEX-5x-1, in such a manner that its interacting activity is maintained in the resulting fusion protein. The intracellular interacting partner can be purified and used to raise a monoclonal antibody, using methods routinely practiced in the art and described above. This antibody can be labeled with the radioactive isotope $^{125}$I, for example, by methods routinely practiced in the art. In a heterogeneous assay, e.g., the GST-gene product fusion protein can be anchored to glutathione-agarose beads. The intracellular interacting partner can then be added in the presence or absence of the test compound in a manner that allows interaction, e.g., binding, to occur. At the end of the reaction period, unbound material can be washed away, and the labeled monoclonal antibody can be added to the system and allowed to bind to the complexed components. The interaction between the gene product and the intracellular interacting partner can be detected by measuring the amount of radioactivity that remains associated with the glutathione-agarose beads. A successful inhibition of the interaction by the test compound will result in a decrease in measured radioactivity.

Alternatively, the GST fusion protein and the intracellular interacting partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the gene product/interacting partner interaction can be detected by adding the labeled antibody and measuring the radioactivity associated with the beads.

In another embodiment of the invention, these same techniques can be employed using peptide fragments that correspond to the binding domains of the gene product and/or the intracellular interacting partner, in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interacting, e.g., binding. Alternatively, one protein can be anchored to a solid surface using methods described in this Section above, and allowed to interact with, e.g., bind, to its labeled interacting partner, which has been treated with a proteolytic enzyme, such as trypsin. After washing, a short, labeled peptide comprising the interacting, e.g., binding, domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, the gene product can be anchored to a solid material as described, above, in this Section by making a GST fusion protein and allowing it to bind to glutathione agarose beads. The interactive intracellular binding partner can be labeled with a radioactive isotope, such as $^{35}S$, and cleaved with a proteolytic enzyme such as trypsin. Cleavage products can then be added to the anchored GST fusion protein and allowed to bind. After washing away unbound peptides, labeled bound material, representing the intracellular interacting partner binding domain, can be eluted, purified, and analyzed for amino acid sequence by well-known methods. Peptides so identified can be produced synthetically or fused to appropriate facilitative proteins using recombinant DNA technology.

In another embodiment, a two-hybrid screening assay could be used to identify drugs that block the interaction between the gene product and an interacting partner (see for example Vidal et al., 1999). This strategy would employ a two-hybrid containing yeast strain whose growth on synthetic complete medium lacking L-histidine is conditional on the physical interaction between the gene product and an interacting partner. In one example of such an embodiment, the strain would be spread in a thin lawn on a plate made of synthetic complete medium lacking L-histidine. Filter disks containing test compounds would be applied to the plates. Most test compounds would not affect the interaction between the gene product and the interacting partner and consequently a confluent lawn of yeast would grow around the disks impregnated with such compounds. Test compounds that inhibit the interaction would block growth of the yeast strain around the filter disks containing them causing zones of growth inhibition. Those compounds could then be tested against wild-type yeast to confirm that they are not simply fungistatic or fungicidal. Such an embodiment can also be performed in liquid culture, utilizing standard well known methods for measuring cell growth in culture.

6.10.8 Assays for Molecules that Affect the Expression of a Gene Product

A variety of methods may be employed to influence the expression of a gene that is sequenced and characterized according to the methods of this invention. The influence of compounds such as peptides and small molecules on gene expression may be assayed by for example simple Northern analysis, hybridization of cDNA or mRNA to oligonucleotide arrays (see e.g., Farr et al., 1998; and Marton et al., 1998), or global monitoring of gene expression with a reporter gene coupled to different promoters as described by e.g., Ashby et al., (1996).

Antisense and ribozyme methods can be effective in influencing the expression of one or a limited number of genes. Antisense approaches involve the design of oligonucleotides (either DNA or RNA) that are complementary to the gene mRNA. The antisense oligonucleotides will bind to the complementary gene mRNA transcripts and prevent translation. Perfect complementarity, although preferred, is not required.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well, see generally, Wagner (1994). Thus, oligonucleotides complementary to either the 5'- or 3'-non-translated, non-coding regions of the gene could be used in an antisense approach to inhibit translation of the endogenous gene mRNA.

Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'-regions or coding region of target or pathway gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein.

Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989; Lemaitre et al., 1987; Tullis, 1990) or the blood-brain barrier (see, e.g., Pardridge et al., 1989), hybridization-triggered cleavage agents (see, e.g., van der Krol et al., 1988) or intercalating agents (see, e.g., Zon, 1988). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., 1987). The oligonucleotide is a 2'-β-methylribonucleotide (Inoue et al., 1987a), or a chimeric RNA-DNA analogue (Inoue et al., 1987b).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988), methylphosphonate oligonucleotides can be prepared by use of controlled pore glass polymer supports (Sarin et al., 1988), etc.

The antisense molecules should be delivered to cells which express the gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells will result in the transcription of sufficient amounts of single stranded RNAs that will form complementary base pairs with the endogenous gene transcripts and thereby prevent translation of the gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in cells. Expression of the sequence encoding the antisense RNA can be by any promoter known in the art to act in the appropriate cells. Such promoters can be inducible or constitutive. Such promoters include but are not limited to: the SV40 early promoter region (Bernoist et al., 1981), the promoter contained in the 3' long terminal repeat of Rous sarcoma virus (Yamamoto et al., 1980), the herpes thymidine kinase promoter (Wagner et al., 1981), the regulatory sequences of the metallothionein gene (Brinster et al., 1982), etc. Any type of plasmid, cosmid, YAC or viral vector can be used to prepare the recombinant DNA construct which can be introduced directly into the tissue site. Alternatively, viral vectors can be used which selectively infect the desired cells.

Ribozymes are enzymatic RNA molecules capable of catalyzing the specific cleavage of RNA (For a review see, for example Rossi, 1994). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see Cech et al. (1992). As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave the gene mRNA transcripts can also be used to prevent translation of the gene mRNA and expression of target or pathway gene. (See, e.g. Cech, et al. 1990; Sarver et al., 1990). While ribozymes that cleave mRNA at site specific recognition sequences can be used to destroy the gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully by Haseloff et al. (1988). Preferably the ribozyme is engineered so that the cleavage recognition site is located near the 5' end of the gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Cech and collaborators (see, e.g. Zaug et al., 1984; Zaug et al., 1986a; Zaug et al., 1986b; Cech et al, 1991; Cech, 1986). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the gene.

As in the antisense approach, the ribozymes can be composed of modified oligonucleotides (e.g. for improved stability, targeting, etc.) and should be delivered to cells which express the gene of interest in vivo. A preferred method of delivery involves using a DNA construct "encoding" the ribozyme under the control of a strong constitutive promoter, so that transfected cells will produce sufficient quantities of the ribozyme to destroy endogenous gene messages and inhibit translation. Because ribozymes unlike antisense molecules, are catalytic, a lower intracellular concentration is required for efficiency.

In instances wherein the antisense, ribozyme, and/or triple helix molecules described herein are utilized to inhibit mutant gene expression, it is possible that the technique can also efficiently reduce or inhibit the transcription (triple helix) and/or translation (antisense, ribozyme) of mRNA produced by normal target gene alleles that the possibility can arise wherein the concentration of normal target gene product present can be lower than is necessary for a normal phenotype. In such cases, to ensure that substantially normal levels of target gene activity are maintained, therefore, nucleic acid molecules that encode and express target gene polypeptides exhibiting normal target gene activity can be introduced into cells via gene therapy methods that do not contain sequences susceptible to whatever antisense, ribozyme, or triple helix treatments are being utilized. Alternatively, in instances whereby the target gene encodes an extracellular protein, it can be preferable to co-administer normal target gene protein in order to maintain the requisite level of target gene activity.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxynucleotides to the 5' and/or 3' ends of the molecule or the use of phosphorothioate or 2' O-methyl rather than phosphodiesterase linkages within the oligodeoxyribonucleotide backbone.

Endogenous gene expression can also be reduced by specifically inactivating or "knocking out" the target and/or pathway gene or its promoter using targeted homologous recombination. (e.g., see Smithies et al., 1985; Thomas et al., 1987; Thompson et al., 1989). For example, a mutant, non-functional gene (or a completely unrelated DNA sequence) flanked by DNA homologous to the endogenous gene (either the coding regions or regulatory regions of the gene) can be used, with or without a selectable marker and/or a negative selectable marker, to transfect cells that express the gene in vivo. Insertion of the DNA construct, via targeted homologous recombination, results in inactivation of the gene. Such approaches are particularly suited in the agricultural field where modifications to ES (embryonic stem) cells can be used to generate animal offspring with an inactive gene (e.g., see Thomas et al., 1987 and Thompson et al., 1989). Such techniques can also be utilized to generate immune disorder animal models. It should be noted that this approach can be adapted for use in humans provided the recombinant DNA constructs are directly administered or targeted to the required site in vivo using appropriate viral vectors, e.g., herpes virus vectors. Targeted homologous recombination also is useful to introduce point mutations into a gene or other small modifications that may alter the activity of a gene product. Other methods of targeting specific changes to a gene make use of, for example small RNA/DNA hybrids (see Cole-Strauss et al, 1996; Ye et al., 1998).

Alternatively, endogenous gene expression can be reduced by targeting deoxyribonucleotide sequences complementary to the regulatory region of the gene (i.e., the gene promoter and/or enhancers) to form triple helical structures that prevent transcription of the gene in target cells in the body. (See generally, Helene, C. 1991; Helene et al., 1992; and Maher, 1992).

6.10.9 Assays for the Biological Activity of Polypeptides

The methods described above to assay a compound for interactions with a gene product or effects on the biological function and/or expression of a gene product can equally be used to assay polypeptides, polypeptide fragments (and analogs) encoded in polynucleotides and homologs identified and characterized according to the parallel methods of the invention. See, Hider et al. (1991), Taylor et al. (1994), Goodman et al. (1995), Osslund (1996). In addition, the polypeptides and analogs can be assayed for biological (or pharmacological) activity in tissue culture or in an organism. See for example Weissmann (1985), Jones et al. (1987), Lin (1987), Souza (1989, 1992), Pierce et al. (1998), Stern, M. E. (1999), Samal (1999), Bachmaier et al. (1999), and Tartaglia (1999).

6.10.10 In vitro Evolution

Another embodiment of this invention involves mutagenizing a sequenced polynucleotide and assaying the encoded polypeptide for altered activity. A polynucleotide that encodes a gene product isolated from a natural source can serve as a template for subsequent modification and "improvement" of the gene product for specific uses. Site-directed mutagenesis is well known in the art and has long been used to modify the activity of a gene product (see for example, Pictet, 1991; Kunkel, 1989; Chappel et al., 1993; Chaleff, 1994; Powers et al., 1998; Gehrke et al., 1994; Yamashita et al., 1994; Harper et al., 1990; Zukowski et al., 1990). Random mutagenesis followed by selection or screening protocols provide powerful methods to alter the activity of a gene product (see for example Davis et al., 1980; Miller, 1972; Rose et al., 1990). More recently, techniques have been developed that couple random mutagenesis and in vitro evolution to sample a greater variety of potentially useful mutations than can reasonably be assayed by the more traditional techniques mentioned above (see Stemmer, 1997; Buchholz et al., 1998; and Zhao et al., 1998).

6.10.11 Pharmaceutical Preparations and Methods of Administration

The nucleic acid sequences, polypeptides and other compounds described above may have therapeutic value and may be administered to a patient at therapeutically effective doses to treat or ameliorate disease. A therapeutically effective dose refers to that amount of a compound sufficient to result in amelioration of the disease symptoms, or alternatively, to that amount of a nucleic acid sequence sufficient to modulate the expression of a gene product which results in the amelioration of the disease symptoms.

6.10.11.1 Effective Dose

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

6.10.11.2 Formulations and Use

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pre-gelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g. almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds also can be formulated in rectal compositions such as suppositories or retention enemas, e.g., containing conventional suppository bases such as cocoa butter or other glycerides.

In addition to the formulations described previously, the compounds also can be formulated as depot preparations. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

6.10.12 Assays for Polymorphisms

Polymorphisms represent differences in DNA sequence between members of the same species. Polymorphisms include for example, single nucleotide polymorphisms (SNPs), variations in Short Tandem Repeats (STRs), Restriction Fragment Length Polymorphisms (RFLPs), insertions, deletions and rearrangements.

Well developed methods exist in the art for assaying polymorphic and phenotypic differences between individuals by genetic mapping to characterize the genetic changes that give rise to phenotypic variation. These methods can be used, for example, to discover mutations responsible for genetic disease, to manipulate and breed useful traits in plants and animals, to discover elements in genetic pathways, to diagnose propensity towards disease, to determine and diagnose drug response, etc. (see for example, Stone et al 1999; Lebo et al., 1998; Giordano et al., 1998; Rothschild et al., 1996; Blumenfeld et al., 1995; Meyer et al., 1997; Kamb, 1997; Skolnick et al., 1997). Many phenotypic traits are multifactorial and methods are well known for using polymorphisms to discover Quantitative Trait Loci (see for example Webb et al., 1999; Helentjaris et al., 1995; Dupuis et al., 1999; Umari et al., 1996; Lander et al., 1986 & 1989). STRs are highly polymorphic genetic elements and their use in genetic mapping is well known in the art, see for example Caskey et al. (1994) and Polymeropoulos (1995). The utility of SNPs for genetic mapping has recently progressed considerably due to improvements in technology, in particular the ability to assay many different SNPs simultaneously by using for example oligonucleotide arrays. For representative examples see Nikiforov et al. (1999); Shuber, A. P. (1996); Jakubowski et al. (1999); Cho et al. (1999); Brookes (1999); Kruglyak (1999); Sapolsky et al. (1999); Xiong et al. (1999); Wang et al. (1998).

Polymorphisms are easily discovered by sequencing DNA from one or more individuals according to the methods described above and comparing the sequences to discover differences in homologous regions. Indeed, the sequencing invention can be used both as a means to discover new polymorphisms and as a method to assay polymorphisms for genetic mapping studies. Clearly any type of polymorphism can be quickly assayed by sequencing the DNA (see e.g. Santamaria et a., 1997).

To minimize the number of sequences needed to assay an individual, DNA may be enriched for polymorphisms prior to the sequencing reaction. For example, Ostrander et al. (1992) describe a method to enrich for STR sequences in a genomic library. For other examples see Kandpal et al. (1994); Karagyozov et al. (1993) and Paetkau (1999).

The physical mapping methods described above provide another means to discover and assay polymorphic differences between individuals in a population. In most cases, differences in the landmarks between individuals represent differences in the nucleotide sequence. There are exceptions, for example differences in methylation patterns between individuals can be assayed by employing bisulfite-induced modifications prior to cloning the DNA whereby cytosine is converted to uracil, but 5-methylcytosine remains unchanged (see e.g., Frommer et al., 1992).

A preferred landmark for assaying polymorphisms is the restriction site. For example, assuming 0.1% of nucleotides are polymorphic between two homologous chromosomes, then for any 6-base restriction site about 1 in 167 sites will be polymorphic (i.e. one site will be cut by the restriction enzyme and one site cannot be cut). If we assume a genome size of $3 \times 10^9$ base pairs, then we can expect about $(3 \times 10^9 / 4^6)/167 = \sim 4400$ polymorphic restriction sites per assayed 6-base restriction enzyme. Of course, once polymorphisms are discovered, they can be assayed in a population by other methods such as those mentioned above.

6.10.13 Assays for Genomic Alterations Within an Individual

Changes can occur in the genome of an individual during the course of development or during the progression of disease. The result is variation between different populations of cells within the individual. This variation can be assayed using the parallel methods of this invention.

Any change at the nucleotide level can be determined simply by sequencing the genomic DNA from different populations of cells using the parallel methods described above. For example, the sequence of DNA from cancerous tissue can be compared to the sequence of DNA from nearby normal tissue. Changes in the genome are known to occur during disease progression, and analysis at the sequence level can help to pinpoint those changes that contribute to the diseased state.

Genomic rearrangements can readily be assayed at a lower resolution by observing differences in the landmarks. In particular, changes in restriction site patterns will occur not only as a result of single base changes, but also due to rearrangements at both a fine and gross level. The physical mapping methods described above typically yield information from a larger contiguous stretch of DNA than the sequencing methods. Thus fewer clones need to be analyzed to quickly "survey" the genomic DNA from, for example, a diseased tissue. Rearrangements discovered in this manner may represent changes that contribute to the diseased state.

6.10.14 Transgenic/Recombinant Organisms

Polynucleotides characterized according to this invention can be expressed in transgenic (or recombinant) multicellular organisms. Animals of any species, including, but not limited to, mice, rats, rabbits, guinea pigs, pigs, micro-pigs, goats, and non-human primates, e.g., baboons, monkeys, and chimpanzees may be used to generate transgenic animals. Other animal species may be used to create transgenic animals such as *Drosophila, C. elegans*, Xenopus, zebra fish, etc. Polynucleotides can also be inserted into the genomes of a variety of plants and microorganisms to create transgenic organisms.

Any technique known in the art may be used to introduce a polynucleotide or its associated gene into organisms to produce the founder lines of transgenic organisms. Such techniques include, but are not limited to pronuclear microinjection (Wagner et al., 1989); retrovirus mediated gene transfer into germ lines (van der Putten et al., 1985); gene targeting in embryonic stem cells (Thompson et al., 1989); electroporation of embryos (Lo, 1983); sperm-mediated gene transfer (Lavitrano et al., 1989; Perry et al., 1999); *Agrobacterium tumefaciens* mediated transformation (An et al., 1988; Chee et al., 1992; Moloney et al., 1993), etc. For a review of animal techniques, see Gordon, (1989). Other examples include Lundquist et al. (1996), Yoder et al. (1993), and Krzyzek et al. (1995).

The present invention provides for transgenic organisms that carry the transgenes in all their cells, as well as organisms which carry the transgene in some, but not all their cells, i.e., mosaics. The transgene may be integrated as a single transgene or in concatamers, e.g., head-to-head tandems or head-to-tail tandems. The transgene also may be selectively introduced into and activated in a particular cell type by following, for example, the teaching of Lasko et al. (1992). The regulatory sequences required for such a cell-type specific activation will depend upon the particular cell type of interest, and will be apparent to those of skill in the art. When it is desired that the transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting or modifying the function of the nucleotide sequence of the endogenous gene. The transgene also may be selectively introduced into a particular cell type, thus inactivating the endogenous gene in only that cell type, by following, for example, the teaching of Gu et al. (1994). The regulatory sequences required for such a cell-type specific inactivation will depend upon the particular cell type of interest, and will be apparent to those of skill in the art.

Methods for the production of single-copy transgenic organisms with chosen sites of integration are also well known to those of skill in the art. See, for example, Bronson et al. (1996) and Bradley et al. (1997).

Once transgenic organisms have been generated, the expression of the recombinant gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals also may be assessed using techniques which include but are not limited to Northern blot analysis of tissue samples obtained from the animal, in situ hybridization analysis, and RT-PCR. Samples of the gene-expressing tissue may also be evaluated immunocytochemically using antibodies specific for the transgene product.

The methods described above for generating cells with insertion elements at known locations are well suited to the generation of transgenic organisms with insertion elements in their genomes. For example, the methods may be practiced on mouse embryonic stem cells from which an adult animal can be cloned. Other animals have been cloned from cell lines derived from embryos, see for example Campbell et al. (1996), Chen et al. (1999), Hong et al. (1998), Baguisi et al. (1999), and Cibelli et al. (1998).

Animals and cell lines with mapped insertion elements and transgenic animals and cell lines made by other methods such as those described above have the potential to model various human diseases (e.g., Robinson et al., 1996). In this context, the animals or cell lines can serve as tools to test pharmaceuticals for efficacy in treating the disease (see for example Cordell, 1995; Weinshilboum et al., 1995; Leder et al., 1992; Hammer, 1996; Groffen et al., 1996; Terhorst et al., 1996; Donehower et al., 1996; Lazzarini, 1997). The transgenic animal model systems may be used as a test substrate to identify drugs, pharmaceuticals, therapies and interventions which may be effective in treating the disease or disorder of interest. Therapeutic agents may be administered systemically or locally. Suitable routes may include oral, rectal, or intestinal administration; parenteral delivery, including intramuscular, subcutaneous, intramedullary injections, as well as intrathecal, direct intraventricular, intravenous, intraperitoneal, intranasal, or intraocular injections, to name just a few. The response of the animals to the treatment may be monitored by assessing the reversal of the disease. With regard to intervention, any treatments which reverse any aspect of the disease should be considered as candidates for therapeutic intervention. Dosages of test agents may be determined by deriving dose-response curves.

The transgenic animal model systems for a disease also may be used as test substrates to identify environmental factors, drugs, pharmaceuticals, and chemicals which may exacerbate the progression of the disease that the transgenic animals exhibit.

In an alternate embodiment, the transgenic animal models for disease may be used to derive a cell line which may be used as a test substrate in culture, to identify both agents that reduce and agents that enhance the disease. While primary cultures derived from the transgenic animals of the invention may be utilized, the generation of continuous cell lines is preferred. For examples of techniques which may be used to derive a continuous cell line from the transgenic animals, see Small et al., 1985.

Insertion elements at known locations can serve as a starting point for subsequent targeted modifications to the genome. For example, the insertion element may carry a marker such as HSV-TK for which a negative selection exists (Capecchi et al., 1996). Targeted modifications to the DNA surrounding the insertion element can be generated in the cell by first modifying in vitro a subclone of the surrounding DNA (absent the insertion element) using traditional recombinant methods, transfecting the modified subclone into for example a cell line that carries the insertion element, and selecting for loss of the HSV-TK marker. The end result is the loss of the insertion element and the introduction of the targeted modification. The insertion element may also carry a cleavage site for a rare-cutting enzyme such as Sce I, in which case cotransfection with a plasmid encoding Sce I endonuclease may lead to double-strand breaks and improved rates of targeted homologous recombination (see e.g. Dujon et al., 1999; and Smih et al., 1995).

6.10.15 Databases

The sequences of polynucleotides determined by the methods described above can be stored in a database to facilitate analysis of the information. Methods for preparing a database of sequence information are well known in the art, see for example Bilofsky et al. (1986), Benson et al. (1994), Doolittle (1990), and Sabatini et al. (1999). Other databases can be created from the sequence information such as for example a database of polymorphisms and a polypeptide database comprising theoretical translations of polynucleotide sequences, see e.g. Claverie et al. (1985) and Stulich et al. (1989).

6.11 Kits for Implementing the Method of the Invention

The invention includes kits for carrying out the various embodiments of the invention. Preferably, kits of the invention include a set of primers and/or adapters for carrying out the reactions and amplifications in accordance with the invention. Kits also may include an array of tag complements attached to a solid phase support. Additionally, kits of the invention may include sample tags or sample-tagged vectors. Kits also may contain appropriate buffers for enzymatic processing, detection chemistries, e.g. fluorescent components for labeling amplicons, instructions for use, processing enzymes, such as ligases, polymerases, and so on. These and other aspects of the invention are illustrated by the following non-limiting examples.

7. EXAMPLES 7.1 Example 1

In this example, sequence information was obtained for a subset of cloned inserts from a pool of about 110 different cloned inserts. Sample-tagged vectors with inserts were constructed in *E. coli* using standard techniques. Sample tags were created by ligating complementary pairs of oligonucleotides into the unique Pvu II site of the commercial vector pSP72 (Promega). Eleven different tags are shown below:

```
Tag1
CAGCACCAGGAAGGTGGCCAGGTTGGCAGTGTA         (SEQ ID NO:1)

Tag2
CCTAGCTCTCTTGAAGTCATCGGCCAGGGTGGA         (SEQ ID NO:2)

Tag3
ATCAAGCTTATGGATCCCGTCGACCT                (SEQ ID NO:3)

Tag4
GGTGCTCGTGTCTTTATCGTCCCTACGTCTCTT         (SEQ ID NO:4)

Tag5
AATTTTGAAGTTAGCTTTGATTCCATTC              (SEQ ID NO:5)

Tag6
GGCGTCCTGCTGCAGTCTGGCATTGGGAA             (SEQ ID NO:6)

Tag7
ATTGAAGATGGAGGCGTTCAACTAGCA               (SEQ ID NO:7)

Tag8
GATGAACTATACAAGCTTATGTCCAGACTTCCA         (SEQ ID NO:8)

Tag9
AAGGGCAGATTGGTAGGACAGGTAATG               (SEQ ID NO:9)

Tag10
CCGTCGGGCATCCGCGCCTTGAG                   (SEQ ID NO:10)

Tag11
TACATTGTGTGAGTTGAAGTTGTATTCCAATTT         (SEQ ID NO:11)
```

Inserts were cloned between the BglII and XbaI sites of pSP72. These inserts were derived from a complete restriction digest of rat genomic DNA with BamH I, BglII and XbaI. The relevant sequence of a Tag11 construct is shown below:

```
                                         (SEQ ID NO:12) . . .
        1         10        20        30
. . .ATTTAGGTCACACTATAGAACTCGACCAGTACATTGTGTGAGT
              SP72for>>

40        50        60        70        80
TGAAGTTGTATTCCAATTTCTGAAGCTTGCATGCCTGCAGGTCGACT
                                 <<SP72rev
       90
CTAGA
                                         (SEQ ID NO:13) . . .
INSERT . . . GATCTGCCGGTCT
```

The tag is shown in bold lettering. Underlined sequences represent oligonucleotides (SP72for and SP72rev) described below.

For constructs containing Tag1 through Tag10, a single random insert was cloned and grown to saturation in liquid media. For constructs containing Tag11, about 100 random inserts were cloned, pooled and grown to saturation in liquid media. A pool of about 110 random inserts was made by diluting each single isolate (i.e., constructs containing Tag1 through Tag10) into the pool of Tag11 constructs at a ratio of 1:100. In this pool, with the exception of Tag11, each tag is associated with a single, unique insert. This pool of about 110 constructs was grown further, and plasmid DNA was prepared using a Qiagen midiprep kit.

The plasmid DNA (3 µg) was sequenced using a Sequenase kit (Amersham Pharmacia Biotech) and primer SP72for (GGTGACACTATAGAACTCGAGCAG, SEQ ID NO:14). Note this primer sequences through the tag and into the insert. $^{35}$S-dATP was incorporated during the sequencing reaction. The labeled products were separated in four lanes of a standard 6% polyacrylamide urea sequencing gel in 1×TBE (89 mM Tris borate, pH 8.3/2 mM EDTA). The gel was dried onto Whatman 3MM paper.

Figure 7A:
FIG. 7a is a photograph of an autoradiogram of multiplexed sequencing reactions separated on a denaturing polyacrylamide gel.

The sequencing ladder was visualized by exposing the gel to film. The sequence of base 29 through base 90 was clearly visible (see FIG. 7a). This result is expected since constructs containing Tag11 made up over 90% of the pool. After base 90, a uniform evenly-spaced ladder of over 100 bands was evident in all four lanes. This multiplex ladder represents the superposition of the sequencing ladders from all the clones in the pool.

Figure 7B:
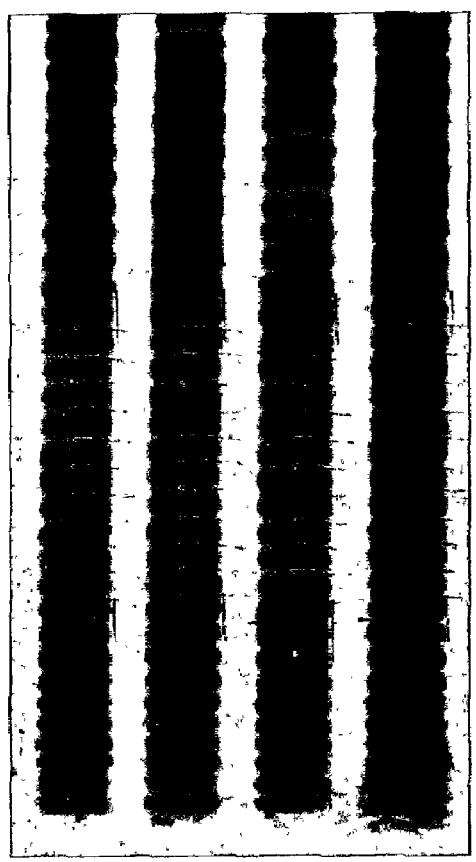
FIG. 7b is a photograph of an autoradiogram that served as a template for fractionating multiplexed sequencing reactions.

The film was aligned with the dried gel. Using the multiplex ladder as a marker, 10 adjacent sections were excised from each lane with a razor blade so that adjacent edges were touching. Each section contained only one marker band, which was situated in the middle of the section (see FIG. 7b). The first four sections (one from each lane, taken from the bottom of the sectioned region of the gel) contained bands at the eleventh position of the multiplex ladder, which corresponds to "base" 101 in the Tag11 construct shown above. The 40 sections (or fractions) were separately placed into 100 µl H$_2$O and heated to 70° C. for 20 minutes. One microliter of the eluted DNA was amplified in a 20 µl polymerase chain reaction with Taq polymerase and PCR buffer according to the manufacturer's instructions (Promega). Briefly, the primers SP72for (SEQ ID NO:14) and SP72rev, CAGGCATGCAAGCTTCAG (SEQ ID NO:15) were used at 0.8 µM with 0.2 mM dNTPs, 1.5 mM MgCl2, PCR buffer and polymerase. The PCR mixture was subjected to the following cycle parameters: 94° C., 30 s; 55° C., 30 s; 72° C., 30 s; 35 cycles The PCR mixtures were treated with phosphatase to remove residual unincorporated nucleotides. In a 10 µl reaction the following were combined: 3 µl PCR mixture, 7 µl Shrimp Alkaline Phosphatase (United States Biochemical, diluted to 0.14 units/µl). The reactions were incubated at 37° C. for 15 minutes and terminated at 80° C. for 15 minutes. 2 µl solution of fresh primers (SP72for and SP72rev each at 2.4 µM) was added to each reaction. The resulting mixtures were heated to 100° C. for 2 minutes and immediately placed on ice in preparation for labeling with $^{32}$P-dATP.

The labeling step was accomplished with Sequenase, Reaction Buffer and Labeling Mix supplied by the manufacturer (Amersham Pharmacia Biotech). Briefly, 3 µl phosphatase-treated PCR mix was combined with 0.60 µl Reaction Buffer, 0.30 µl 0.1M dithiothreitol, 0.12 µl Labeling Mix, 0.15 µl $^{32}$P-dATP (3000 Ci/mmol) and 1.1 µl Sequenase (diluted to 0.85 units/µl). Reactions were incubated for 10 minutes at room temperature. 4 µl 0.2 mM dNTPs (in 10 mM Tris-HCl, 10 mM MgCl2, 50 mM NaCl pH 7.9) was added to each reaction followed by another 10 minute incubation at room temperature. Reactions were terminated by the addition of 2 µl 100 mM EDTA.

Identification of the specific tags in each labeled PCR product was achieved by dot-blot hybridization. The oligonucleotides originally used to create the tagged constructs were employed again to make the dot-blots. However, small oligonucleotides will not hybridize well once bound to nylon membranes. It was necessary to "lengthen" the oligonucleotides before application to the membrane. Using standard techniques, each pair of complementary oligonucleotides described above was ligated to Hinc II digested pBR322. The resulting ligation mixture was PCR amplified with two primers: one oligonucleotide from the complementary pair and a second common oligonucleotide, CACTATCGAC-TACGCGATCA (SEQ ID NO:16). The sequence of the common oligonucleotide begins 320 bases upstream of the Hinc II site at position 653 in pBR322. The resulting PCR product is simply a fusion of the oligonucleotide tag to a 320 base fragment derived from pBR322. The dot-blots were made with a 96-well Blotting Apparatus and Zeta-Probe membrane according to the manufacturer's instructions (BioRad). About 5 to 10 ng of a "lengthened" oligonucleotide tag was applied per spot.

Each labeled PCR product from above was hybridized to a membrane with 10 different spots. Each spot hybridizes to a different tag (Tag1 through Tag10). The labeled PCR products were used directly without further purification. Hybridizations were performed in 2 ml hybridization solution (0.5 M Na2HPO4 pH 7.2, 7% SDS according to Zeta-Probe instructions) at 55° C. for 20 hours in plastic bags. Four 30-minute washes were performed at 40° C.

Figure 8:
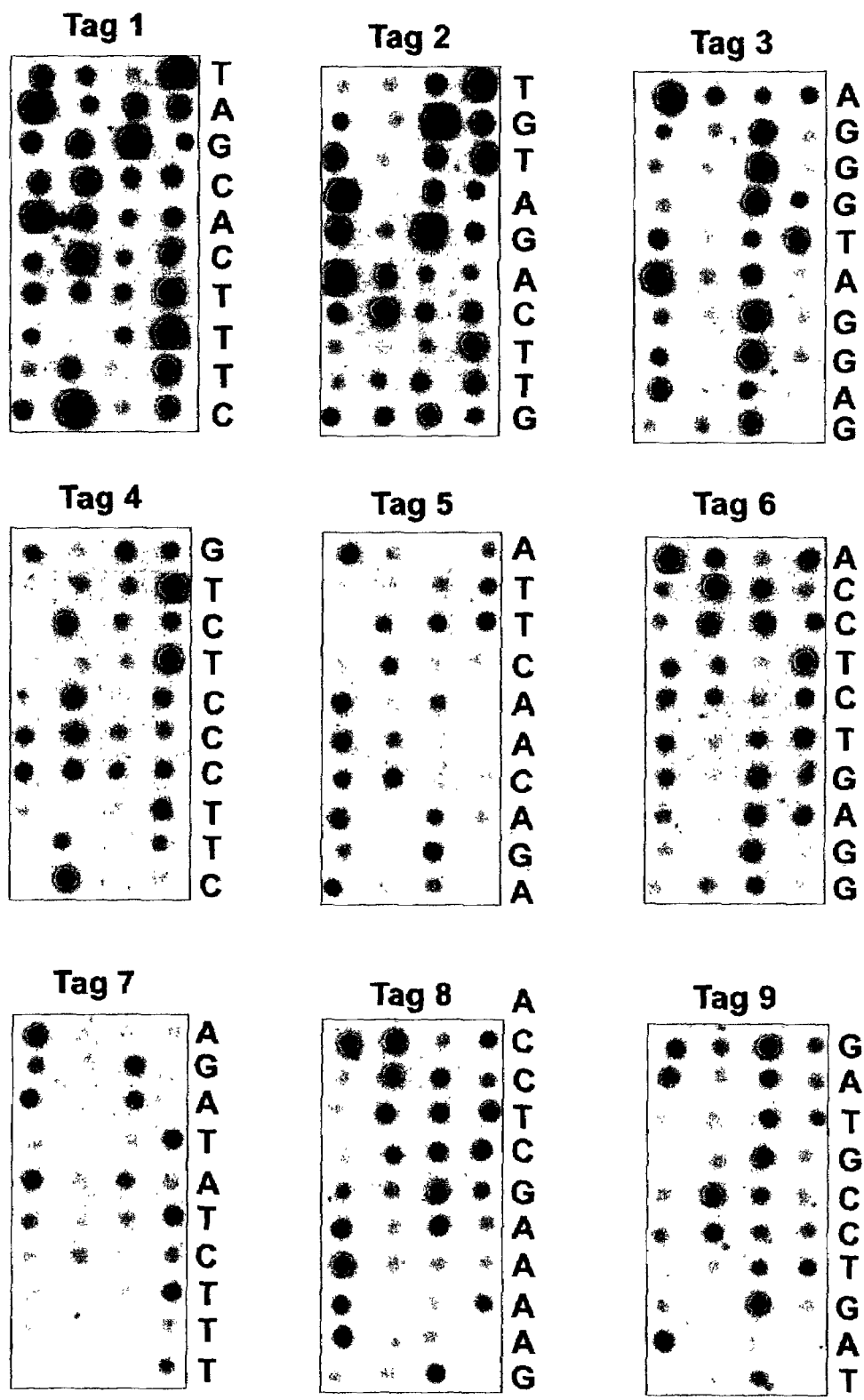
FIG. 8 are the readout from a multiplex sequencing experiment.

Autoradiography was performed on the hybridized dot-blots. The results are shown in FIG. 8. Each construct containing Tag1 through Tag9 was sequenced separately by standard means. The expected sequence for constructs containing Tags 1 through 9 is shown adjacent to the autoradiograms. The hybridization signal strength depends on the tag sequence. This variability can be minimized by optimization of the tag sequence and hybridization conditions. Clearly, when the signal strength is high, the hybridization pattern corresponds faithfully to the expected sequence. As the hybridization signal approaches background levels, some bases become ambiguous. Tag10 failed to produce a hybridization signal. The absence of signal was likely due to differences between the actual Tm of this tag as compared to Tag1 through Tag9. Note the readout from the array of 10 tag complements has been rearranged in FIG. 8 to more clearly show the sequence of the inserts. The actual readout was strips of 10 spots corresponding to the ten different tags.

6.2 Example 2

This example describes a strategy for simultaneously sequencing about 37,000 different templates. A collection of about 100,000 sequence-tagged vectors is constructed from the commercially available bacteriophage vector M13 mp18. Using standard methods, the vector M13PL1 is constructed by modifying M13 mp18 between the EcoR I and Hind III sites as shown:

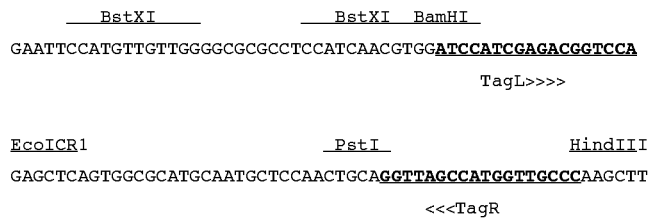

(SEQ ID NO:17)

A pool of 100,000 different oligonucleotides is synthesized 3'->5' on an ABI model 394 DNA synthesizer by the "split and pool" approach described by Brenner (1997b). The sequence "TGCA" is synthesized on 10 columns. A different 5 base sequence is added to each of the 10 columns. The column packing material is removed from each column, mixed together and repacked into the 10 columns. A different 5 base sequence is synthesized on each column. The split, synthesize and pool process is repeated three more times. The different sequences synthesized at each step are shown in Table 1 (sequences are shown 5'→3').

TABLE 1

| column | step 5 | step 4 | step 3 | step 2 | step 1 |
|--------|--------|--------|--------|--------|--------|
| 1 | CTACT | CAGTC | TGTAG | TGACA | GAGCA |
| 2 | GAACT | GTGTC | ACTAG | AGACT | CTGCA |
| 3 | GTTCT | GACTC | AGAAG | TCACT | CACCA |
| 4 | GTAGT | GAGAC | AGTTG | TGTCT | CAGGA |
| 5 | GTACA | GAGTG | AGTAC | TGAGT | CAGCT |
| 6 | GATGA | GTCAG | ACATC | TCTGA | CTCGT |
| 7 | CTTGA | CACAG | TGATC | AGTGA | GACGT |
| 8 | CAAGA | CTGAG | TCTTC | ACAGA | GTGGT |
| 9 | CATCA | CTCTG | TCAAC | ACTGT | GTCCT |
| 10 | CATGT | CTCAC | TCATG | ACTCA | GTCGA |

The oligonucleotides are removed from the column, deprotected and concentrated. M13PL1 is cut with Pst I and EcoICR I. 100 fold molar excess of the oligonucleotides is ligated to the cut vector. Excess oligonucleotides are removed using a Qiaquick kit (Qiagen). The vector/oligonucleotide is "filled in" with Klenow fragment (3'→5' exo-, New England Biolabs), the reaction products are circularized with ligase, and transformed into highly competent XL1-Blue (Stratagene). About 10 million transfectants are combined to make the sample-tagged vector pool. Double-stranded (RF1) DNA is prepared from the pool with the Qiagen Plasmid Purification System (Qiagen).

A mouse genomic library is prepared in the pool of sample-tagged phage vectors. Mouse DNA from strain 129/Sv is sheared to a fragment size of 3-6 kb using the Hydoshear (Genomic Instrumentation Services; San Carlos, Calif.; see Oefner et al., 1998), according to the manufacturer's instructions. The sheared DNA is ligated to an adapter made by annealing the following two phosphorylated oligonucleotides:

```
    TGAGTCACCAAC        SEQ ID NO:18
    GTGACTCA
```

The ligation products are separated on a 1% agarose gel in 1×TAE and 2-3 kb fragments are cut from the gel. The fragments are purified with a Qiaquick Column (Qiagen) according to the manufacturer's instructions.

The fragments are ligated into the pool of sample-tagged vectors prepared above. The resulting library is electroporated into the strain XL1-Blue (Stratagene) and spread onto LB agar plates. About 100,000 transfectants are pooled by eluting the phage from the agar plates into a solution of LB. The phage titer is increased by subsequent growth in liquid LB. 0.1 ml overnight culture of XL1-Blue is combined with phage at a multiplicity of infection around 10, diluted into 10 ml LB and grown at 37° C. to saturation. Phage are separated from the cells by centrifugation and the single-stranded phage DNA is purified with the Qiaprep M13 System (Qiagen) according to the manufacturer's instructions.

Ten sequencing standard templates are prepared by cloning a random fragment of the mouse DNA into each of 10 vectors. Each vector is identical to the sample-tagged vectors described above except the 25 base distinct region is replaced with the following sequences:

| | |
|---|---|
| TCAATCGACTACACTCGTAACAAGA | SEQ ID NO:19 |
| GATCAATTCGCTAATCGATCGTATA | SEQ ID NO:20 |
| AAATAGATCGCATAAGCAGTACGTG | SEQ ID NO:21 |
| TCATAGGCTGACAGTCCTAGCTAGT | SEQ ID NO:22 |
| TCGTAGACAGTACATGTCGATGAAT | SEQ ID NO:23 |
| TAACCGATCTAGTCGATCTACGACT | SEQ ID NO:24 |
| GTTTCGAGCTAGCTAAGAGACTCGT | SEQ ID NO:25 |
| CGTATTTCGACTGACTAGCCTCTAG | SEQ ID NO:26 |
| AGTTCGATCAGCTAACTCTGAGTCA | SEQ ID NO:27 |
| GCTATATCGATCGTCCATTAACGTA | SEQ ID NO:28 |

Each fragment is separately sequenced with the primer TagR, GGGCAACCATGGCTAACC, (SEQ ID NO:29) by standard means. The ten standard phage are grown separately in liquid as above and equal numbers of phage are pooled. Single-stranded DNA is prepared from the pooled standards as above.

The pool of sample-tagged phage DNA (3 μg) is combined with the pool of standard phage DNA (0.3 ng). The combined pool is sequenced using a Sequenase kit (Amersham Pharmacia Biotech) and the primer TagR. Unlabeled dATP is substituted for $^{32}$P-dATP in the manufacturer's protocol since these sequencing ladders will not be directly visualized after electrophoresis. The result is four collections of tagged termination products corresponding to terminal A, C, G, and T.

A size standard is made by sequencing a separate aliquot of the phage DNA with a second primer M13gI, CTGAATCTTACCAACGCTAAC, (SEQ ID NO:30). This primer anneals to a sequence element in gene I far from the sample inserts, so it will produce an identical sequencing ladder for all the phage in the pool. This time $^{32}$P-dATP is incorporated in the sequencing reaction products. The four separate termination reactions are pooled in a 1:1:1:2 ratio (A:T:C:G). The excess "G" reaction simplifies alignment of different lanes after electrophoresis. 1 μl of this labeled size standard is added to 3 μl of each collection of tagged termination products.

The four collections are electrophoresed at 40 V/cm in a standard 7M urea, 0.5×TBE, 0.4 mm thick sequencing gel with 0.5 cm lanes. The gel is dried onto Whatman 3MM paper. The size standard is visualized by autoradiography. The film is aligned with the dried gel and individual bands are excised as described in Example 1. The tagged reaction products in each gel slice (fraction) are electroeluted into a volume of 50 μl with the Electroelutor (Amika Corp, Columbia, Md. and see Shukla, 1994).

The tagged reactions in each fraction are PCR amplified with two oligonucleotides: TagL, ATCCATCGAGACGGTCCA (SEQ ID NO:31) and TagR+biotin. TagR+biotin is identical in sequence to TagR and it is conjugated to biotin at the 5' end during oligonucleotide synthesis using the LC Biotin-ON Phosphoramidite (Clontech). 5 μl from each fraction is amplified in a 100 μl reaction with Taq polymerase (Promega) and PCR buffer according to the manufacturer's directions. Briefly, the primers are used at 1 µM with 0.2 mM dNTPs, 1.5 mM MgCl2, PCR buffer and polymerase. The cycling parameters are as follows: 94° C., 30 s; 55° C., 30 s; 72° C., 30 s; 40 cycles. Prior to hybridization to the arrays, the PCR samples are denatured at 96° C. for 5 min and cooled on ice for 5 min.

Arrays of the 100,000 oligonucleotides (single-stranded) are synthesized with parallel light-directed chemistry (Affymetrix, Santa Clara, Calif. has a custom array service). For details see Fodor et al. (1991 & 1995); Pease et al. (1994). Current technology allows fabrication of about 320,000 distinct oligonucleotides on a 1.28 cm×1.28 cm array; each oligonucleotide is present at about $10^7$ copies in a 20 µm×25 µm "spot" (Wang et al., 1998). The oligonucleotides are identical in sequence to the combinations allowed in Table I (read 5' to 3'). An additional 10 oligonucleotides are synthesized that correspond in sequence to the 10 standard sample tags.

The arrays are hybridized with 6×SSPET (0.9M NaCl, 60 mM NaH2PO4 pH 7.4, 6 mM EDTA, 0.005% Triton X-100) for 5 minutes. 100 µl of 2×hybridization buffer (2×=6M tetramethylammonium chloride, 20 mM Tris-HCl pH 7.8, 2 mM EDTA, 0.02% TritonX-100 with 200 µg/ml sonicated herring sperm DNA (Promega)) is added to each denatured PCR sample from above for a final volume of 200 µl. Each sample (fraction) is hybridized to one array for 15 hours at 44° C. in a hybridization chamber (Affymetrix) on a rotisserie at 40 rpm. The arrays are washed three times with 1×SSPET and 10 times with 6×SSPET at 22° C. The hybridized biotinylated amplicons are then stained at room temperature with staining solution (streptavidin R-phycoerythrin (2 µg/ml, from Molecular Probes) and acetylated bovine serum albumin (0.5 mg/ml) in 6×SSPET) for 8 minutes, followed by 10 washes with 6×SSPET at 22° C. on a fluidics workstation (Affymetrix). The arrays are visualized with a confocal chip scanner (Hewlett-Packard/Affymetrix) with a 560 nm filter.

The digitized signals from each array are compared and any array to array hybridization variability is corrected by reference to the 10 known standard sequences. Sequence ladders are reconstructed from the hybridization patterns.

7.3 Example 3

This example describes a method for simultaneously generating about 37,000 restriction maps.

A pool of about 100,000 sample-tagged fosmid vectors is prepared by PCR amplifying the sample tags from the pool of phage vectors in Example 2 and cloning the collection into the fosmid vector pFOS1 (Kim, U. J. et al, Nucl. Acids Res. 20:1083-85 (1992)). DNA from the phage pool is amplified with two primers, TagR and CAACGTGGATC-CATCGAGA (SEQ ID NO:32), in a PCR reaction using Pfu polymerase (Stratagene) according to the manufacturer's instructions. The resulting amplicons comprise TagR, the variable sequences and TagL plus the BamH I site shown above. The amplicons are cut with BamH I and pFOS1 is cut with BamH I and Srf I. The vector and sample tags are joined by ligation and transformed into the bacterial strain pop2136 (Kim et al., 1992) by electroporation. Note both restriction sites are restored in the vector after ligation to the sample tags. About 10 million transformants are pooled and plasmid DNA is prepared with the Qiagen Plasmid Purification System (Qiagen). The plasmid DNA is prepared for cloning genomic DNA as described by Kim, et al. (1992). The plasmid pool is linearized with Aat II, dephosphorylated with Alkaline Phosphatase and then digested with BamH I.

Similarly, the ten standard sample tags described in Example 2 are separately cloned into pFOS1 and plasmid DNA is prepared for cloning as above.

A library is constructed in the pool of sample-tagged fosmid vectors. High molecular weight mouse DNA is partially digested with Mbo I to an average size of 40 kb, treated with alkaline phosphatase, and ligated to the vector DNA prepared above as described by Kim, et al. (1992). The ligation mixture is packaged into lambda phage heads using the Gigapack III XL packaging extract (Stratagene). The packaged clones are transfected into strain DH5α-MCR (Gibco BRL). About 100,000 clones are pooled and grown as a liquid culture in LB media. Plasmid DNA is purified from the pool with the Qiagen Large Construct Kit (Qiagen) according to the manufacturers instructions. Similarly, a random genomic fragment is cloned into each standard sample-tagged vector, the 10 standards are grown, plasmid DNA is purified as above and equal amounts of each standard are combined to make a standard pool.

The pool of sample-tagged DNA is combined with the pool of standards (10,000:1 mass ratio). The pooled DNA is linearized with Srf I and divided into four aliquots. A different double-stranded adapter is ligated to DNA in each aliquot. Excess adapters and salts are removed from the ligation reactions by electrodialysis with the electroelutor (Amika Corp., Columbia, Md.). The adapter sequences are shown below:

```
5'-GCTCATTGCGGTAGCATACC       Adap1     SEQ ID NO:33
                CATCGTATGG-5'           SEQ ID NO:34
5'-GCGTGGCCTACTACGATTGT       Adap2     SEQ ID NO:35
                  GATGCTAACT-5'         SEQ ID NO:36
5'-GACGTAGCGAACTAGGGCAG       Adap3     SEQ ID NO:37
                    TGATCCCGTC-5'       SEQ ID NO:38
5'-GCAAGCAGCCTACGCATTAT       Adap4     SEQ ID NO:39
                     ATGCGTAATA-5'      SEQ ID NO:40
```

Each aliquot is subjected to partial restriction analysis with a different enzyme (EcoR I, XbaI, Nsi I or BglIII). The partial digestion reaction conditions are first calibrated as follows. One of the ten standard clones is digested with Not I and end-labeled with $^{32}$P-dGTP by standard means (see Ausubel et al., 1997). The labeled standard is digested with different concentrations of each enzyme. 10 µg of the sample-tagged/standard DNA pool is linearized with Srf I, combined with about 10 ng of the end-labeled standard and incubated with the different enzyme concentrations at 37° C. for 15 minutes. The products are analyzed by agarose gel electrophoresis and visualized by autoradiography. The enzyme concentration is chosen that produces the most uniform distribution of fragments from the labeled standard. Now the appropriate enzyme concentration is used to partially digest the four pools of sample-tagged clones with adapters.

The four partial digests are pooled and run in a single lane of a 32 cm, 0.8% agarose gel. The separated products are collected during electrophoresis onto anion exchange paper (NA-45, Schleicher & Schuell) using the GATC 1500 Direct Blotting Electrophoresis System (GATC GmbH; Konstanz, Germany) as described (Beck, 1993). The paper is pulled along the bottom edge of the gel during electrophoresis at a constant speed of 10 cm/hr, and the voltage is adjusted so the largest fragments elute from the bottom of the gel after 6 hours. The 10 standard clones are analyzed separately to determine their partial digest patterns with the four enzymes.

After electrophoresis, the blotting paper is sectioned at 2 mm intervals. Each section contains the DNA fragments that eluted from the bottom of the gel during a fixed time interval (1.2 min). Each section is washed in TE buffer (10 mM Tris pH 8.0, 1 mM EDTA), transferred to 50 ml elution buffer (2.5 M NaCl, 0.05 M arginine) and heated to 70° C. for 1 hour. The eluted DNA is dialyzed against water with a Spectra/Por Microdialyzer (Fisher Scientific).

Each sample (fraction) is PCR amplified in a 100 µl reaction with a mixture of five primers: TagL, JOE-Adap1, 5-FAM-Adap2, TAMRA-Adap3 and ROX-Adap4, where JOE, 5-FAM, TAMRA and ROX (PE Biosystems) are fluorescent labels attached to the 5' ends of Adap1, etc. Amplification parameters are the same as Example 2.

Each labeled amplicon is separately hybridized to the array of oligonucleotides described in Example 2. Array preparation and hybridization conditions are identical to those described above. The arrays are scanned with the ChipReader (Virtek) and signals from the four different fluorophores are digitized and analyzed. Variabilty in array to array hybridization signals are corrected by reference to the standards. The order and size of the tagged fragments (i e. the restriction maps) are reconstructed from the hybridization patterns with reference to the standards.

7.4 Example 4

This example describes a method for simultaneously positioning about 17,600 insertion elements. The insertion elements are essentially randomly inserted into the genome of *Escherichia coli* with the use of a transposon vector.

pNK2859 is a plasmid that carries a mini-Tn10 and a mutant transposase between two EcoR I restriction sites. The mini-Tn10 consists of two 70 bp inverted repeats flanking a BamH I fragment that carries the $kan^R$ gene (kanamycin resistance) from Tn903 (Kleckner et al., 1991). The mutant transposase eliminates the insertion site bias of the native protein.

The plasmid pIS1 is made by inserting the following sequence at the BamH I site upstream of the $kan^R$ gene in pNK2859:

```
Inverted repeat . . . GGATCCGCGGCCGCACGTGA
                            Not I
CTAGCATGGCCCGGGCGATCC(SEQ   ID    NO:41) . . .
kanR . . .
          Srf I
``` pIS1 is cut with EcoR I. The fragment comprising the mini-Tn10 and transposase is ligated into the single EcoR I site in the lambda "suicide" vector $P_{am}80\lambda$ (Kleckner et al., 1991) to make $P_{am}80\lambda IS1$.

A pool of about 100,000 sample-tagged insertion element vectors is constructed by PCR amplifying the sample tags from the pool of phage vectors in Example 2 and cloning the collection between the Not I and Srf I sites in pIS1. DNA from the phage pool is amplified with two primers (TagR and GTCAGCGGCCGCATCCATCGAGACGGTCCA SEQ ID NO:42) in a PCR reaction using Pfu polymerase (Stratagene) according to the manufacturer's instructions. The resulting amplicons comprise TagR, the variable sequences and TagL plus a Not I site. The amplicons are cut with Not I and $P_{am}80\lambda IS1$ is cut with Not I and Srf I. The sample tags and vector are ligated together and packaged in vitro with the Gigapack III Gold Packaging Extract (Stratagene). The packaged vectors are plated on *E. coli* strain C600. About 10 million phage are pooled and amplified on C600. The sample tagged mini-Tn10 elements are inserted into the chromosome of strain MG1655 (Blattner et al., 1997) according to the method described by Kleckner et al. (1991). Briefly, cells are infected with an equal number of phage, washed, grown for 1 hour in LB and plated on LB plates plus 2.5 mM sodium pyrophosphate and 30µg/ml kanamycin. The plates are incubated overnight at 37° C. Each colony usually contains a sample-tagged mini-Tn10 inserted into the chromosome at a single, essentially random site.

21,952 individual colonies are picked into separate wells of 28 grid plates. Each grid plate contains 784 wells in a 28×28 square grid pattern, and each well holds about 50 µl of liquid culture. The colonies are pooled in a simple 3-dimensional pattern. A 784-pin tool is used to transfer a few microliters from each well in a plate. The first 28 pools (i.e. the z-dimension) are made by pooling cells from all the wells in a single plate. The x and y dimensions are made by using a pad cut with 28 "troughs". Each trough runs the length of a grid plate and is filled with LB. When the 784-pin tool is placed on the pad, 28 pins reside in each trough. Using the 784-pin tool, a few microliters from each well of the 28 plates are transferred to the 28 troughs, representing the x dimension (i.e. the columns). A second trough pad is oriented so the troughs are perpendicular to the first pad's orientation. Without changing the orientation of the plates, all the wells are transferred a second time to make the y-dimension (i.e. the rows). The result is 28+28+28=84 pools and each well is present in only 3 pools.

DNA is prepared from overnight cultures of each pool. The sample tags are amplified from each pool by PCR with primers TagL and TagR, and hybridized to arrays of 100,000 tag complements as described in Example 2. The address of the cells containing each sample-tagged insertion element is determined from the hybridization patterns. About 80% (17,600) of the clones will contain sample tags with unique addresses, that is the sample tags are present in only one cell clone.

To determine the chromosomal locations of the insertion elements, the sample-tagged junctions first are rescued from the chromosomal DNA. A single pool is made from the 21,952 separate bacterial clones. DNA is isolated from an overnight culture and the junctions are rescued by "Panhandle PCR" as described in detail by Jones (1995). Five primers are used in the method as shown below:

| | | |
|---|---|---|
| AATTGGAATCAATAAAGCCCTGCG | Adprimer | SEQ ID NO:43 |
| ACGACTGTGCTGGTCATTAAAC | Primer1 | SEQ ID NO:44 |
| TGATGAATGTTCCGTTGCG | Primer2 | SEQ ID NO:45 |
| CGTATTCAGGCTGACCCTG | Primer3 | SEQ ID NO:46 |
| CGCTGCCCGGATTACA | Primer4 | SEQ ID NO:47 |

The 5 primers hybridize to the mini-Tn10 at sequences upstream of the sample tags and inverted repeat. The DNA from the single pool is cut to completion with Tsp509 I and then treated with alkaline phosphatase. Adprimer is phosphorylated in vitro with T4 kinase and then ligated to the cut pool DNA. The ligation mixture is denatured and then extended with Taq polymerase under conditions which allow the ligated Adprimer to "loop back" and prime DNA synthesis into the mini-Tn10 element. The resulting products are subjected to "nested PCR", first with Primer1 and Primer2 and the second amplification is with Primer3 and Primer4. The end result is a pool of sample-tagged junctions with sequence elements in the following order: Primer4, sample tag, inverted repeat, junction, Adprimer and cPrimer3, where cPrimer3 is the complement of Primer3.

Excess primers and salts are removed from the pool of sample-tagged junctions by electrodialysis with the electroelutor (Amika Corp., Columbia, Md.).

A set of ten sequencing standards is made by PCR amplifying the pool of standards described in Example 2 with two primers, M13uni (TGTAAAACGACGGCCAGTG SEQ ID NO:48) and M13 rev (CAGGAAACAGCTATGACCATGA SEQ ID NO:49). The pool of standards is combined with the pool of sample-tagged junctions (1:2200 mass ratio).

The pooled PCR products are sequenced with TagR using the T7 Sequenase PCR Product Sequencing Kit (Amersham Pharmacia Biotech) according to the manufacturer's instructions with the exception that unlabeled dATP is substituted for $^{32}$P-dATP. The reaction products are processed in parallel and the sequences of the sample-tagged junctions are determined as described in Example 2. Now the sequence of each sample-tagged junction is known therefore the location of the insertion element is known by comparison to the complete sequence of *E. coli* (Blattner et al., 1997). About 12 bases of sequence are required to uniquely identify the location of an insertion element in *E. coli*. Greater than 95% of the insertion elements will be situated 12 base pairs or more from a Tsp509 I site, so about 16,700 of the rescued sample-tagged junctions will contain enough genomic sequence to pinpoint their locations. The cells containing any sample-tagged insertion element can be easily recovered by reference to the well address of the sample tag.

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and the accompanying Figures and Drawings. Such modifications are intended to fall within the scope of the appended claims.

8. REFERENCES

The following documents are hereby incorporated by reference in their entirety.

Adams, C. P. et al., U.S. Pat. No. 5,641,658 (1997)
Adams, M. D. et al., Science, 252:1651-6 (1991)
Agrawal, S., et al., PCT Pat. Pub. No. WO 92/08728 (1992)
Albrecht, G. et al., PCT Pat. Pub. No. WO 97/46704 (1997)
Albretsen, C. et al., Anal. Biochem., 189: 40-50 (1990)
Allison, D. B. et al., U.S. Pat. No. 5,748,491 (1998)
Altschul, S. F. et al., J. Mol. Biol. 215:403-10 (1990)
An, G. et al., in Plant Molecular Biology Manual A3, Kluwer Academic, Dordrecht, pp. 1-19 (1988)
Andersen, P., U.S. Pat. No. 5,840,169 (1998)
Arnold, C. et al., PCR Methods Appl., 1:39-42 (1991)
Ashby, M. et al., U.S. Pat. No. 5,569,588 (1996)
Ausubel, F. M. et al., Current Protocols in Molecular Biology, John Wiley, New York (1997)
Au-Young, J. et al., U.S. Pat. No. 5,734,038 (1998)
Axelrod, V. D. et al., Nucleic Acids Res., 5:3549-63 (1978)
Azpiroz-Leehan, R. et al., Trends Genet., 13:152-6 (1997)
Bachmaier, K. et al., U.S. Pat. No. 5,962,636 (1999)
Baguisi, A. et al., Nat. Biotechnol. 17:456-61 (1999)
Barany, G. et al., U.S. Pat. No. 5,235,028 (1993)
Barillot, E. et al., Nucleic Acids Research, 19: 6241-7 (1991)
Barnes, W. M., Proc. Natl. Acad. Sci. USA, 91:2216-20 (1994)
Beattie, et al., Clinical Chemistry, 39: 719-22 (1993)
Beck, S., Methods Mol. Biol., 23:219-23 (1993)
Beaucage, et al., Tetrahedron, 48: 2223-311 (1992)
Benson, D. A. et al., Nucleic Acids Res., 22:3441-4 (1994)
Bernoist, C. et al., Nature, 290:304-10 (1981)
Bilofsky, H. S. et al., Nucleic Acids Res., 14:1-4 (1986)
Birren, B. W. et al., Genomics, 34:97-106 (1996)
Bitter, G. A. et al., Methods Enzymol., 153:516-44 (1987)
Blattner, F. R. et al., Science, 277:1453-74 (1997)
Bloch, W., U.S. Pat. No. 5,856,192 (1999)
Blumenfeld, A. et al., U.S. Pat. No. 5,387,506 (1995)
Bradley, A. et al., U.S. Pat. No. 5,614,396 (1997)
Brenner, S., U.S. Pat. No. 5,604,097 (1997a)
Brenner, S., U.S. Pat. No. 5,635,400 (1997b)
Brenner, S., U.S. Pat. No. 5,695,934 (1997c)
Brenner, S. et al, U.S. Pat. No. 5,714,330 (1998a)
Brenner, S., U.S. Pat. No. 5,763,175 (1998a)
Brenner, S., U.S. Pat. No. 5,780,231 (1998b)
Brenner, S. et al, U.S. Pat. No. 5,846,719 (1998b)
Brinster, R. L. et al., Nature, 296:39-42 (1982)
Bronson, S. K. et al., Proc. Natl. Acad. Sci. USA 93:9067-72 (1996)
Brookes, A. J., Gene, 234:177-86 (1999)
Brown, P. O. et al., U.S. Pat. No. 5,807,522 (1998)
Bruchez, M. Jr. et al, Science, 281:2013-6 (1998)
Buchholz, F. et al., Nat. Biotechnol., 16:657-62 (1998)
Bulyk, M. L. et al., Nat Biotechnol., 17:573-7 (1999)
Burke, D. T. et al, Science, 236:806-12 (1987)
Burnbaum, J. J., et al., U.S. Pat. No. 5,876,946 (1999)
Campbell, K. H. et al., Nature, 380:64-6 (1996)
Cantor, C. R. et al., U.S. Pat. No. 5,795,714 (1998)
Capecchi, M. R. et al., U.S. Pat. No. 5,487,992 (1996)
Carraway, K. L. et al., U.S. Pat. No. 5,624,816 (1997)
Caskey, C. J. et al., U.S. Pat. No. 5,364,759 (1994)
Cavanagh, J. et al., Protein Nmr Spectroscopy: Principles and Practice, Academic Press, New York (1996)
Chalfie, M. et al., U.S. Pat. No. 5,491,084 (1996)
Chan, W. C. W. et al., Science, 281:2016-8 (1998)
Cech, T. R., Cell, 47:207-16 (1986)
Cech, T. R. et al., PCT Pat. Pub. No. WO 90/11364 (1990)
Cech, T. R. et al., U.S. Pat. No. 4,987,071 (1991)
Cech, T. R. et al., U.S. Pat. No. 5,093,246 (1992)
Chaleff, D. T., U.S. Pat. No. 5,310,882 (1994)
Chappel, S. C. et al., U.S. Pat. No. 5,260,421 (1993)
Cheeseman, P. C., U.S. Pat. No. 5,302,509 (1994)
Chelsky, D., et al., U.S. Pat. No. 5,856,083 (1999)
Chee, P. P. et al., U.S. Pat. No. 5,169,770 (1992)
Chen, L. R. et al., Theriogenology, 52:195-212 (1999)
Chetverin, A. et al., U.S. Pat. No. 5,616,478 (1997)
Cheung, V. G. et al., Proc. Natl. Acad. Sci. USA, 93:14676-9 (1996)
Chien, et al., Proc. Natl. Acad. Sci. USA, 88:9578-82 (1991)
Cho, R. J. et al., Nat. Genet., 23:203-7 (1999)
Church, G. M., U.S. Pat. No. 4,942,124 (1990)
Church, G. M. et al., U.S. Pat. No. 5,149,625 (1992)
Church, G. M., PCT Pat. Pub. No. WO 99/19341 (1999)
Cibelli, J. B. et al., Science, 280:1256-58 (1998)
Clayerie, J. M. et al., Biochimie, 67:437-43 (1985)
Cole, S. P. et al., in Monoclonal Antibodies and Cancer Therapy, Alan R. Liss, Inc., pp. 77-96 (1985)
Cole-Strauss, A. et al., Science, 273:1386-9 (1996)

Cordell, B., U.S. Pat. No. 5,387,742 (1995)
Craig, N. L., Curr. Top. Microbiol. Immunol. 204:27-48 (1996)
Cruickshank, K., U.S. Pat. No. 5,091,519 (1992)
Damha, M. J. et al., Nucleic Acids Research, 18: 3813-21 (1990)
Davis, R. W. et al., Advanced Bacterial Genetics, CSHL Press, Cold Spring Harbor, N.Y. (1980)
Dellaporta, S. L., PCT Pat. Pub. No. WO 99/14373 (1999)
Devlin, J. P., High Throughput Screening, Marcel Dekker, New York (1997)
Dieffenbach, C. et al., PCR Primer: A Laboratory Manual, CSHL Press, Cold Spring Harbor, N.Y. (1995)
Donehower, L. A. et al., U.S. Pat. No. 5,569,824 (1996)
Doolittle, R. F., Methods Enzymol., 183: 99-110 (1990)
Dorsel, A. et al., U.S. Pat. No. 5,945,679 (1999)
Drenth, J., Principles of Protein X-Ray Crystallography, Springer Verlag, Germany (1999)
Drmanac, R. T. et al., U.S. Pat. No. 5,202,231 (1993)
Dubiley, S. et al., Nucleic Acids Res., 25:2259-65 (1997)
Duggan, D. J. et al., Nat Genet., 21(1 Suppl):10-4 (1999)
Dujon, B. et al., U.S. Pat. No. 5,962,327 (1999)
Dupuis, J. et al., Genetics, 151:373-86 (1999)
Eckstein, F., Oligonucleotides and Analogues: A Practical Approach, IRL Press, Oxford (1991).
Eisen, M. B. et al., Methods Enzymol., 303:179-205 (1999)
Farr, S. B. et al., U.S. Pat. No. 5,811,231 (1998)
Fodor, S. P. A. et al., Science 251:767-73 (1991)
Fodor, S. P. A. et al., U.S. Pat. No. 5,445,934 (1995)
Fodor, S. P. A. et al., U.S. Pat. No. 5,871,928 (1999)
Foye, W. O. et al., Principles of Medicinal Chemistry, Lippincott, Williams & Wilkins, Philadelphia (1995)
Frengen, E. et al., Genomics, 58:250-3 (1999)
Friedrich, G. et al., Genes Dev., 5:1513-23 (1991)
Frommer, M. et al., Proc. Natl. Acad. Sci. USA, 89:1827-31 (1992)
Fujiwara, T. et al., U.S. Pat. No. 4,329,591 (1982)
Gait, M. J., Oligonucleotide Synthesis: A Practical Approach, IRL Press, Oxford (1984)
Galbraith, D. W. et al., Methods Cell Biol., 58:315-41 (1999)
Gautier, C. et al., Nucleic Acids Res. 15:6625-41 (1987)
Gebinoga, M. et al., Eur. J. Biochem., 235:256-61 (1996)
Gehrke, L. et al., U.S. Pat. No. 5,286,847 (1994)
Ghosh, S. S. et al., Nucleic Acids Res., 15: 5353-72 (1987)
Gimeno, C. J. et al., U.S. Pat. No. 5,948,639 (1999)
Gingeras, T. R. et al., PCT Pat. Pub. No. WO 88/10315 (1988)
Giordano, A. et al., U.S. Pat. No. 5,807,681 (1998)
Gish, et al., Science, 240: 1520-1522 (1988)
Gjerde, D. T. et al., PCT Pat. Pub. No. WO 99/19514 (1999)
Gold, L. et al. U.S. Pat. No. 5,270,163 (1993)
Gold, L. et al. U.S. Pat. No. 5,475,096 (1995)
Golic, K. G., Science, 252:958-61 (1991)
Golic, K. G., Genetics, 137:551-63 (1994)
Golic, K. G. et al., Genetics, 144:1693-711 (1996)
Goodearl, A. D. J., U.S. Pat. No. 5,882,893 (1999)
Goodman, M. et al., in Burger's Medicinal Chemistry and Drug Discovery, Fifth Edition, Vol. 1, John Wiley, New York, pp. 803-861 (1995)
Gordon, E. M. et al., Combinatorial Chemistry and Molecular Diversity in Drug Discovery, John Wiley, New York (1998)
Gordon, J. W., Int. Rev. Cytol., 115:171-229 (1989)
Gossen, J. A. et al., U.S. Pat. No. 5,602,300 (1997)
Graber, J. H. et al., Genet Anal., 14:215-9 (1999)
Groffen, J. et al., U.S. Pat. No. 5,491,283 (1996)
Gu, H. et al., Science 265:103-6 (1994)
Guegler, K. J. et al., U.S. Pat. No. (1997)
Guggenheimer, R. A. et al., J. Biol. Chem., 259:7807-14 (1984)
Hamilton, B. A., et al., Proc. Natl. Acad. Sci. USA, 88:2731-5 (1991)
Hamilton, B. A., et al., Methods Cell Biol., 44:81-94 (1994)
Hammer, R. E., U.S. Pat. No. 5,489,742 (1996)
Hansch, C. et al., Comprehensive Medicinal Chemistry, Pergamon Press, Oxford (1990)
Harper, J. W. et al., U.S. Pat. No. 4,900,673 (1990)
Haseloff, J. et al., Nature, 334:585-91 (1988)
Hastings, G. A. et al., U.S. Pat. No. 5,501,969 (1996)
Haugland, R. P., Handbook of Fluorescent Probes and Research Chemicals, $7^{th}$ Ed., Molecular Probes Inc., Eugene, Oreg. (1996)
Hawkins, P. R. et al., U.S. Pat. No. 5,587,306 (1996)
Hearn, M. T. W., HPLC of Proteins, Peptides, and Polynucleotides, VCH Publishers, New York (1991)
Helene, C., Anticancer Drug Des., 6:569-84 (1991)
Helene, C. et al., Ann. N.Y. Acad. Sci., 660:27-36 (1992)
Helentjaris, T. et al, U.S. Pat. No. 5,385,835 (1995)
Hensel, M. et al., Science, 269:400-3 (1995)
Hider, R. C. et al., Polypeptide and Protein Drugs: Production, Characterization, and Formulation, Ellis Horwood, New York (1991)
Hillman, J. L. et al., U.S. Pat. No. 5,843,727 (1998)
Hong, Y. et al., Proc. Natl. Acad. Sci. USA, 95:3679-84 (1998)
Horlbeck, E. G., U.S. Pat. No. 5,880,972 (1999)
Huang, S. H., Methods Mol. Biol., 69:89-96 (1997)
Innis, M. et al., PCR Protocols: A Guide to Methods and Applications, Academic Press, San Diego, Calif. (1990)
Inoue, H. et al., Nucleic Acids Res. 15:6131-48 (1987a)
Inoue, H. et al., FEBS Lett. 215:327-30 (1987b)
Inouye, S. et al., Nucleic Acids Res. 13:3101-9 (1985)
Israel, L. et al., U.S. Pat. No. 3,956,099 (1976)
Jablonski, E. et al., Nucl. Acids. Res. 14:6115-28 (1986)
Jakubowski, J. et al., Genetics 153:743-52 (1999)
James, G. L. et al., Science, 260:1937-42 (1993)
Johnson, D. F. et al., Gene., 94:9-14 (1990)
Johnson, M. L. et al., Methods Enzymol., 240:51-68 (1994)
Jones, D. H., in PCR Primer, CSHL Press, Cold Spring Harbor, N.Y., pp. 411-20 (1995)
Jones, T. et al., U.S. Pat. No. 4,699,897 (1987)
Kamb, A. U.S. Pat. No. 5,683,880 (1997)
Kambara, H., U.S. Pat. No. 5,541,420 (1996)
Kandpal, R. P. et al., Proc. Natl. Acad. Sci. USA, 91:88-92 (1994)
Karagyozov, L. et al., Nucleic Acids Res., 21:3911-2 (1993)
Karger, B. L. et al., U.S. Pat. No. 5,571,398 (1996)
Keller G. H. et al., DNA Probes, 2nd Ed., Stockton Press, New York, (1993)
Kenney, M. et al., Biotechniques, 25:516-21 (1998)
Kere, J. et al., Genomics, 14:241-8 (1992)
Keseru, G. M. et al., Molecular Mechanics and Conformational Analysis in Drug Design, Blackwell Science, Boston (1999)
Khrapko, K. R., et al., U.S. Pat. No. 5,552,270 (1996)
Kilby, N. J. et al., Trends Genet., 9:413-421 (1993)
Kim, U. J. et al., Genomics, 22:336-9 (1994)
Kirk, G. L. et al., U.S. Pat. No. 5,798,035 (1998)
Kleckner, N. et al., Methods Enzymol., 204:139-80 (1991)
Kleyn, P. W. et al., U.S. Pat. No. 5,876,919 (1999)
Kobara, Y. et al., Cell, 50:495-508 (1987)
Kohler, G. et al., Nature 256:495-7 (1975)
Koob, M. et al., Science, 250:271-3 (1990)

Kornberg, A. et al., DNA Replication, 2nd Ed., Freeman, San Francisco (1992)
Kozbor, D. et al., Immunology Today 4:72 (1983)
Kozian, D. H. et al., Trends Biotechnol., 17:73-8 (1999)
Krishna, N. R. et al., Biological Magnetic Resonance—Vol. 16: Modern Techniques in Protein NMR, Kluwer Academic Publishers, Netherlands (1999)
Krol et al., BioTechniques 6:958-76 (1988)
Kruglyak, L., Nat. Genet., 22:139-44 (1999)
Krzyzek, R. A. et al., U.S. Pat. No. 5,384,253 (1995)
Kunkel, T. A., U.S. Pat. No. 4,873,192 (1989)
Kwoh, D. Y. et al., Proc. Natl. Acad. Sci. USA, 86:1173-7 (1989)
Ladner, R. C. et al., U.S. Pat. No. 4,946,778 (1990)
Lagerstrom, M. et al., PCR Methods Applic., 1:111-9 (1991)
Landegren, U. et al., Science, 241:1077-80 (1988)
Lander, E. S. et al., Cold Spring Harb. Symp. Quant. Biol., 51 Pt.1:49-62 (1986)
Lander, E. S. et al., Genetics, 121:185-99 (1989)
Landers, J. P., Handbook of Capillary Electrophoresis, CRC Press, Boca Raton, Fla. (1996)
Lane, M. J. et al., Nucleic Acids Res., 25:611-7 (1997)
Lasko, M. et al., Proc. Natl. Acad. Sci. USA, 89:6232-6 (1992)
Lavitrano, M. et al., Cell, 57:717-23 (1989)
Lazzarini, R. A., U.S. Pat. No. 5,602,299 (1997)
Leder, P. et al., U.S. Pat. No. 5,175,383 (1992)
Lee, F. et al., U.S. Pat. No. 5,908,609 (1999)
Lee, L. G. et al., U.S. Pat. No. 5,945,526 (1999)
Lebo, R. V. et al., U.S. Pat. No. 5,723,593 (1998)
Lemaitre, M. et al., Proc. Natl. Acad. Sci. USA, 84:648-52 (1987)
Letsinger, R. L. et al., Proc. Natl. Acad. Sci. USA, 86:6553-6 (1989)
Levinson, D. A. et al., U.S. Pat. No. 5,846,780 (1998)
Li, C. et al., Nucleic Acids Res., 21:1239-44 (1993)
Li, H. et al., U.S. Pat. No. 5,650,295 (1997)
Lin, F.-K., U.S. Pat. No. 4,703,008 (1987)
Liu, Y. G. et al., Genomics, 25:674-81 (1995)
Lizardi, P. M. et al., Nature Genetics, 19:225-32 (1998)
Lizardi, P. M., U.S. Pat. No. 5,854,033 (1998)
Lo, C. W., Mol. Cell. Biol. 3:1803-14 (1983)
Lockhart, D. J. et al. Nature Biotechnology 14:1675-80 (1996)
Logan, et al., Proc. Natl. Acad. Sci. USA, 81:3655-9 (1984)
Lund, V. et al., Nucleic Acids Res., 16:10861-80 (1988)
Lundquist, R. C. et al., U.S. Pat. No. 5,508,468 (1996)
Maher, L. J., Bioassays, 14:807-15 (1992)
Mandecki, W., U.S. Pat. No. 5,641,634 (1997)
Mandecki, W., U.S. Pat. No. 6,361,950 (2002)
Martin, Y. C., Modern Drug Research, vol. 12, Marcel Dekker, New York, pp. 161-216 (1989)
Marton, M. J. et al., Nat. Med., 4:1293-301 (1998)
Maskos U. et al., Nucleic Acids Research, 20: 1679-1684 (1992)
Maskos, U. et al., Nucleic Acids Res., 21: 4663-9 (1993)
Matthews, J. A. et al., Anal. Biochem., 169:1-25 (1988)
Matson, R. S. et al., U.S. Pat. No. 5,429,807 (1995)
Maxam et al., Proc. Natl. Acad. Sci. USA, 74:560-4 (1977)
McRee, D. E., Practical Protein Crystallography, Academic Press, New York (1999)
Menchen, S. M. et al., U.S. Pat. No. 5,188,934 (1993)
Meyer, U. A. et al., Annu. Rev. Pharmacol. Toxicol., 37:269-96 (1997)
Miller, J. H., Experiments in Molecular Genetics, CSHL Press, Cold Spring Harbor, N.Y. (1972)
Mills, R. L., U.S. Pat. No. 5,221,518 (1993)
Mitchell, L. G. et al., Anal. Biochem., 178:239-42 (1989)
Moloney, M. M. et al., U.S. Pat. No. 5,188,958 (1993)
Montgomery, D. D., PCT Pat. Pub. No. WO 98/01221 (1998)
Mosbach, K., Methods in Enzymology, Vol. 44, Academic Press, New York (1976)
Nikiforov, T. et al., U.S. Pat. No. 5,952,174 (1999)
Nuovo, G. J., PCR In situ Hybridization: Protocols And Applications, Raven Press, New York (1992)
Ochman, H. et al., Genetics, 120:621-3 (1988)
Oefner, P. J. et al., U.S. Pat. No. 5,846,832 (1998)
Ogilvie, D. J. et al., Methods Mol. Biol., 54:131-138 (1996)
Ohler, L. D. et al., PCR Methods Appl., 2:51-9 (1992)
Oin, X.-O., U.S. Pat. No. 5,869,040 (1999)
Osslund, T. D., U.S. Pat. No. 5,581,476 (1996)
Ostrander, E. A. et al., Proc. Natl. Acad. Sci. USA, 89:3419-23 (1992)
Paetkau, D., Biotechniques, 26:690-7 (1999)
Panet, A., et al, Proc. Natl. Acad. Sci. USA., 72:2535-9 (1975)
Parce, J. W. et al., U.S. Pat. No. 5,942,443 (1999)
Pardridge, W. M. et al., PCT Pat. Pub. No. WO 89/10134 (1989)
Pastinen, T. et al., Genome Res., 7:606-14 (1997)
Pearson, W. R., Methods Enzymol., 183:63-99 (1990)
Pease, A. C. et al., Proc. Natl. Acad. Sci. USA, 91: 5022-6 (1994)
Perry, A. C. et al., Science, 284:1180-3 (1999)
Pictet, R., in Molecular Recognition Mechanisms, VCH Publishers, New York, pp. 219-35 (1991)
Pierce, G. F. et al., U.S. Pat. No. 5,824,643 (1998)
Pirrung, M. C. et al., U.S. Pat. No. 5,143,854 (1992)
Pirrung, M. C. et al., U.S. Pat. No. 5,405,783 (1995)
Platt, K. A., J. Biol. Chem., 269:28558-62 (1994)
Polymeropoulos, M. H. U.S. Pat. No. 5,378,602 (1995)
Pon, R. T. et al., Biotechniques, 6:768-75 (1988)
Pon, R. T., Methods Mol. Biol., 20:465-96 (1993)
Popoff, M. Y. et al., U.S. Pat. No. 5,618,666 (1997)
Porter, K. W. et al., Nucleic Acids Res., 25:1611-7 (1997)
Powers, D. B. et al., U.S. Pat. No. 5,795,761 (1998)
Press, W. H. et al., in Numerical Recipes in C, Cambridge University Press, pp. 398-470 (1988)
Rabani, E. M., PCT Pat. Pub. No. WO 96/36737 (1996)
Rabani, E. M., PCT Pat. Pub. No. WO 97/07245 (1997)
Rembaum, A. et al., U.S. Pat. No. 4,046,720 (1977)
Rembaum, A., U.S. Pat. No. 4,413,070 (1983)
Rembaum, A., U.S. Pat. No. 4,678,814 (1987)
Richterich, P. et al., Methods Enzymol., 218:187-222 (1993)
Rigas, B. et al., Proc. Natl. Acad. Sci. USA, 83:9591-5 (1986)
Riley, J. H. et al., Nucleic Acids Res., 18:2887-90 (1990)
Robinson, M. O. et al., U.S. Pat. No. 5,489,743 (1996)
Rose, M. D. et al., Methods in Yeast Genetics, CSHL Press, Cold Spring Harbor, N.Y. (1990)
Rosenthal, A., PCT Pat. Pub. No. WO 93/21340 (1993)
Rossi, J., Current Biology, 4:469-71 (1994)
Rothschild, M. F. et al., U.S. Pat. No. 5,550,024 (1996)
Rubenstein, K. E. et al., U.S. Pat. No. 4,190,496 (1980)
Rubin, E. J. et al., Proc. Natl. Acad. Sci. USA, 96:1645-50 (1999)
Ruley, H. E. et al., U.S. Pat. No. 5,627,058 (1997)
Ruther U. et al., EMBO J., 2:1791-4 (1983)
Sabatini, C. E. et al., U.S. Pat. No. 5,624,803 (1999)
Sagner, G. et al., U.S. Pat. No. 5,714,318 (1998)
Saiki, R. K. et al., Proc. Natl. Acad. Sci. USA, 86:6230-4 (1989)

Sambrook et al., Molecular Cloning: A Laboratory Manual, CSHL Press, New York (1989)
Samal, B. B., U.S. Pat. No. 5,874,399 (1999)
Sands, A. et al., PCT Pat. Pub. No. WO 98/14614 (1998)
Sanger, F. et al., Proc. Natl. Acad. Sci. USA, 74:5463-7 (1977)
Santamaria, P. et al., U.S. Pat. No. 5,629,149 (1997)
Sapolsky, R. J. et al., Genet. Anal., 14:187-92 (1999)
Sarin, P. S. et al., Proc. Natl. Acad. Sci. USA, 85:7448-51 (1988)
Sarver, N. et al. Science, 247:1222-5 (1990)
Schena, M. et al, Science, 270:467-70 (1995)
Schmidt, G. et al., PCT Pat. Pub. No. WO 99/02726 (1999)
Scheit, Nucleotide Analogs, John Wiley, New York (1980)
Sedivy, J. M. et al., Proc. Natl. Acad. Sci. USA, 86:227-31 (1989)
Sherman, A. et al., Nat. Biotechnol., 16:1050-3 (1998)
Shin, J. A. et al., Nucleic Acids Res., 19:5233-6 (1991)
Shuber, A. P., U.S. Pat. No. 5,589,330 (1996)
Shukla, A. K., U.S. Pat. No. 5,340,449 (1994)
Silver, J. et al., U.S. Pat. No. 4,994,370 (1991)
Singh-Gasson, S. et al., Nature Biotechnology, 17: 974-78 (1999)
Sisto A. et al., U.S. Pat. No. 4,522,752 (1985)
Skarnes, W. C. et al., Proc. Natl. Acad. Sci. USA, 92:6592-6 (1995)
Skolnick, M. H. et al., U.S. Pat. No. 5,624,819 (1997)
Small, J. A. et al., Mol. Cell. Biol. 5:642-648 (1985)
Smih, F. et al., Nucleic Acids Res. 23:5012-19 (1995)
Smith, G. E. et al., Mol. Cell. Biol., 3:2156-65 (1983)
Smith, G. E. et al., U.S. Pat. No. 4,745,051 (1988)
Smith, V. et al., Proc. Natl. Acad. Sci. USA, 92:6479-83 (1995)
Smithies, O. et al., Nature, 317:230-4 (1985)
Sorge, J. et al, Proc. Natl. Acad. Sci. USA, 86:9208-12 (1989)
Southern, E. et al., Genomics, 13: 1008-17 (1992)
Southern, E., U.S. Pat. No. 5,700,637 (1997)
Souza, L. M., U.S. Pat. No. 4,810,643 (1989)
Souza, L. M., U.S. Pat. No. 5,104,806 (1992)
Stein, C. A. et al., Nucleic Acids Res. 16:3209-21 (1988)
Stemmer, W. P. C., U.S. Pat. No. 5,605,793 (1997)
Stern, M. E. et al., U.S. Pat. No. 5,863,892 (1999)
Stewart, C. L., Methods Enzymol., 225:823-55 (1993)
Still, W. C. et al., U.S. Pat. No. 5,565,324 (1996)
Stockham, T. G. et al., U.S. Pat. No. 5,273,632 (1993)
Stone, E. M. et al., U.S. Pat. No. 5,916,778 (1999)
Strathmann, M. et al., Proc. Natl. Acad. Sci. USA, 88:1247-50 (1991)
Stulich, R. et al., Comput. Appl. Biosci., 5:15-8 (1989)
Suhai, S., Theoretical and Computational Methods in Genome Research., Plenum, N.Y. (1997)
Sutcliffe, J. G. et al., U.S. Pat. No. 5,968,817 (1999)
Swensen, J., Biotechniques, 20: 486-491 (1996)
Szybalski, W., Curr. Opin. Biotechnol., 8: 75-81 (1997)
Taidi-Laskowski, B. et al., Nucleic Acids Res., 16:8157-69 (1988)
Takagi, S. et al., Biotechniques, 14:218-21 (1993)
Tartaglia, L. A. U.S. Pat. No. 5,861,485 (1999)
Taylor, M. D. et al., Peptide-Based Drug Design: Controlling Transport and Metabolism, American Chemical Society, Washington, D.C. (1994)Telenius, H. et al., Genomics, 13:718-25 (1992)
Terhorst, C. P. et al., U.S. Pat. No. 5,530,179 (1996)
Thayer, J. R. et al., Methods Enzymol., 271:147-74 (1996)
Thomas, K. R. et al., Cell, 51:503-12 (1987)
Thompson, S. et al., Cell, 56:313-21 (1989)
Trulson, M. et al, U.S. Pat. No. 5,834,758 (1998)
Tullis, R. H., U.S. Pat. No. 4,904,582 (1990)
Uhlman et al., Chemical Reviews, 90: 543-84 (1990)
Umari, P. et al., Genetics, 143:1831-42 (1996)
Urdea, M. S., U.S. Pat. No. 5,124,246 (1992)
van der Krol, A. R. et al., Biotechniques, 6:958-76 (1988)
van der Putten, H. et al., Proc. Natl. Acad. Sci. USA, 82:6148-52 (1985)
Van Heeke, G. et al., J. Biol. Chem. 264:5503-9 (1989)
Van Ness, J. et al., PCT Pat. Pub. No. WO 97/27331 (1997)
Veerapandian, B., in Burger's Medicinal Chemistry and Drug Discovery, Vol. 1, John Wiley, New York, pp. 303-48 (1995)
Velculescu, V. E. et al., Science, 270:484-7 (1995)
Venton, D. L. et al., U.S. Pat. No. 5,814,460 (1998)
Vidal, M. et al., Trends Biotechnol., 17:374-81 (1999)
Walker, G. T. et al., Nucleic Acids Res., 20:1691-6 (1992)
Walker, G. T., U.S. Pat. No. 5,270,184 (1993)
Wagner, M. J. et al., Proc. Natl. Acad. Sci. USA, 78:1441-5 (1981)
Wagner, R., Nature 372:333-5 (1994)
Wagner, T. E. et al, U.S. Pat. No. 4,873,191 (1989)
Wang, D. G. et al., Science, 280:1077-82 (1998)
Wachsman, W. et al., U.S. Pat. No. 5,616,475 (1997)Webb, D. M., U.S. Pat. No. 5,948,953 (1999)
Webb, T. R. et al., U.S. Pat. No. 4,659,774 (1987)
Wei, Y.-F. et al., U.S. Pat. No. 5,723,311 (1998)
Wei, Y.-F. et al., U.S. Pat. No. 5,858,705 (1999)
Weiler, J. et al., Nucleic Acids Res., 25:2792-9 (1997)
Weiner, D. B. et al., Biological Approaches to Rational Drug Design, CRC Press, Boca Raton, Fla. (1994)
Weiner, D. B. et al., Chemical and Structural Approaches to Rational Drug Design, CRC Press, Boca Raton, Fla. (1995)
Weinshilboum, R. M. et al., U.S. Pat. No. 5,470,737 (1995)
Weissmann, C., U.S. Pat. No. 4,530,901 (1985)
Weston, A. et al., HPLC and CE: Principles and Practice, Academic Press, San Diego, Calif. (1997)
Wilkie, T. M. et al., Methods Enzymol., 237:327-44 (1994)
Wilson, S. R. et al., Combinatorial Chemistry: Synthesis and Application, John Wiley, New York (1997)
Wolf, S. F. et al., Nucleic Acids Res., 15: 2911-26 (1987)
Wolff, M. E., Burger's Medicinal Chemistry and Drug Discovery, Fifth Edition, John Wiley, New York (1995)
Wong, W. H., U.S. Pat. No. 5,935,793 (1999)
Wu C. et al., Nucleic Acids Research, 24:2614-5 (1996)
Xiong, M. et al., Am. J. Hum. Genet., 64:629-40 (1999)
Xu, L. et al., Anal. Chem., 69:3595-602 (1997)
Xu, T. et al., Development, 117:1223-37 (1993)
Yamamoto, T. et al., Cell, 22:787-97 (1980)
Yamashita, T. et al., U.S. Pat. No. 5,332,668 (1994)
Ye, S. et al., Mol. Med. Today, 4:431-7 (1998)
Yoder, J. I. et al., U.S. Pat. No. 5,225,341 (1993)
Yoshida, Y. et al., Nucleic Acids Res., 21:3553-62 (1993)
Zaug, A. J. et al., Science, 224:574-8 (1984)
Zaug, A. J. et al., Science, 231:470-5 (1986a)
Zaug, A. J. et al., Nature, 324:429-33 (1986b)
Zhang, D. Y. et al., Gene, 211: 277-85 (1998)
Zhao, H. et al., Nat. Biotechnol., 16:258-61 (1998)
Zon, G., Pharm. Res. 5:539-49 (1988)
Zukowski, M. M. et al., U.S. Pat. No. 4,914,031 (1990)

I claim:

1. A parallel method for polynucleotide sequencing, comprising:
   a) preparing a library comprising a collection of two or more sample-tagged polynucleotide clones;
   b) carrying out a nucleic acid sequencing reaction on the library wherein a first sequencing primer binding site or no sequencing primer binding site is used to generate a plurality of tagged reaction products from the sample-tagged clones in the collection;
   c) separating the reaction products according to size;
   d) collecting fractions of the separated reaction products;
   e) amplifying the products collected in step (d) to generate tagged amplicons;
   f) hybridizing the tagged amplicons to an array comprising tag complements wherein the array is a particulate array; and
   g) determining a plurality of polynucleotide sequences of the sample-tagged clones by detecting the hybridizations to deconvolute a plurality of sequence ladders for the sample-tagged clones in the collection.

2. A parallel method for polynucleotide sequencing, comprising:
   a) preparing a library comprising sample-tagged polynucleotide clones;
   b) carrying out a nucleic acid sequencing reaction on the library to generate a plurality of tagged reaction products;
   c) separating the reaction products according to size;
   d) collecting fractions of the separated reaction products;
   e) hybridizing the products collected in step (d) to an array comprising tag complements wherein the array is a particulate array;
   f) amplifying the hybridized reaction products in situ; and
   g) determining a plurality of polynucleotide sequences of the sample-tagged clones by detecting the amplified reaction products to deconvolute a plurality of sequence ladders for the sample-tagged clones.

* * * * *